(12) United States Patent
Manoharan

(10) Patent No.: US 6,762,169 B1
(45) Date of Patent: Jul. 13, 2004

(54) LIGAND-CONJUGATED OLIGOMERIC COMPOUNDS

(75) Inventor: Muthiah Manoharan, La Costa, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/594,387

(22) Filed: Jun. 15, 2000

Related U.S. Application Data

(63) Continuation-in-part of application No. 09/334,130, filed on Jun. 15, 1999.

(51) Int. Cl.$^7$ .................. C07H 21/04; A61K 48/00; A61K 38/00
(52) U.S. Cl. .................. 514/44; 514/2; 435/440; 435/455; 530/402; 536/23.1; 536/24.1; 536/24.5
(58) Field of Search .................. 435/6, 69.1, 91.1, 435/440, 325, 320.1, 7.1, 7.2, 455; 514/44; 530/402; 536/23.1, 23.5, 24.5, 24.1

(56) References Cited

U.S. PATENT DOCUMENTS

| | | | |
|---|---|---|---|
| 3,687,808 A | 8/1972 | Merigan et al. | 195/28 |
| 4,469,863 A | 9/1984 | Ts'o et al. | 536/27 |
| 4,476,301 A | 10/1984 | Imbach et al. | 536/27 |
| 4,587,044 A | 5/1986 | Miller et al. | 530/211 |
| 4,605,735 A | 8/1986 | Miyoshi et al. | 536/27 |
| 4,667,025 A | 5/1987 | Miyoshi et al. | 536/27 |
| 4,689,320 A | 8/1987 | Kaji | 514/44 |
| 4,762,779 A | 8/1988 | Snitman | 435/6 |
| 4,789,737 A | 12/1988 | Miyoshi et al. | 536/27 |
| 4,806,463 A | 2/1989 | Goodchild et al. | 435/5 |
| 4,824,941 A | 4/1989 | Gordon et al. | 530/403 |
| 4,828,979 A | 5/1989 | Klevan et al. | 435/6 |
| 4,835,263 A | 5/1989 | Nguyen et al. | 536/27 |
| 4,845,205 A | 7/1989 | Huynh Dinh et al. | 536/28 |
| 4,876,335 A | 10/1989 | Yamane et al. | 536/27 |
| 4,904,582 A | 2/1990 | Tullis | 435/6 |
| 4,948,882 A | 8/1990 | Ruth | 536/27 |
| 4,958,013 A | 9/1990 | Letsinger | 536/27 |
| 4,973,745 A | 11/1990 | Blaschke et al. | 562/401 |
| 4,981,957 A | 1/1991 | Lebleu et al. | 536/27 |
| 5,004,810 A | 4/1991 | Draper | 536/27 |
| 5,013,830 A | 5/1991 | Ohtsuka et al. | 536/27 |
| 5,023,243 A | 6/1991 | Tullis | 514/44 |
| 5,034,506 A | 7/1991 | Summerton et al. | 528/391 |
| 5,082,830 A | 1/1992 | Brakel et al. | 514/44 |
| 5,087,617 A | 2/1992 | Smith | 514/44 |
| 5,098,890 A | 3/1992 | Gerwirtz et al. | 514/44 |
| 5,109,124 A | 4/1992 | Ramachandran et al. | 536/27 |
| 5,112,963 A | 5/1992 | Pieles et al. | 536/27 |
| 5,118,800 A | 6/1992 | Smith et al. | 536/23 |
| 5,118,802 A | 6/1992 | Smith et al. | 536/27 |
| 5,130,302 A | 7/1992 | Spielvogel et al. | 514/45 |
| 5,134,066 A | 7/1992 | Rogers et al. | 435/91 |
| 5,135,917 A | 8/1992 | Burch | 514/44 |
| 5,138,045 A | 8/1992 | Cook et al. | 536/27 |
| 5,149,797 A | 9/1992 | Pederson et al. | 536/27 |
| 5,166,195 A | 11/1992 | Ecker | 514/44 |
| 5,166,315 A | 11/1992 | Summerton et al. | 528/406 |
| 5,166,320 A | 11/1992 | Wu et al. | 530/395 |
| 5,175,273 A | 12/1992 | Bischofberger et al. | 536/27 |
| 5,177,196 A | 1/1993 | Meyer, Jr. et al. | 536/22.1 |
| 5,185,444 A | 2/1993 | Summerton et al. | 544/81 |
| 5,188,897 A | 2/1993 | Suhadolnik et al. | 428/402.2 |
| 5,194,428 A | 3/1993 | Agrawal et al. | 514/44 |
| 5,212,295 A | 5/1993 | Cook | 536/26.7 |
| 5,214,134 A | 5/1993 | Weis et al. | 536/25.3 |
| 5,214,136 A | 5/1993 | Lin et al. | 514/44 |
| 5,216,141 A | 6/1993 | Benner | 536/27.13 |
| 5,218,105 A | 6/1993 | Cook et al. | 536/25.31 |
| 5,220,007 A | 6/1993 | Pederson et al. | 536/23.1 |
| 5,223,168 A | 6/1993 | Holt | 252/142 |
| 5,235,033 A | 8/1993 | Summerton et al. | 528/391 |
| 5,242,906 A | 9/1993 | Pagano et al. | 514/44 |
| 5,245,022 A | 9/1993 | Weis et al. | 536/24.5 |
| 5,254,469 A | 10/1993 | Warren, III et al. | 435/188 |
| 5,256,775 A | 10/1993 | Froehler | 536/25.6 |
| 5,258,506 A | 11/1993 | Urdea | 536/23.1 |
| 5,262,536 A | 11/1993 | Hobbs, Jr. | 546/25 |
| 5,264,423 A | 11/1993 | Cohen et al. | 514/44 |
| 5,264,562 A | 11/1993 | Matteucci | 536/23.1 |
| 5,264,564 A | 11/1993 | Matteucci | 536/23.1 |
| 5,272,250 A | 12/1993 | Spielvogel et al. | 530/300 |
| 5,276,019 A | 1/1994 | Cohen et al. | 514/44 |
| 5,278,302 A | 1/1994 | Caruthers et al. | 536/24.5 |
| 5,286,717 A | 2/1994 | Cohen et al. | 514/44 |
| 5,292,873 A | 3/1994 | Rokita et al. | 536/24.3 |

(List continued on next page.)

FOREIGN PATENT DOCUMENTS

| | | |
|---|---|---|
| EP | 0 251 283 | 6/1987 |
| WO | WO 86/02929 | 5/1986 |
| WO | WO 90/10448 | 9/1990 |
| WO | WO 91/10671 | 7/1991 |
| WO | WO 93/07883 | 4/1993 |

OTHER PUBLICATIONS

Kleinberg et al., Am J Health–Syst Pharm (Jun. 1995) vol. 52, pp. 1323–1336.*

(List continued on next page.)

*Primary Examiner*—Sean McGarry
(74) *Attorney, Agent, or Firm*—Woodcock Washburn LLP

(57) ABSTRACT

Ligand-conjugated oligomeric compounds are described wherein ligands are conjugated to one or more sites on an oligomeric compound including the 2'-, 3'-, 5'-, nucleobase and internucleotide linkage sites. The ligand can be attached via an optional linking group. Ligands are selected for conjugation that bind to one or more cellular, serum or vascular proteins imparting enhanced pharmacokinetic properties to the resulting ligand-conjugated oligomeric compounds. Also provided are methods for increasing the concentration of an oligonucleotide in serum and methods for increasing the capacity of serum for an oligonucleotide. Further, methods for increasing the binding of an oligonucleotide to a portion of the vascular system is described. Also provided are methods for promoting cellular uptake of an oligonucleotide in cells.

25 Claims, 2 Drawing Sheets

U.S. PATENT DOCUMENTS

| | | | |
|---|---|---|---|
| 5,317,098 A | 5/1994 | Shizuya et al. | 536/23.1 |
| 5,319,080 A | 6/1994 | Leumann | 536/27.1 |
| 5,321,131 A | 6/1994 | Agrawal et al. | 536/25.34 |
| 5,359,044 A | 10/1994 | Cook et al. | |
| 5,366,878 A | 11/1994 | Pederson et al. | 435/91.3 |
| 5,367,066 A | 11/1994 | Urdea et al. | 536/24.3 |
| 5,371,241 A | 12/1994 | Brush et al. | 549/220 |
| 5,378,825 A | 1/1995 | Cook et al. | 536/25.34 |
| 5,386,023 A | 1/1995 | Sanghvi et al. | 536/25.3 |
| 5,391,723 A | 2/1995 | Priest | 536/23.1 |
| 5,393,878 A | 2/1995 | Leumann | 536/28.2 |
| 5,399,676 A | 3/1995 | Froehler | 536/23.1 |
| 5,403,711 A | 4/1995 | Walder et al. | 435/6 |
| 5,405,938 A | 4/1995 | Summerton et al. | 528/406 |
| 5,405,939 A | 4/1995 | Suhadolnik et al. | 530/322 |
| 5,414,077 A | 5/1995 | Lin et al. | 536/24.3 |
| 5,416,016 A | 5/1995 | Low et al. | 435/240.1 |
| 5,416,203 A | 5/1995 | Letsinger | 536/25.34 |
| 5,432,272 A | 7/1995 | Benner | 536/25.3 |
| 5,434,257 A | 7/1995 | Matteucci et al. | 536/24.3 |
| 5,446,137 A | 8/1995 | Maag et al. | 536/23.1 |
| 5,451,463 A | 9/1995 | Nelson et al. | 428/402 |
| 5,453,496 A | 9/1995 | Caruthers et al. | 536/24.5 |
| 5,455,233 A | 10/1995 | Spielvogel et al. | 514/44 |
| 5,457,187 A | 10/1995 | Gmeiner et al. | 536/25.5 |
| 5,457,191 A | 10/1995 | Cook et al. | 536/27.13 |
| 5,459,255 A | 10/1995 | Cook et al. | 536/27.13 |
| 5,466,677 A | 11/1995 | Baxter et al. | 514/44 |
| 5,466,786 A | 11/1995 | Buhr et al. | 536/26.26 |
| 5,470,967 A | 11/1995 | Huie et al. | 536/24.3 |
| 5,476,925 A | 12/1995 | Letsinger et al. | 536/23.1 |
| 5,484,908 A | 1/1996 | Froehler et al. | 536/24.31 |
| 5,486,603 A | 1/1996 | Buhr | 536/24.3 |
| 5,489,677 A | 2/1996 | Sanghvi et al. | 536/22.1 |
| 5,491,133 A | 2/1996 | Walder et al. | 514/44 |
| 5,502,177 A | 3/1996 | Matteucci et al. | |
| 5,506,351 A | 4/1996 | McGee | 536/55.3 |
| 5,510,475 A | 4/1996 | Agrawal et al. | 536/24.3 |
| 5,512,439 A | 4/1996 | Hornes et al. | 435/6 |
| 5,512,667 A | 4/1996 | Reed et al. | 536/24.31 |
| 5,514,785 A | 5/1996 | Van Ness et al. | 536/22.1 |
| 5,519,126 A | 5/1996 | Hecht | 536/24.3 |
| 5,519,134 A | 5/1996 | Acevedo et al. | 544/243 |
| 5,521,302 A | 5/1996 | Cook | 536/25.31 |
| 5,525,465 A | 6/1996 | Haralambidis et al. | 435/6 |
| 5,525,711 A | 6/1996 | Hawkins et al. | 536/22.1 |
| 5,536,821 A | 7/1996 | Agrawal et al. | 536/22.1 |
| 5,539,082 A | 7/1996 | Nielsen et al. | 530/300 |
| 5,541,306 A | 7/1996 | Agrawal et al. | 536/22.1 |
| 5,541,307 A | 7/1996 | Cook et al. | 536/23.1 |
| 5,541,313 A | 7/1996 | Ruth | 536/24.3 |
| 5,543,508 A | 8/1996 | Haseloff et al. | 536/23.2 |
| 5,545,729 A | 8/1996 | Goodchild et al. | 536/24.5 |
| 5,545,730 A | 8/1996 | Urdea et al. | 536/28.51 |
| 5,550,111 A | 8/1996 | Suhadolnik et al. | 514/44 |
| 5,552,538 A | 9/1996 | Urdea et al. | 536/24.3 |
| 5,552,540 A | 9/1996 | Haralambidis | 536/25.34 |
| 5,554,746 A | 9/1996 | Ravikumar et al. | 540/200 |
| 5,561,225 A | 10/1996 | Maddry et al. | 536/23.1 |
| 5,563,253 A | 10/1996 | Agrawal et al. | 536/22.1 |
| 5,565,350 A | 10/1996 | Kmiec | 435/172.3 |
| 5,565,552 A | 10/1996 | Magda et al. | 534/11 |
| 5,567,810 A | 10/1996 | Weis et al. | 536/25.3 |
| 5,567,811 A | 10/1996 | Misiura et al. | 536/25.34 |
| 5,571,799 A | 11/1996 | Tkachuk et al. | 514/47 |
| 5,571,902 A | 11/1996 | Ravikumar et al. | 536/22.1 |
| 5,574,142 A | 11/1996 | Meyer, Jr. et al. | 536/23.1 |
| 5,576,427 A | 11/1996 | Cook et al. | 536/23.1 |
| 5,578,717 A | 11/1996 | Urdea et al. | 536/26.1 |
| 5,578,718 A | 11/1996 | Cook et al. | 536/27.21 |
| 5,580,731 A | 12/1996 | Chang et al. | 435/6 |
| 5,585,481 A | 12/1996 | Arnold, Jr. et al. | 536/25.33 |
| 5,587,361 A | 12/1996 | Cook et al. | 514/44 |
| 5,587,371 A | 12/1996 | Sessler et al. | 514/185 |
| 5,587,469 A | 12/1996 | Cook et al. | 536/23.1 |
| 5,587,470 A | 12/1996 | Cook et al. | 536/23.1 |
| 5,591,584 A | 1/1997 | Chang et al. | 435/6 |
| 5,591,722 A | 1/1997 | Montgomery et al. | 514/45 |
| 5,594,121 A | 1/1997 | Froehler et al. | 536/23.5 |
| 5,595,726 A | 1/1997 | Magda et al. | 424/9.61 |
| 5,596,086 A | 1/1997 | Matteucci et al. | 536/22.1 |
| 5,596,091 A | 1/1997 | Switzer | 536/24.5 |
| 5,597,696 A | 1/1997 | Linn et al. | 435/6 |
| 5,597,909 A | 1/1997 | Urdea et al. | 536/24.3 |
| 5,599,797 A | 2/1997 | Cook et al. | 514/44 |
| 5,599,923 A | 2/1997 | Sessler et al. | 540/145 |
| 5,599,928 A | 2/1997 | Hemmi et al. | 540/474 |
| 5,602,240 A | 2/1997 | De Mesmaeker et al. | 536/23.1 |
| 5,607,691 A | 3/1997 | Hale et al. | 424/449 |
| 5,608,046 A | 3/1997 | Cook et al. | 536/23.1 |
| 5,610,289 A | 3/1997 | Cook et al. | 536/25.34 |
| 5,610,300 A | 3/1997 | Altmann et al. | 544/244 |
| 5,614,617 A | 3/1997 | Cook et al. | 536/23.1 |
| 5,618,704 A | 4/1997 | Sanghvi et al. | 435/91.5 |
| 5,623,065 A | 4/1997 | Cook et al. | 536/23.1 |
| 5,623,070 A | 4/1997 | Cook et al. | 536/27.6 |
| 5,625,050 A | 4/1997 | Beaton et al. | 536/24.1 |
| 5,627,053 A | 5/1997 | Usman et al. | 435/91.1 |
| 5,633,360 A | 5/1997 | Bischofberger et al. | 536/22.1 |
| 5,639,873 A | 6/1997 | Barascut et al. | 536/25.3 |
| 5,646,265 A | 7/1997 | McGee | 536/25.34 |
| 5,652,355 A | 7/1997 | Metelev et al. | 536/24.5 |
| 5,652,356 A | 7/1997 | Agrawal | 536/24.5 |
| 5,658,873 A | 8/1997 | Bertsch-Frank et al. | 510/375 |
| 5,663,312 A | 9/1997 | Chaturvedula | 536/22.1 |
| 5,670,633 A | 9/1997 | Cook et al. | 536/23.1 |
| 5,677,437 A | 10/1997 | Teng et al. | 536/23.1 |
| 5,677,439 A | 10/1997 | Weis et al. | 536/23.1 |
| 5,681,941 A | 10/1997 | Cook et al. | 536/23.1 |
| 5,688,941 A | 11/1997 | Cook et al. | 536/25.3 |
| 5,697,248 A | 12/1997 | Brown et al. | 73/290 |
| 5,700,920 A | 12/1997 | Altmann et al. | 536/221 |
| 5,700,922 A | 12/1997 | Cook | 536/23.1 |
| 5,714,142 A | 2/1998 | Blaney et al. | 424/85.2 |
| 5,714,166 A | 2/1998 | Tomalia et al. | 424/486 |
| 5,714,331 A | 2/1998 | Buchardt et al. | 435/6 |
| 5,719,262 A | 2/1998 | Buchardt et al. | 530/300 |
| 5,750,692 A | 5/1998 | Cook et al. | 544/253 |
| 5,789,573 A * | 8/1998 | Baker et al. | |
| 5,846,782 A | 12/1998 | Wickham et al. | 435/69.7 |
| 5,859,221 A | 1/1999 | Cook et al. | 536/23.1 |
| 5,955,589 A | 9/1999 | Cook et al. | 536/23.1 |

OTHER PUBLICATIONS

McLure et al., Br J Clin Pharmacol, Feb. 2000, vol. 49, pp. 453–461.*

Lagrange et al., Fundam. Clin. Pharmacol. 1998: 12:286–291.*

Agrawal et al., "Effect of aspirin on protein binding and tissue disposition of oligonucleotide phosphorothioate in rats," *J. Drug Targeting*, 1998, 5, 303–313.

Asseline, U. et al., "Nucleic acid–bindind molecules with high affinity and base sequence specificity: Intercalating agents covalently linked to oligodeoxynucleotides", *Proc. Natl. Acad. Sci.*, 1984, 81, 3297–3301.

Atherton, E. et al., "The Fluorenylmethoxycarbonyl Amino Protecting Group", *The Peptides*, 1987, 9, 1–39.

Beaucage, S.L. et al., "Advances in the Synthesis of Oligonucleotides by the Phosphoramidite Approach", *Tetrahedron*, 1992, 48, 2223–2311.

Buzayan, J.M. et al., "Satellite tobacco ringspot virus RNA: A subset of the RNA sequence is sufficient for autolytic processing", *Proc. Natl. Acad. Sci. USA*, 1986, 83, 8859–8862.

Chollet, A., "Selective Attachment of Oligonucleotides to Interleukin 1β and Targeted Delivery to Cells", *Nucleosides & Nucleotides*, 1990, 9, 957–966.

Cook, P.D., "Medicinal Chemistry of Antisense Oligonucleotides—future opportunities", *Anti–Cancer Drug Design*, 1991, 6, 585–607.

Corey, D.R. et al., "Generation of a Hybrid Sequence–Specific Single–Stranded Deoxyribonuclease", *Science*, 1987, 238, 1401–1403.

Corey, D.R. et al., "Sequence–Selective Hydrolysis of Duplex DNA by and Oligonucleotide–Directed Nuclease", *J. Am. Chem. Soc.*, 1989, 111, 8523–8252.

Crooke, S.T. et al., "Pharmacokinetic Properties of Several Novel Oligonucleotide Analogs in mice", *J. Pharmacol. Exp. Therapeutics*, 1996, 277, 923–937.

Delgado, C. et al., "The Uses and Properties of PEG–Linked Proteins", *Crit. Rev. in Therapeutic Drug Carrier Sys.*, 1992, 9, 249–304.

Dreyer, G.B. et al., "Sequence–specific cleavage of single–stranded DNA: Oligodeoxynucleotide–EDTA•FE(II)", *Proc. Natl. Acad. Sci.*, 1985, 82, 968–972.

Englisch, U. et al., "Chemically Modified Oligonucleotides as Probes and Inhibitors", *Angew. Chem. Int. Ed. Eng.*, 1991, 30, 613–629.

Forster, A.C. et al., "Self–Cleavage of Virusoid RNA is Performed by the Proposed 55–Nucleotide Active Site", *Cell*, 1987, 50, 9–16.

Frier, S.M. et al., "The ups and downs of nucleic acid duplex stability: structure–stability studies on chemically–modified DNA:RNA duplexes", *Nucl. Acids Res.*, 1997, 25, 4429–4443.

Guerra, F.I. et al., "Synthetic 6–Glucosyl Phospholipid as a Drug Transport System", *Tetrahedron Letts.*, 1987, 28, 3581–3584.

Hamm, M. L. et al., "Incoporation of 2'–Deoxy–2'–mercaptocytidine into Oligonucleotides via Phosphoramidite Chemistry," *J. Org. Chem.*, 1997, 62, 3415–3420.

Haralambidis, J. et al., "The Solid Phase Synthesis of Oligonucleotides Containing a 3'–Peptide Moeity", *Tetrahdeon Letts.*, 1987, 28, 5199–5202.

Haralambidis, J. et al., "Preparation of base–modified nucleosides suitable for non–radioactive label attachment and their incorporation into synthetic oligodeoxyribonucleotides", *Nucl. Acids. Res.*, 1987, 15, 4857–4876.

He et al., "Atomic structure and chemistry of human serum albumin," *Nature*, 1992, 358, 209–215.

Herve et al., "Drug Binding in Plasma: A Summary of Recent Trends in the Study of Drug and Hormone Binding," *Clin. Pharmacokinet.*, 1994, 26(1), 44–58.

Jablonski, E. et al., "Preparation of Oligodeoxynucleotide— alkaline phosphatase conjugates and their use as hybridization probes", *Nucl. Acids Res.*, 1986, 14, 6115–6128.

Juby et al., "Facile Preparation of 3'Oligonucleotide–Peptide Conjugates," *Tetra. Letts.*, 1991, 32, 879–882.

Kabanov, A.V., "A new class of antivirals: antisense olgonucleotides combined with a hydrophobic substituent effecively inhibit influenza virus reproduction and synthesis of virus–specific proteins in MDCK cells", *FEBS Letts.*, 1990, 259, 327–330.

Kornberg, A. et al., *DNA Replication*, 1980, W.H. Freeman & Co., San Francisco, 4–7.

Krieg, A.M. et al., "Uptake of Oligodeoxyribonucleotides by Lymphoid Cells Is Heterogenous and Inducible", *Antisense Res. & Dev.*, 1991, 1, 161–171.

Kroschwitz, J.I., "Polynucleotides", *Concise Encyclopedia of Polymer Science and Engineering*, 1990, John Wiley & Sons, New York, 858–859.

Kumar, P. et al., "Improved Methods for 3'–O–Succinylation of 2'–Deoxyribo–And Ribonucleosides and their Covalent Anchoring on Polymer Supports for Oligonucleotide Synthesis," *Nucleosides & Nucleotides*, 1993, 12(6), 565–584.

Lemairte et al., "Specific antiviral activity of a poly(L–lysine)–conjugated oligodeoxyribonucleotide sequence complementary to vesicular stomatitis virus N protein mRNA initiation site," *Proc. Natl. Acad. Sci.*, 1986, 84, 648–652.

Leonetti, J.P. et al., "Biological Activity of Oligonucleotide-Poly(L–lysine) Conjugates: Mechanism of Cell Uptake", *Bioconjugate Chem.*, 1990, 1, 149–153.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Manoharan, M. et al., "Chemical Modifications to Improve Uptake and Bioavailability of Antisense Oligonucleotides", *Annals NY Acad. Sciences*, 1992, 660, 306–309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Cholic Acid–Oligonucliotide Conjugates for Antisense Applications", *Bioorganic Med. Chem. Letts.*, 1994, 4, 1053–1060.

Manoharan M. et al., "Oligonucleotide Conjugates: Alteration of Pharmacokinetic Propertis of Antisense Agents", *Nucleosides and Nucleotides*, 1995, 14, 969–973.

Manoharan, M. et al., "2'–O– and 3'–O– Pyrimidine Aminothether–Containing Oligonucleotides: Synthesis and Conjugation Chemistry", *Tetrahedron Letts.*, 1995, 3647–3650.

Manoharan, M. et al., "Lipidic Nucleic Acids", *Tetrahedron Letts.*, 1995, 36, 3651–3654.

Martin, P., "Ein neuer Zugang zu 2'–O–Alkylribonucleosiden und Eigenschaften deren Oligonucleotide", *Helvetica Chemica Acta*, 1995, 78, 486–504 (English summary included).

Melikian et al., "Chemical Ionization Mass Spectra of Phenothiazine Derivatives and Their Oxygenated Analogs," *J. Pharm. Sci.*, 1977, 66, 228–232.

Miller, P.S. et al., "A New approach to chemotherapy based on molecular biology and nucleic acid chemistry: Matagen (masking tape for gene expression)", *Anti–Cancer Drug Des.*, 1987, 2, 117–128.

Mishra, R.K. et al., "Improved leishmanicidal effect of phosphorotioate antisense oligonucleotides by LDL–medicated delivery", *Biochim. Et. Biophysica*, 1995, 1264, 229–237.

Nelson, P.S. et al., "Bifunctional oligonucleotide probes synthesized using a novel CPG: support are able to detect single base pair mutations", *Nucl. Acids Res.,* 1989, 17, 7187–7195.

Nielsen, P.E. et al., "Sequence–Selective Recognition of DNA by Strand Displacement with a Thymine–Substituted Polyamide", *Science,* 1991, 254, 1497–1500.

Oberhauser, B. et al., "Effect incorporation of 2′–O–methyl–oligonucleotides into liposomes and enhanced cell association through modification with thiocholesterol", *Nucl. Acids Res.,* 1992, 20, 533–538.

Olson et al., "Chapter 33. Plasma Protein Binding of Drugs," *Annual Rep. Med. Chem.,* 1996, 31, 327–336.

Ouchi, T. et al., "Synthesis and Antitumor Activity of Poly(Ethylene Glycol)s Linked to 5′–Fluorouracil via a Urethane or Urea Bond", *Drug Des. & Disc.,* 1992, 9, 93–105.

Peters, Jr., "Serum Albumin," *Adv. Protein Chem.,* 1985, 37, 161–245.

Polushin, N. N. et al., "Synthesis of Oligonucleotides Containing 2′–Azido–and 2′–Amino″–deoxyuridine Using Phosphotriester Chemistry," *Tetrahedron Letts.,* 1996, 37(19), 3227–3230.

Ramirez, F. et al., "Nucleotidophospholipids: Oligonucleotide Derrivatives with Membrane–Recognition Groups",*J. Am. Chem. Soc.,* 1982, 104, 5483–5486.

Ravasio, N. et al., "Selective Hydrogenations Promoted by Copper Catalysts. 1. Chemoselectivity, Regioselectivity, and Stereoselectivity in the Hydrogenation of 3–Substituted Steroids",*J. Org. Chem.,* 1991, 56, 4329–4333.

Rykova et al., "Serum immunoglobulins interact with oligonucleotides," *FEBS Letts.,* 1994, 334, 96–98.

Saison–Behmoaras, T. et al., "Short modified antisense oligonucleotides directed against Ha–ras point mutation induce selective cleavage of the mRNA and inhibit T24 cells proliferation", *EMBO J.,* 1991, 10, 1111–1118.

Samukov, V.V. et al., "2–(4–Nitrophenyl) sulfonylethoxycarbonyl (Nse) Group as a Base–Labile α–Amino Protection for Solic Phase Peptide Synthesis", *Tetrahedron Letts.,* 1994, 35, 7821–7824.

Sanghvi, Y.S., "Heterocyclic Base Modifications in Nucleic acids and their Applications in Antisense Oligonucleotides", *Antisense Research and Applications,* 1993, Chapter 15, CRC Press, Boca Raton, 273–288.

Secrist, J.A. et al., "Synthesis and Biological Activity of 4′–Thionucleosides", *10th International Roundtable: Nucleosides, Nucleotides and their Biological Applications,* Sep. 16–20, 1992, Abstract 21, Park City, Utah, 40.

Shea, R.G. et al., "Synthesis, hybridization properties and antiviral activity of lipid–oligodeoxynucletide conjugates", *Nucl. Acids Res.,* 1990, 18, 3777–3783.

Svinarchuk, F.P. et al., "Inhibition of HIV proliferation in MT–4 cells by antisense oligonucleotides conjugated to lipophilic groups", *Biochimie,* 1993, 79, 49–54.

Telser, J. et al., "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements", *J. Am. Chem. Soc.,* 1989, 111, 6966–6976.

Thomson, J.B. et al., "Synthesis and Properties of Diuridine Phosphate Analogues Containing Thio and Amino Modifications," *J. Org. Chem.,* 1996, 61, 6273–6281.

Verhart, C.G.J., "New base–labile amino–protective groups for peptide synthesis", *Recl. Trav. Chim. Pays–Bas,* 1988, 107, 621–626.

Yamana, K. et al., "Synthesis and Interactive Properties of an Oligonucleotide with Anthraquinone at the Sugar Frament", *Biconjugate Chem,* 1990, 1, 319–324.

Zuckermann, R.N. et al., "Site–Selective Cleavage of RNA by a Hybrid Enzyme", *J. Am. Chem. Soc.,* 1988, 110, 1614–1615.

\* cited by examiner

LIGAND-CONJUGATED OLIGOMERIC COMPOUNDS

CROSS-REFERENCE TO RELATED APPLICATIONS

This patent application is a continuation-in-part of U.S. patent application Ser. No. 09/334,130, filed Jun. 15, 1999, now pending. The foregoing patent application is assigned to the same assignee as this patent application and is incorporated herein by reference.

FIELD OF THE INVENTION

The present invention relates to ligand-conjugated oligomeric compounds which bind to protein molecules and possess enhanced pharmacokinetic properties. The present invention further relates to methods for increasing the concentration of oligomeric compounds in serum and methods for promoting the cellular uptake of oligomeric compounds in cells.

BACKGROUND OF THE INVENTION

Protein synthesis is directed by nucleic acids through the intermediacy of messenger RNA (mRNA). Antisense methodology is the complementary hybridization of relatively short oligonucleotides to mRNA or DNA such that the normal, essential functions, such as protein synthesis, of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally-occurring events that provide the disruption of the nucleic acid function, discussed by Cohen (*Oligonucleotides: Antisense Inhibitors of Gene Expression*, CRC Press, Inc., 1989, Boca Raton, Fla.) are thought to be of two types. The first, hybridization arrest, describes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller et al. (1987) *Anti-Cancer Drug Design*, 2:117–128), and α-anomer oligonucleotides are the two most extensively studied antisense agents which are thought to disrupt nucleic acid function by hybridization arrest.

Another means by which antisense oligonucleotides in disrupt nucleic acid function is by hybridization to a target mRNA, followed by enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research applications and potential therapeutic purposes. One of the major hurdles that has only partially been overcome in vivo is efficient cellular uptake which is severely hampered by the rapid degradation and excretion of oligonucleotides. The generally accepted process of cellular uptake is by receptor-mediated endocytosis which is dependent on the temperature and concentration of the oligonucleotides in serum and extra vascular fluids.

Efforts aimed at improving the transmembrane delivery of nucleic acids and oligonucleotides have utilized protein carriers, antibody carriers, liposomal delivery systems, electroporation, direct injection, cell fusion, viral vectors, and calcium phosphate-mediated transformation. However, many of these techniques are limited by the types of cells in which transmembrane transport is enabled and by the conditions needed for achieving such transport. An alternative that is particularly attractive for the transmembrane delivery of oligonucleotides is modification of the physicochemical properties of oligonucleotides via conjugation to a molecule that facilitates transport. Another alternative is to increase the stability of oligonucleotides in serum, thereby increasing their concentration and distribution.

It has been previously reported that oligonucleotides modified with a 4-[(N-2-chloroethyl-N-methyl)amino] benzylamine reactive functionality at a 5'-phosphate position react with albumin and immunoglobulins M and G (Yu et al., *FEBS Letters*, 1994, 334:96–98). Binding to albumin was weak at about 20 µM with immunoglobulin binding stronger at about 4 to 6 µM. This study further reported that oligonucleotides conjugated to steroids had increased affinity for blood cells and thus changed their distribution and increased their lifetime in serum. One method for increasing membrane or cellular transport of oligonucleotides is the attachment of a pendant lipophilic group. Ramirez et al. (*J. Am. Chem. Soc.*, 1982, 104:5483) introduced the phospholipid group 5'-O-(1,2-di-O-myristoyl-sn-glycero-3-phosphoryl) into the dimer TpT independently at the 3' and 5' positions. Subsequently Shea et al. (*Nuc. Acids Res.*, 1990, 18:3777) disclosed oligonucleotides having a 1,2-di-O-hexyldecyl-rac-glycerol group linked to a 5'-phosphate on the 5'-terminus of the oligonucleotide. Certain of the Shea et al. authors also disclosed these and other compounds in patent application PCT/US90/01002. A further glucosyl phospholipid was disclosed by Guerra et al., *Tetrahedron Letters*, 1987, 28:3581.

In other work, a cholesteryl group was attached to the internucleotide linkage between the first and second nucleotides (from the 3' terminus) of an oligonucleotide. This work is disclosed in U.S. Pat. No. 4,958,013 and further in Letsinger et al., *Proc. Natl. Acad. Sci. USA*, 1989, 86:6553. Additional approaches to the delivery and study of oligonucleotides have involved the conjugation of a variety of other molecules and reporter groups. The aromatic intercalating agent anthraquinone was attached to the 2' position of a sugar fragment of an oligonucleotide as reported by Yamana et al. (*Bioconjugate Chem.*, 1990, 1:319), Lemairte et al. (*Proc. Natl. Acad. Sci. USA*, 1986, 84:648) and Leonetti et al. (*Bioconjugate Chem.*, 1990, 1:149).

Lysine and polylysines have also been conjugated to oligonucleotides to improve their charge-size characteristics. The poly(L-lysine) was linked to the oligonucleotide via periodate oxidation of the 3'-terminal ribose followed by reduction and coupling through a N-morpholine ring. Oligonucleotide-poly(L-lysine) conjugates are described in European Patent application 87109348.0. In this instance, the lysine residue was coupled to a 5' or 3' phosphate of the 5' or 3' terminal nucleotide of the oligonucleotide. A disulfide linkage has also been utilized at the 3' terminus of an oligonucleotide to link a peptide to the oligonucleotide. See, Corey and Schultz, *Science*, 1987, 238:1401; Zuckermann et al., *J. Am. Chem. Soc.*, 1988, 110:1614; and Corey et al., *J. Am. Chem. Soc.*, 1989, 111:8524.

A linking reagent for attaching biotin to the 3'-terminus of an oligonucleotide has also been described. Nelson et al., *Nuc. Acids Res.*, 1989, 17:7187. This reagent, N-Fmoc-O-DMT-3-amino-1,2-propanediol is now commercially available from Clontech Laboratories (Palo Alto, Calif.) under the name 3'-Amine on. It is also commercially available under the name 3'-Amino-Modifier reagent from Glen Research Corporation (Sterling, Va.). This reagent was also utilized to link a peptide to an oligonucleotide as reported by Judy et al. (*Tetrahedron Letters*, 1991, 32:879). A similar commercial reagent (actually a series of such linkers having various lengths of polymethylene connectors) for linking to the 5'-terminus of an oligonucleotide is 5'-Amino-Modifier C6. These reagents are available from Glen Research Corporation (Sterling, Va.). These compounds or similar ones were utilized by Krieg et al. (*Antisense Research and Development*, 1991, 1:161) to link fluorescein to the 5'-terminus of an oligonucleotide. Other compounds of interest have also been linked to the 3'-terminus of an oligonucleotide. Asseline et al. (*Proc. Natl. Acad. Sci. USA*, 1984, 81:3297) describe linking acridine on the 3'-terminal phosphate group of an poly (Tp) oligonucleotide via a polymethylene linkage. Haralambidis et al. (*Tetrahedron Letters*, 1987, 28:5199) report building a peptide on a solid state support and then linking an oligonucleotide to that peptide via the 3' hydroxyl group of the 3' terminal nucleotide of the oligonucleotide. Chollet (*Nucleosides & Nucleotides*, 1990, 9:957) attached an Aminolink 2 (Applied Biosystems, Foster City, Calif.) to the 5' terminal phosphate of an oligonucleotide. The bifunctional linking group SMPB (Pierce Chemical Co., Rockford, Ill.) was then used to link an interleukin protein to the oligonucleotide.

Conjugation of lipids, reporters, peptides and other molecules to oligonucleotides is not limited to the terminal 3' and 5'-positions. A wide variety of conjugates have also been reported in the literature wherein attachment is performed at any one or more of the 2'-positions on the nucleotide building blocks of the oligonucleotide. Further conjugates have also been reported wherein attachment occurs on the internucleotide linkage or on one of the atoms of the nucleobase of any one of the nucleotide units of the oligonucleotide. For example, an EDTA iron complex has been linked to the 5 position of a pyrimidine nucleoside as reported by Dreyer and Dervan (*Proc. Natl. Acad. Sci. USA*, 1985, 82:968). Fluorescein has been linked to an oligonucleotide in the same manner as reported by Haralambidis et al. (*Nucleic Acid Research*, 1987, 15:4857) and biotin in the same manner as described in PCT application PCT/US/02198. Fluorescein, biotin and pyrene were also linked in the same manner as reported by Telser et al. (*J. Am. Chem. Soc.*, 1989, 111:6966). A commercial reagent, Amino-Modifier-dT, from Glen Research Corporation (Sterling, Va.) can be utilized to introduce pyrimidine nucleotides bearing similar linking groups into oligonucleotides.

Manoharan et al. (PCT Application WO 93/07883) have also reported the conjugation of oligonucleotides with a variety of molecules such as steroids, reporter molecules, reporter enzymes, vitamins, non-aromatic lipophilic molecules, chelators, porphyrins, intercalators, peptides and proteins through the intermediacy of varied linking groups, such as 6-aminoalkoxy and 6-aminoalkylamino groups. Conjugation has been reported at the 3'-, 5'-, 2'-, internucleotide linkage and nucleobase positions of oligonucleotides. Such oligonucleotide conjugates are expected to have improved physicochemical properties that facilitated their uptake and delivery into cells as demonstrated by in vitro experiments. The intracellular and intranuclear delivery of nucleic acids and oligonucleotides, however, is still a challenge. Most often, penetration of heretofore reported oligonucleotide conjugates has been found to be limited. This has typically been a problem because such conjugates have generally been designed to improve the passive absorption of the oligonucleotides where the size, physicochemical properties and extracellular concentration of the conjugate play important limiting roles. This coupled with the limited extracellular stability of nucleic acids and oligonucleotides demands the development of novel conjugates that will deliver higher levels of nucleic acids and oligonucleotides into specific tissues and targeted cells.

Albumin is the most abundant protein in mammalian systems, and plays an important role in the transport and deposition of drug substances in blood. It is generally accepted that there are two major specific drug binding sites, site I and site II on human albumin. X-ray studies of crystalline human albumin (He and Carter, *Nature*, 1992, 358:209–215) indicate that site I and site II are located within specialized cavities in subdomain IIA and IIIA, respectively.

Interaction of oligonucleotides with proteins play an important role in absorption, distribution and pharmacokinetics. In the bloodstream, the major oligonucleotide binding protiens are immunoglobulins M and G, serum albumin, and orosomucoid α-1-acid glycoprotein (AAG). The role of plasma protein binding is an important factor in oligonucleotide disposition and efficacy. If protein binding of oligonucleotides can be modulated with small molecular conjugation, it will result in more efficacious oligonucleotide drugs.

Albumin is a water-soluble protein with a molecular weight of 66,500 comprising a single chain of 585 amino acids containing a single tryptophan (Trp-214), low (2%) glycine content, high cystine content and a large number of charged amino acids (about 100 negative charges and 100 positive charges) and has an isoelectric point of about pH 5.0. Thus, at a plasma pH of 7.4, it has a net negative charge of –15. Nonetheless, it attracts both anions and cations. It circulates at a concentration of 3.5–5 g/100 mL in blood plasma and also exists at lower concentrations in extravascular fluids. About 60% of all human serum albumin (HSA) is located in the extravascular space (Peters, *Adv. Protein Chem.*, 1985, 37:161). As the most abundant protein in plasma, HSA plays an important role in the maintenance of blood pH and colloidal osmotic pressure and accounts for most of the thiol content of plasma (Cys-34). Binding of drugs to albumin is usually rapidly reversible. The binding (association) constants are typically in the range of $10^4$ to $10^6$ $M^{-1}$. HSA is organized in a series of three repeating domains (I, II and III) each having two subdomains. Ligands bind to HSA generally to one or both of two binding sites. Site I is associated with the ligands warfarin, phenyl butazone. This site is localized in subdomain IIA. Site II is in subdomain IIIA and binds to diazepam and ibuprofen. Other ibuprofen analogs suprofen, pranoprofen, carprofen, fenbufen and ketoprofen, which are all non-steroidal antiinflammatory agents bind to site II. Flufenamic acid and dansylsarcosine bind to site II while dansylamide bind to site I. Barbiturates such as quinalbarbitone interact with site II and the antidiabetic tolbutamide binds to site I, site II and an unidentified site. (R)-Folinic acid binds to both sites. Other compounds that bind to HSA include thiadiazides, diazepines, and antibacterials (e.g., nalidixic acid).

Lipoproteins can contribute to the plasma binding of lipophilic drugs and dissolve in lipid core of the lipoproteins. Cholesterol conjugated oligonucleotides are known to bind to serum proteins. Agrawal et al., ("Effect of aspirin on protein binding and tissue disposition of oligonucleotide phosphorothioate in rats," *Journal of Drug Targeting*, 1998, 5:303–313) describe the effect of co-administration of aspirin at a concentration of 2 mg/mL and demonstrate that the P=S oligonucleotide binding to serum albumin is reduced (as measured by % protein bound of P=S oligonucleotide). This result indicates that presence of aspirin in the body or similar small molecule drugs could effectively alter protein binding of P=S oligonucleotides in vivo.

Pharmacokinetic studies of P=S oligonucleotide (GEM-91, 25-mer phosphorothioate oligonucleotide) in rats were determined after bolus injection. One hour before administration of the drug, aspirin is administered by gavage. When P=S oligonucleotide was administered following aspirin administration in rats the following the plasma pharmacokinetic parameters ($t_{1/2}$ α, $t_{1/2}$ β, AUC, etc.) were lower. The tissue disposition was significantly different in that the majority of tissues. e.g. kidney, liver, spleen, bone marrow, skin, thyroid, adrenal, heart, lung, and pancreas, had lower concentrations, and gastrointestinal tissues and contents had a higher concentration. In certain tissues, e.g. liver and bone marrow, the concentration of P=S oligonucleotide which was administered following aspirin administration was about half of that observed following administration of P=S oligonucleotide alone. It was seen that the rate of elimination was affected in animals compared to rats receiving P=S oligonucleotide alone. A higher concentration of excreted oligonucleotide in feces from rats receiving P=S oligonucleotide following aspirin was observed compared to rats receiving P=S oligonucleotide alone. However, the effect of attaching small molecule drugs to the oligonucleotide to modulate serum albumin binding has not been studied.

Therefore, there is a clear need for oligonucleotide conjugates having improved distribution and cellular uptake and methods for their preparation, that address the shortcomings of oligonucleotide conjugates as described above. The present invention is directed to this very important end.

SUMMARY OF THE INVENTION

The present invention provides ligand conjugated oligomeric compounds that are capable of interacting with a protein. In particular, the ligand conjugated oligomeric compounds of the present invention bind to proteins. More particularly, the present invention provides oligomeric compounds that are conjugated to drug moieties.

The oligomeric compounds of the present invention bind to serum, vascular and cellular proteins. It is preferred that the serum proteins include albumin, an immunoglobulin, a lipoprotein, α-2-macroglobulin and α-1-glycoprotein.

The present invention also provides ligand conjugated oligomeric compounds wherein the oligomeric compound is an oligonucleotide comprising a plurality of nucleosides. Also provided are oligonucleotides wherein the nucleosides are connected by phosphodiester linkages. Further, oligonucleotides wherein the nucleosides are connected by phosphorothioate linkages are also provided. It is preferred that at least one of the nucleosides of the oligonucleotides of the present invention bear a 2'-substituent group.

The present invention also provides methods for increasing the concentration of an oligonucleotide in serum comprising the steps of:

(a) selecting a drug moiety that is known to bind to a serum protein;

(b) conjugating said drug moiety to said oligonucleotide to form a conjugated oligonucleotide; and (c) adding said conjugated oligonucleotide to said serum.

The present invention further provides methods for increasing the capacity of serum for an oligonucleotide comprising the steps of:

(a) selecting a drug moiety that is known to bind to a serum protein;

(b) conjugating said drug moiety to said oligonucleotide to form a conjugated oligonucleotide; and (c) adding said conjugated oligonucleotide to said serum.

In one embodiment of the present invention the serum protein is a protein having a binding site for the drug moiety. In another embodiment the serum protein is a protein having a binding site for the oligonucleotide. In yet another embodiment the serum protein is a protein having a binding site for the oligonucleotide and a binding site for the drug moiety such that the binding site for the oligonucleotide is distinct from the binding site for the drug moiety.

The present invention further provides methods for increasing the binding of an oligonucleotide to a portion of the vascular system comprising the steps of:

(a) selecting a drug moiety that is known to bind to a protein that resides, in part, in the circulating serum and, in part, in a non-circulating portion of the vascular system;

(b) conjugating said drug moiety to said oligonucleotide to form a conjugated oligonucleotide; and (c) adding said conjugated oligonucleotide to said vascular system.

The present invention also provides methods for promoting cellular uptake of an oligonucleotide in a cell comprising the steps of:

(a) selecting a protein that resides on the cellular membrane and extends, at least in part, on the external side of said membrane;

(b) selecting a drug moiety that is known to bind to said protein;

(c) conjugating said drug moiety to said oligonucleotide to form a conjugated oligonucleotide; and (d) exposing said cell to said conjugated oligonucleotide.

Preferably, the protein residing on the cellular membrane is a cell surface integrin.

In one embodiment of the present invention the serum protein is albumin, an immunoglobulin, α-2-macroglobulin, α-1-glycoprotein or a lipoprotein. Preferably, the serum protein is albumin.

In yet another embodiment of the present invention the drug moiety is aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Preferably, the drug moiety is aspirin, phenylbutazone, ibuprofen, suprofen, fenbufen, ketoprofen, (S)-(+)-pranoprofen, palmityl or carprofen. More preferably, the drug moiety is ibuprofen.

DETAILED DESCRIPTION OF PREFERRED EMBODIMENTS

Figure 1:
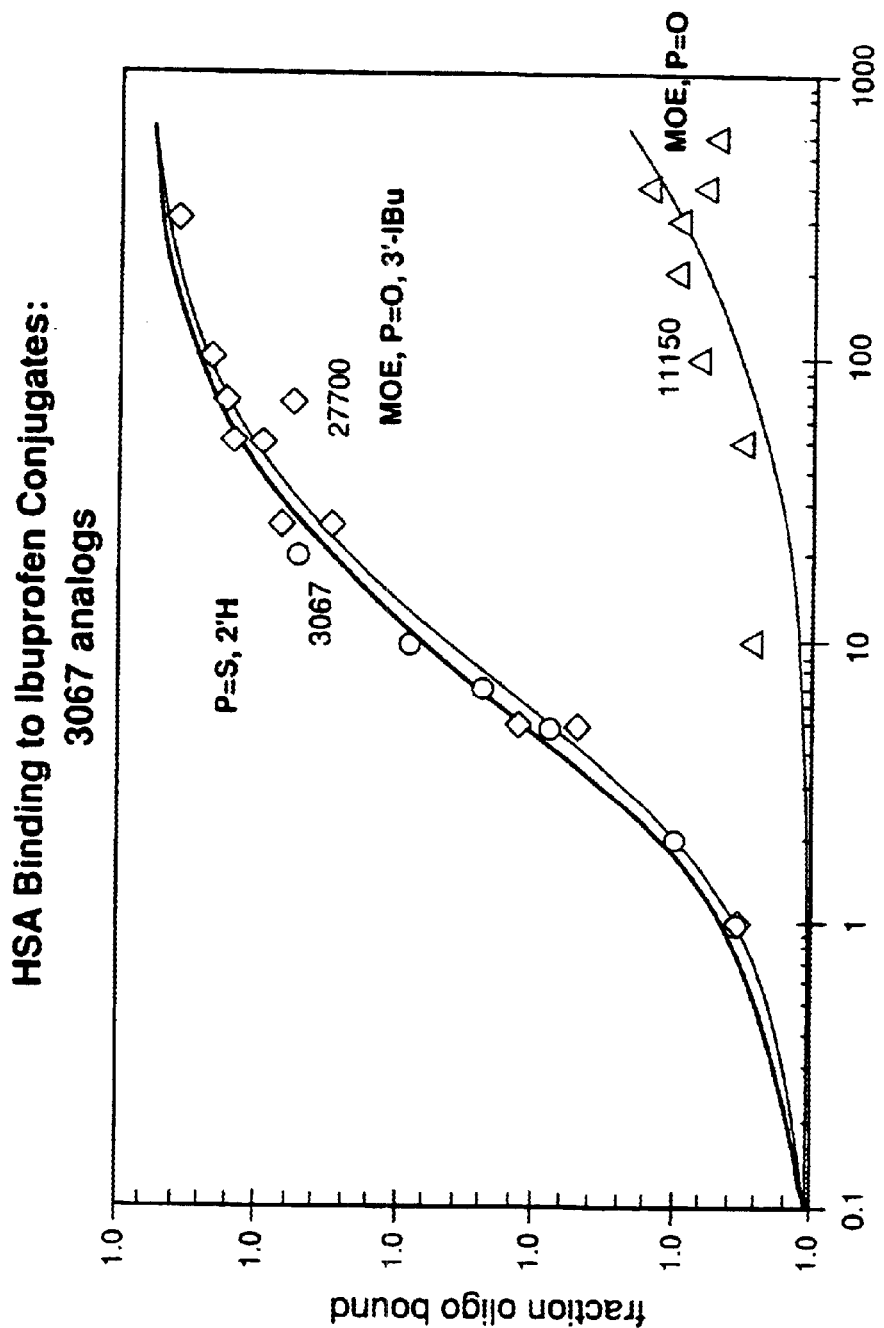
FIG. 1 is a graph showing a comparison of HSA binding (Sigma A3782 lot 94H9318) for ibuprofen conjugates (diamonds) to unconjugated controls (triangles). Binding curve for the phosphorothioate DNA analogs of each sequence are also shown (circles). Oligonucleotide (50 nM) was incubated with increasing concentrations of HSA as described in the text.

The present invention provides methods of improving the pharmacokinetic properties of oligonucleotides. The invention further provides ligand conjugated oligomeric compounds having improved pharmacokinetic properties and methods for their preparation. Such oligomeric compounds are prepared having covalently attached ligands that bind reversibly to one or more serum, vascular or cellular proteins. This reversible binding is expected to decrease urinary excretion, increase serum half life and greatly increase the distribution of oligomeric compounds thus conjugated. The binding of particular drugs to plasma protein has been previously shown to enhance the disposition and efficacy of drugs (Herve et al., *Clin. Pharmacokinet.*, 1994, 26:44).

The therapeutic effect of an antisense oligonucleotide is realized when it interacts with a specific cellular nucleic acid and effectively negates its function. A preferred target is mRNA encoding a protein that is responsible for a disease state. To reach a target nucleic acid after administration, an antisense agent should be able to overcome inherent factors such as rapid degradation in serum, short half life in serum and rapid filtration by the kidneys with subsequent excretion in the urine. Oligonucleotides that overcome these inherent factors have increased serum half lives, distribution, cellular uptake and hence improved efficacy. These enhanced pharmacokinetic parameters have been shown for selected drug molecules that bind plasma proteins (Olson and Christ, *Annual Reports in Medicinal Chemistry*, 1996, 31:327). Two proteins that have been studied more than most are human serum albumin (HSA) and α-1-acid glycoprotein. HSA binds a variety of endogenous and exogenous ligands with association constants typically in the range of $10^4$ to $10^6$ $M^{-1}$. Association constants for ligands with α-1-acid glycoprotein are similar to those for HSA.

At least for therapeutic purposes, antisense oligonucleotides should have a degree of stability in serum to allow distribution and cellular uptake. The prolonged maintenance of therapeutic levels of antisense agents in serum will have a significant effect on the distribution and cellular uptake and unlike conjugate groups that target specific cell receptors the increased serum stability will effect all cells. Numerous efforts have focused on increasing the cellular uptake of oligonucleotides including increasing the membrane permeability via conjugates and cellular delivery of oligonucleotides.

Many drugs reversibly bind to plasma proteins. A representative list, which is not meant to be inclusive, includes: aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, benzothiadiazides, chlorothiazide, diazepines (such as for example fludiazepam and diazepam) indomethicin, barbiturates (such as for example quinalbarbitone), cephalosporins, sulfa drugs, antidiabetics (such as for example tollbutamide), antibacterials (such as for example a group of quinolones; nalidixic acid and cinoxacin) and several antibiotics. Serum albumin is the most important protein among all plasma proteins for drug binding, although binding to other proteins (for example, macroglobulin $G_2$, immunoglobulins, lipoproteins, alpha-1-acid glycoprotein, thrombin) is also important.

Ligands that bind serum, vascular or cellular proteins may be attached via an optional linking moiety to one or more sites on an oligonucleotide of the invention. These sites include one or more of, but are not limited to, the 2'-position, 3'-position, 5'-position, the internucleotide linkage, and a nucleobase atom of any nucleotide residue. The attachment of ligands to such structures can be performed, according to some preferred embodiments of the invention, using a linking group, or without the use of such a linking group.

In some preferred embodiments of the invention, one or more protein binding ligands are attached to an oligonucleotide via linking groups, to form a ligand conjugated oligonucleotide. Preferred linking groups of the invention include, but are not limited to, 6-aminoalkoxy linkers, 6-aminoalkylamino linkers, cysteamine, heterobifunctional linkers, homobifunctional linkers, and a universal linker (derived from 3-dimethoxytrityloxy-2-aminopropanol). A particularly preferred linking group for the synthesis of ligand conjugated oligonucleotides of the invention is a 6-aminohexyloxy group. A variety of heterobifunctional and homobifunctional linking moieties are available from Pierce Co. (Rockford, Ill.). Such heterobifunctional and homobifunctional linking moieties are particularly useful in conjunction with the 6-aminoalkoxy and 6-aminoalkylamino moieties to form extended linkers useful for linking ligands to a nucleoside. Further useful linking groups that are commercially available are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, while the 3'-Amino-Modifier is also available from Clontech Laboratories Inc. (Palo Alto, Calif.). In addition, a nucleotide analog bearing a linking group pre-attached to the nucleoside is commercially available from Glen Research Corporation under the tradename "Amino-Modifier-dT." This nucleoside-linking group reagent, a uridine derivative having an [N(7-trifluoroacetylaminoheptyl)3-acrylamido] substituent group at the 5 position of the pyrimidine ring, is synthesized as per the procedure of Jablonski et al. (*Nucleic Acid Research*, 1986, 14:6115). The present invention also includes as nucleoside analogs adenine nucleosides functionalized to include a linker on the N6 purine amino group, guanine nucleosides functionalized to include a linker at the exocyclic N2 purine amino group, and cytosine nucleosides functionalized to include a linker on either the N4 pyrimidine amino group or the 5 pyrimidine position. Such nucleoside analogs are incorporated into oligonucleotides with a ligand attached to the linker either pre- or post-oligomerization.

In a preferred embodiment of the present invention ligand molecules are selected for conjugation to oligonucleotides on the basis of their affinity for one or more proteins. These proteins may be serum, vascular or cellular proteins. Serum proteins are proteins that are present in the fluid portion of the blood, obtained after coagulation and removal of the fibrin clot and blood cells, as distinguished from the plasma in circulating blood. Vascular proteins are proteins that are present in portions of the vascular system relating to or containing blood vessels. Cellular proteins are membrane proteins which have at least a portion of the protein extending extracellularly and assisting in the process of endocytosis.

Many ligands having an affinity for proteins are well documented in the literature and are amenable to the present invention. A preferred group of ligands are small molecules including drug moieties. According to the present invention, drug moieties include, but are not limited to, warfarin and coumarins including substituted coumarins, isocoumarin derivatives, 7-anilinocoumarin-4-acetic acid, profens including ibuprofen, enantiomers of ibuprofen (r-ibuprofen and s,-ibuprofen), ibuprofen analogs, ketoprofen, carprofen, etodolac, suprofen, indoprofen, fenbufen, arylpropionic acids, arylalkanoic acids, 2-aryl-2-fluoropropionic acids, glibenclamide, acetohexamide, arylalkanoic acids, tolbutamide, gliclazide, metformin, curcumin, digitoxin, digoxin, diazepam, benzothiadiazides, chlorothiazide, diazepines, benzodiazepines, naproxen, phenyl butazone, oxyphenbutazone, dansyl amide, dansylsarcosine, 2,3,5-triiodobenzoic acid, palmitic acid, aspirin, salicylates, substituted salicylates, penicillin, flurbiprofen, pirprofin, oxaprozin, flufenamic acid, deoxycholic acid, glycyrrhizin, azathioprine, butibufen, ibufenac, 5-fluoro-1-typtaphan, 5-fluoro-salicylic, acidazapropanazone, mefenamic acid, indomethacin, flufenamic acid, bilirubin, ibuprofen, lysine complexes, diphenyl, hydantoin, valproic acid, tolmetin, barbiturates (such as, for example, quinalbarbitone), cephalosporins, sulfa drugs, antidiabetics (such as, for example, tollbutamide), antibacterials (such as, for example, quinolones, nalidixic acid and cinoxacin) and several antibiotics.

In one embodiment of the present invention the drug moiety bears a carboxylic acid group. In another embodiment of the present invention the drug moiety is a propionic acid derivative.

In another preferred embodiment, the drug moiety is an arylpropionic acid of the formula:

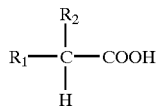

wherein:
one of $R_1$ and $R_2$ is $C_1$ to $C_{12}$ alkyl and the other of $R_1$ and $R_2$ is aryl; or
both $R_1$ and $R_2$ are $C_1$ to $C_{12}$ alkyl; or
both $R_1$ and $R_2$ are aryl.

In preferred embodiments, the aryl group may be substituted or unsubstituted benzyl, phenyl, xylyl, naphthyl, toluyl, pyrenyl, anthracyl, phenanthryl, azulyl, phenethyl, cinnamyl, benzhydryl, and mesityl wherein said substituents are hydroxyl, alkyl, alkoxy, alcohol, benzyl, phenyl, nitro, thiol, thioalkoxy, halogen, or alkyl, substituted alkyl, aryl, alkenyl, or alkynyl groups.

In one preferred embodiment of the invention the protein targeted by a ligand conjugated oligomeric compound is a serum protein. It is preferred that the serum protein targeted by a conjugated oligomeric compound is an immunoglobulin (an antibody). Preferred immunoglobulins are immunoglobulin G and immunoglobulin M. Immunoglobulins are known to appear in blood serum and tissues of vertebrate animals.

In another embodiment of the invention the serum protein targeted by a conjugated oligomeric compound is a lipoprotein. Lipoproteins are blood proteins having molecular weights generally above 20,000 that carry lipids and are recognized by specific cell surface receptors. The association with lipoproteins in the serum will initially increase pharmacokinetic parameters such as half life and distribution. A secondary consideration is the ability of lipoproteins to enhance cellular uptake via receptor-mediated endocytosis.

In yet another embodiment the serum protein targeted by a ligand conjugated oligomeric compound is α-2-macroglobulin. In yet a further embodiment the serum protein targeted by a ligand conjugated oligomeric compound is α-1-glycoprotein.

As used herein, the term "protected" means that the indicated moiety has a protecting group appended thereon. In some preferred embodiments of the invention compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron*, 1992, 48:2223–2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991, each of which is hereby incorporated by reference in its entirety.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p.1) and various substituted sulfonylethyl carbamates exemplified by the Nsc group (Samukov et al., *Tetrahedron Lett*, 1994, 35:7821; Verhart and Tesser, *Rec. Trav. Chim. Pays-Bas*, 1987, 107:621).

Additional amino-protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl. Equivalents of these amino-protecting groups are also encompassed by the compounds and methods of the present invention.

In a preferred embodiment of the present invention oligonucleotides are provided including a number of linked nucleosides wherein at least one of the nucleosides is a 2'-functionalized nucleoside having a ligand molecule linked to the 2'-position of the nucleoside; a heterocyclic base functionalized nucleoside having a ligand molecule linked to the heterocyclic base of the nucleoside, a 5' terminal nucleoside having a ligand molecule linked to the 5'-position of the nucleoside, a 3' terminal nucleoside having a ligand molecule linked to the 3'-position of the nucleoside, or an inter-strand nucleoside having a ligand molecule linked to an inter-stand linkage linking said inter-strand nucleoside to an adjacent nucleoside.

Ligand conjugated oligonucleotides of the invention may be synthesized by the use of an oligonucleotide that bears a pendant reactive functionality such as that derived from the attachment of a linking molecule onto the oligonucleotide. This reactive oligonucleotide may be reacted directly with commercially available ligands, ligands that are synthesized bearing a variety of protecting groups, or ligands that have a linking moiety attached thereto. The methods of the present invention facilitate the synthesis of ligand conjugated oligonucleotides by the use of, in some preferred embodiments, nucleoside monomers that have been appropriately conjugated with ligands and that may further be attached to a solid support material. Such ligand-nucleoside conjugates optionally attached to a solid support material are prepared according to some preferred embodiments of the methods of the present invention via reaction of a selected serum binding ligand with a linking moiety located on a 2', 3', or 5' position of a nucleoside or oligonucleotide.

The present invention provides methods for increasing the concentration of an oligonucleotide in serum. According to such methods, a drug moiety that is known to bind to a serum protein is selected and conjugated to an oligonucleotide, thus forming a conjugated oligonucleotide. This conjugated oligonucleotide is then added to the serum.

The present invention further provides methods for increasing the capacity of serum for an oligonucleotide. According to such methods, a drug moiety that is known to bind to a serum protein is selected and conjugated to an oligonucleotide, thus forming a conjugated oligonucleotide. This conjugated oligonucleotide is then added to the serum.

The present invention also provides methods for increasing the binding of an oligonucleotide to a portion of the vascular system. According to such methods, a drug moiety that is known to bind to a vascular protein is selected. The vascular protein selected is a protein which resides, in part, in the circulating serum and, in part, in the non-circulating portion of the vascular system. This drug moiety is conjugated to an oligonucleotide to form a conjugated oligonucleotide, which is then added to the vascular system.

The present invention further provides methods for promoting the cellular uptake of an oligonucleotide in a cell. According to such methods, a cellular protein is selected. This cellular protein is a protein that resides on the cellular membrane and extends, in part, extracellularly so that part of this cellular protein extends onto the external side of the cellular membrane. Next, a drug moiety that is known to bind to the cellular protein is selected and conjugated to an oligonucleotide to form a conjugated oligonucleotide. This conjugated oligonucleotide is then brought into contact with cells in which cellular uptake of the oligonucleotide is to be promoted.

The present invention also provides methods of increasing cellular uptake of an oligonucleotide comprising contacting an organism with an oligonucleotide of the invention, said oligonucleotide being conjugated to a ligand.

Ligand conjugated oligomeric compounds of the present invention can be included in compositions that further include one or more inert carrier compounds.

Antisense therapeutics can be practiced in a plethora of various organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to antisense therapeutics and/or prophylactics. Seemingly diverse organisms such as bacteria, yeast, protozoa, algae, all plant and all higher animal forms, including warm-blooded animals, can be treated by antisense therapy. Further, since each of the cells of multicellular eukaryotes also includes both DNA-RNA transcription and RNA-protein translation as an integral part of its cellular activity, antisense therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations or organelles can also be included within the definition of organisms that are capable of being treated with antisense therapeutics or diagnostics. As used herein, therapeutics is meant to include both the eradication of a disease state, killing of an organism, e.g. bacterial, protozoan or other infection, or control of erratic or harmful cellular growth or expression.

In a preferred embodiment of the present invention a ligand having an affinity for a serum protein is attached to at least one nucleoside in an antisense diagnostic or therapeutic agent to enhance the pharmacokinetic properties of the antisense therapeutic or diagnostic agent. Such improved pharmacokinetic properties include, but are not limited to, increased binding of the antisense compound to serum proteins, increased plasma concentration of the antisense compound, increased tissue distribution, increased capacity of binding of the antisense compound to serum proteins and increased half-lives. Such an antisense diagnostic or therapeutic agent is preferably a nucleic acid or oligonucleotide formed of a plurality of linked nucleosides of a sequence that are "antisense" to a region of an RNA or DNA of interest. The nucleosides are linked by phosphorus-containing or non-phosphorus-containing covalent internucleoside linkages. One or more nucleosides of the oligonucleotide are conjugated to include a ligand molecule bound to the nucleoside with or without a linking group. For the purposes of identification, such conjugated nucleosides can be characterized as ligand bearing nucleosides or ligand-nucleoside conjugates. The linked nucleosides having at least one conjugated nucleoside within their sequence will demonstrate enhanced antisense activity when compared to like linked nucleoside or oligonucleotides of the same sequence that are not conjugated.

The ligand conjugated oligonucleotides of the present invention also include conjugates of oligonucleotides and linked nucleosides wherein the ligand is attached directly onto the nucleoside or nucleotide without the intermediacy of a linker group. This attachment of ligand may be performed at either one or more of the 2'-, 3'-, 5'-, nucleobase or internucleoside linkage positions of the oligonucleotide or linked nucleosides of the invention. Ligands may preferably be attached, via linking groups, at a carboxyl, amino or oxo groups of the ligand. Typical linking groups may be ester, amide or carbamate groups.

In the context of this invention, the terms "oligomer" and "oligomeric compound" refer not only to a plurality of naturally-occurring or non-naturally-occurring nucleosides joined together in a specific sequence but are further inclusive of all types of oligomeric compounds currently known in the art such as oligonucleotide analogs, peptide nucleic acids and locked nucleic acids where the sugar is involved in locking the conformation. Many diverse motifs are currently known for improving the desired effect for the specific target that the oligomeric compound is aimed at such as for example chimeric oligomeric compounds where there are more than one type of internucleoside linkages dividing the oligomeric compound into regions. Oligomeric compounds are typically structurally distinguishable from, yet functionally interchangeable with, naturally-occurring or synthetic wild-type oligonucleotides. Thus, oligomeric compounds include all such structures which function effectively to mimic the structure and/or function of a desired RNA or DNA strand, for example, by hybridizing to a target. Whereas the term "oligonucleotide" has a well defined meaning in the art, the term "oligomeric compound" or "oligomer" is intended to be broader, inclusive of oligomers having all manner of modifications known in the art. Gapped or chimeric compounds are disclosed in for example, U.S. Pat. No. 5,623,065, issued Apr. 22, 1997, the contents of which are incorporated herein by reference.

In the context of this invention, the term "oligomeric compound" includes linked nucleosides having phosphorus and non-phosphorus linkages and mixed backbone oligomers. A representative list of phosphorus containing and non-phosphorus containing linkages amenable to the present invention includes:

phosphorus containing linkages
  phosphorodithioate (—O—P(S)(S)—O—);
  phosphorothioate (—O—P(S)(O)—O—);
  phosphoramidate (—O—P(O)(NJ)—O—);
  phosphonate (—O—P(J)(O)—O—);
  phosphotriesters (—O—P(OJ)(O)—O—);
  phophosphoramidate (—O—P(O)(NJ)—S—);
  thionoalkylphosphonate (—O—P(S)(J)—O—);
  thionoalkylphosphotriester (—O—P(O)(OJ)—S—);
  boranophosphate (—R$^5$—P(O)(O)—J—);
non-phosphorus containing linkages
  thiodiester (—O—C(O)—S—);
  thionocarbamate (—O—C(O)(NJ)—S—);
  siloxane (—O—Si(J)$_2$—O—);
  carbamate (—O—C(O)—NH— and —NH—C(O)—O—)
  sulfamate (—O—S(O)(O)—N— and —N—S(O)(O)—N—;
  morpholino sulfamide (—O—S(O)(N(morpholino)-);
  sulfonamide (—O—SO$_2$—NH—);
  sulfide (—CH$_2$—S—CH$_2$—);
  sulfonate (—O—SO$_2$—CH$_2$—);
  N,N'-dimethylhydrazine (—CH$_2$—N(CH$_3$)—N(CH$_3$)—)
  thioformacetal (—S—CH$_2$—O—);
  formacetal (—O—CH$_2$—O—);
  thioketal (—S—C(J)$_2$—O—); and
  ketal (—O—C(J)$_2$—O—);
  amine (—NH—CH$_2$—CH$_2$—);
  hydroxylamine (—CH$_2$—N(J)—O—);
  hydroxylimine (—CH=N—O—); and
  hydrazinyl (—CH$_2$—N(H)—N(H)—).
    where "J" denotes a substituent group which is commonly hydrogen or an alkyl group or a more complicated group that varies from one type of linkage to another.

In addition to linking groups as described above that involve the modification or substitution of the —O—P—O— atoms of a naturally occurring linkage, included within the scope of the present invention are linking groups that include modification of the 5'-methylene group as well as one or more of the —O—P—O— atoms. Linkages of this type are well documented in the prior art and include without limitation the following:

amides (—CH$_2$—CH$_2$—N(H)—C(O)) and —CH$_2$—O—N=CH—; and
alkylphosphorus (—C(J)$_2$—P(=O)(OJ)—C(J)$_2$—C(J)$_2$—).
    wherein J is as described above.

Synthetic schemes for the synthesis of the substitute internucleoside linkages described above are disclosed in: WO 91/08213; WO 90/15065; WO 91/15500; WO 92/20822; WO 92/20823; WO 91/15500; WO 89/12060; EP 216860; PCT/US 92/04294; PCT/US 90/03138; PCT/US 91/06855; PCT/US 92/03385; PCT/US 91/03680; U.S. application Ser. Nos. 07/990,848; 07/892,902; 07/806,710; 07/763,130; 07/690,786; U.S. Pat. Nos. 5,466,677; 5,034,506; 5,124,047; 5,278,302; 5,321,131; 5,519,126; 4,469,863; 5,455,233; 5,214,134; 5,470,967; 5,434,257; Stirchak, E. P., et al., *Nucleic Acid Res.*, 1989, 17, 6129–6141; Hewitt, J. M., et al., 1992, 11, 1661–1666; Sood, A., et al., *J. Am. Chem. Soc.*, 1990, 112, 9000–9001; Vaseur, J. J. et al., *J. Amer. Chem. Soc.*, 1992, 114, 4006–4007; Musichi, B., et al., *J. Org. Chem.*, 1990, 55, 4231–4233; Reynolds, R. C., et al., *J. Org. Chem.*, 1992, 57, 2983–2985; Mertes, M. P., et al., *J. Med. Chem.*, 1969, 12, 154–157; Mungall, W. S., et al., *J. Org. Chem.*, 1977, 42, 703–706; Stirchak, E. P., et al., *J. Org. Chem.*, 1987, 52, 4202–4206; Coull, J. M., et al., *Tet. Lett.*, 1987, 28, 745; and Wang, H., et al. , *Tet. Lett.*, 1991, 32, 7385–7388.

Other modifications can be made to the sugar, to the base, or to the phosphate group of the nucleotide. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. No. 5,138,045, 5,218,105, 5,223,618 5,359,044, 5,378,825, 5,386,023, 5,457,191, 5,459,255, 5,489,677, 5,506,351, 5,541,307, 5,543,507, 5,571,902, 5,578,718, 5,587,361, 5,587,469, all assigned to the assignee of this application. The disclosures of each of the above referenced publications are herein incorporated by reference.

Another modification that is used to prepare oligomeric compounds amenable to the present invention includes LNA's (locked nucleic acid) which are novel conformationally restricted oligonucleotide analogs containing 2'-O,4'-C-methylene LNA nucleoside monomers. LNA and LNA analogs display very high duplex thermal stabilities with complementary DNA and RNA (Tm=+3 to +10 C), stability towards 3'-exonucleolytic degradation, and good solubility properties (see for example:

LNA (locked nucleic acids, synthesis and high-affinity nucleic acid recognition, Singh et al., Dep. Chem., Univ. Copenhagen, Copenhagen, Den. Chem. Commun., (Cambridge) (1998), (4), 455–456. A novel class of nucleic acid analogs, termed LNA (locked nucleic acids), is introduced. Following the Watson-Crick base pairing rules, LNA forms duplexes with complementary DNA and RNA with remarkably increased thermal stabilities and generally improved selectivity.

Synthesis of the adenine, cytosine, guanine, 5-methylcytosine, thymine and uracil bicyclonucleoside monomers, oligomerization, and nucleic acid recognition properties have been described (see Koshkin et al., Department of Chemistry, University of Copenhagen, Copenhagen, Den. Tetrahedron (1998), 54(14), 3607–3630. LNA monomers, have been synthesized and their nucleic acid recognition potential evaluated for six different nucleobases, namely adenine, cytosine, guanine, 5-methylcytosine, thymine and uracil. Studies of mis-matched sequences show that LNA obey the Watson-Crick base pairing rules with generally improved selectivity compared to the corresponding unmodified reference strands.

Potent and nontoxic antisense oligonucleotides containing locked nucleic acids have been described (Wahlestedt et al., Center for Genomics Research, Karolinska Institutet, Stockholm, Swed., Proc. Natl. Acad. Sci. U.S.A. (2000), 97(10), 5633–5638.) The authors have demonstrated locked nucleic acid (LNA), confers several desired properties to antisense agents. LNA/DNA copolymers were not degraded readily in blood serum and cell extracts. LNA/DNA copolymers exhibited potent antisense activity on assay systems as disparate as a G-protein-coupled receptor in living rat brain and an *Escherichia coli* reporter gene.

The conformations of locked nucleic acids (LNA) has been determined by Petersen et al., Department of Chemistry, University of Southern Denmark, Odense University, Odense, Den., J. Mol. Recognit., (2000), 13(1), 44–53. The authors have used 2D NMR spectroscopy to show that the locked conformation of the LNA nucleotides both in ssLNA and in the duplexes organize the phosphate backbone in such a way as to introduce higher population of the N-type conformation. These conformational changes are associated with an improved stacking of the nucleobases.

LNA properties have been described by Wengel et al., Center For Synthetic Bioorganic Chemistry, Department of Chemistry, University of Copenhagen, Copenhagen, Den. Nucleosides Nucleotides (1999), 18(6 & 7), 1365–1370.

LNA forms duplexes with complementary DNA, RNA or LNA with high thermal affinities. CD spectra show that duplexes involving fully modified LNA (esp. LNA:RNA) structurally resemble an A-form RNA:RNA duplex. NMR examination of an LNA:DNA duplex confirm the 3'-endo conformation of an LNA monomer. Recognition of double-stranded DNA is demonstrated suggesting strand invasion by LNA. Lipofectin-mediated efficient delivery of LNA into living human breast cancer cells has been accomplished.

In a patent application, preparation of locked nucleoside analogs-containing oligodeoxyribonucleotide duplexes as substrates for nucleic acid polymerases has been described Wengel, Jesper; Nielsen, Poul. (Exiqon A/S, Den.). PCT Int. Appl. (1999), 269 pp Patent written in English. Application: WO 98-DK393 19980914. Priority: DK 97-1054 19970912; DK 97-1492 19971219; DK 98-61 19980116; DK 98-286 19980303; DK 98-585 19980429; US 98-88309 19980605. CAN 130:252609 AN 1999:216926

Bicyclic and tricyclic nucleoside and nucleotide analogs were prepared as well as oligodeoxyribonucleotides comprising such elements I (B is selected from hydrogen, hydroxy, alkoxy, alkyl, acyloxy, nucleobases, DNA intercalators; P designates the radical position for an internucleoside linkage to a succeeding monomer, or a 5'-terminal group, such internucleoside linkage or 5'-terminal group optionally including the substituent R5; X is selected from O, S, substituted N, substituted C; R1, R1*, R2, R2*, R3, R3*, R4*, R5, R5*, are biradical(s), independently selected from hydrogen, alkyl, alkenyl, alkynyl, hydroxy, alkoxy, alkenyloxy, carboxy, alkoxycarbonyl, alkylcarbonyl, formyl, aryl, aryloxycarbonyl, aryloxy, arylcarbonyl, heteroaryl, carbamido, alkanoyloxy, sulfono, alkylsulfonyloxy, nitro, azido, sulphanyl, alkylthio, halogen, DNA intercalators). Thus, (1S,5R,6R,8R)-5-(2-cyanoethoxy (diisopropylamino)phosphinoxy)-6-(4,4'-dimethoxytrityloxymethyl)-8-(thymin-1-yl)-2,7-dioxabicyclo[3.3.0]nonane was prepd. and incorporated into oligodeoxyribonucleotides. The nucleotide analogs, LNAs (Locked Nucleoside Analogs), are able to provide valuable improvements to oligonucleotides with respect to affinity and specificity towards complementary RNA and DNA oligomers. The novel type of LNA modified oligonucleotides, as well as the LNAs as such, are useful in a wide range of diagnostic applications as well as therapeutic applications. Among these can be mentioned antisense applications, PCR applications, strand displacement oligomers, as substrates for nucleic acid polymerases, as nucleotide based drugs, etc.

LNA has been shown to form exceedingly stable LNA:LNA Duplexes (Koshkin et al., Center for Synthetic Bioorganic Chemistry Department of Chemistry, University of Copenhagen, Copenhagen, Den. J. Am. Chem. Soc. (1998), 120(50), 13252–13253).

LNA:LNA hybridization was shown to be the most thermally stable nucleic acid type duplex system, and the RNA-mimicking character of LNA was established at the duplex level. Introduction of 3 LNA monomers (T or A) induced significantly increase melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

Synthesis of 2'-amino-LNA, a novel conformationally restricted high-affinity oligonucleotide analog with a Handle has been shown (see Singh et al., Center for Synthetic Bioorganic Chemistry Department of Chemistry, University of Copenhagen, Copenhagen, Den. J. Org. Chem. (1998), 63(26), 10035–10039.)

2'-Amino- and 2'-methylamino-locked nucleic acids (2'-amino-LNA) containing monomer nucleoside I (R=Me, $COCF_3$) were prepared and thermal stability of their duplexes with complementary RNA and DNA strands have been previously reported.

Similarly, The first analogs of LNA, phosphorothioate-LNA and 2'-thio-LNAs have been prepared (see Kumar et al., Center for Synthetic Bioorganic Chemistry, Department of Chemistry, University of Copenhagen, Copenhagen, Den. Bioorg. Med. Chem. Lett. (1998), 8(16), 2219–2222.) Synthesis of the chemically modified LNA analogs has also been reported. A 9-mer phosphorothioate-LNA containing three LNA thymine monomers (I, X=O, Y=S, R=Me) and 9-mer LNAs containing one, three or five 2'-thio-LNA monomers (I, X=S, Y=O, R=H) were able to recognize both complementary DNA and RNA with thermal affinities comparable to those of parent LNA.

Synthesis of novel bicyclo[2.2.1]ribonucleosides, 2'-amino- and 2'-thio-LNA monomeric nucleosides has been described in Singh et al., Center for Synthetic Bioorganic Chemistry Department of Chemistry Chemical Laboratory II, University of Copenhagen, Copenhagen, Den. J. Org. Chem. (1998), 63(18), 6078–6079.)

The present invention employs oligonucleotides for use in antisense modulation of the function of DNA or messenger RNA (mRNA) encoding a protein the modulation of which is desired, and ultimately to regulate the amount of such a protein. Hybridization of an antisense oligonucleotide with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, turnover or degradation of the mRNA and possibly even independent catalytic activity which may be engaged in by the RNA. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as modified oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases. The oligonucleotides of the present invention preferably comprise from about 5 to about 50 nucleosides. It is more preferred that such oligonucleotides comprise from about 8 to about 30 nucleosides, with 15 to 25 nucleosides being particularly preferred.

An oligonucleotide is a polymer of repeating units generically known as nucleotides or nucleosides. An unmodified (naturally occurring) nucleotide has three components: (1) a nitrogenous base linked by one of its nitrogen atoms to (2) a 5-carbon cyclic sugar and (3) a phosphate, esterified to carbon of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the C5 (5') position of the sugar of a first nucleotide and the C3 (3') position of a second, adjacent nucleotide. A "nucleoside" is the combination of (1) a nucleobase and (2) a sugar in the absence of a phosphate moiety (Kornberg, *DNA Replication*, W.H. Freeman & Co., San Francisco, 1980, pages 4–7). The backbone of an oligonucleotide positions a series of bases in a specific order; the written representation of this series of bases, which is conventionally written in 5' to 3' order, is known as a nucleotide sequence.

Oligonucleotides may comprise nucleoside or nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleosides or nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. Antisense oligonucleotides have also been used as diagnostic aids based on their specific binding or hybridization to DNA or mRNA that are present in certain disease states and due to the high degree of sensitivity that hybridization based assays and amplified assays that utilize some of polymerase chain reaction afford. The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenza virus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections. Other examples of antisense oligonucleotides are provided herein.

Specific examples of some preferred modified oligonucleotides envisioned for use in the ligand conjugated oligonucleotides of the present invention include oligonucleotides containing modified backbones or non-natural internucleoside linkages. As defined in this specification, oligonucleotides having modified backbones or internucleoside linkages include those that retain a phosphorus atom in the backbone and those that do not have a phosphorus atom in the backbone. For the purposes of this specification, and as sometimes referenced in the art, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified, and in fact more than one of the following modifications may be incorporated in a single antisense compound or even in a single residue thereof, for example, at a single nucleoside within an oligonucleotide.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, A; phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3'or 2'-5' to 5'-2'. Various salts, mixed salts and free acid forms are also included.

Representative United States Patents that teach the preparation of the above phosphorus atom containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages; mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

Some preferred embodiments of the present invention may employ oligonucleotides with phosphorothioate linkages and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand conjugated oligonucleotides of the present invention may additionally or alternatively comprise nucleobase (often referred to in the art simply as "base") modifications or substitutions. As used herein, "unmodified" or "natural" nucleobases include the purine bases adenine (a) and guanine (G), and the pyrimidine bases thymine (T), cytosine© and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with 2'-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned, and each of which is herein incorporated by reference, and commonly owned U.S. patent application Ser. No. 08/762,488, filed on Dec. 10, 1996, also herein incorporated by reference.

The oligonucleotides employed in the ligand conjugated oligonucleotides of the present invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. a preferred modification includes 2'-methoxyethoxy [2'-O—$CH_2CH_2OCH_3$, also known as 2'-O-(2-methoxyethyl) or 2'-MOE] (Martin et al., Helv. Chim. Acta, 1995, 78, 486), i.e., an alkoxyalkoxy group. a further preferred modification includes 2'-dimethylaminooxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide.

As used herein, the term "sugar substituent group" or "2'-substituent group" includes groups attached to the 2'-position of the ribofuranosyl moiety with or without an oxygen atom. Sugar substituent groups amenable to the present invention include, but are not limited to, fluoro, O-alkyl, O-alkylamino, O-alkylalkoxy, protected O-alkylamino, O-alkylaminoalkyl, O-alkyl imidazole and polyethers of the formula (O-alkyl)$_m$, wherein m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9:93); Ravasio et al. (J. Org. Chem. 1991, 56:4329); and Delgardo et. al. (Critical Reviews in Therapeutic Drug Carrier Systems 1992, 9:249), each of which is hereby incorporated by reference in its entirety. Further sugar modifications are disclosed by Cook (Anti-Cancer Drug Design, 1991, 6:585–607). Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-$NR_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons is disclosed by Hamm et al. (J. Org. Chem., 1997, 62:3415–3420). 2'-NR nucleosides are disclosed by Goettingen, M., J. Org. Chem., 1996, 61, 6273–6281; and Polushin et al., Tetrahedron Lett., 1996, 37, 3227–3230. Further representative 2'-substituent groups amenable to the present invention include those having one of formula XI or XII:

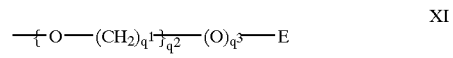

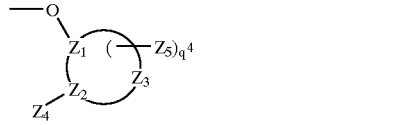

wherein:

E is $C_1$–$C_{10}$ alkyl, $N(Q_3)(Q_4)$ or $N=C(Q_3)(Q_4)$;

each $Q_3$ and $Q_4$ is, independently, H, $C_1$–$C_{10}$ alkyl, dialkylaminoalkyl, a nitrogen protecting group, a tethered or untethered conjugate group, a linker to a solid support;

or $Q_3$ and $Q_4$, together, form a nitrogen protecting group or a ring structure optionally including at least one additional heteroatom selected from N and O;

$q^1$ is an integer from 1 to 10;

$q^2$ is an integer from 1 to 10;

$q^3$ is 0 or 1;

$q^4$ is 0, 1 or 2;

each $Z_1$, $Z_2$ and $Z_3$ is, independently, $C_4$–$C_7$ cycloalkyl, $C_5$–$C_{14}$ aryl or $C_3$–$C_{15}$ heterocyclyl, wherein the heteroatom in said heterocyclyl group is selected from oxygen, nitrogen and sulfur;

$Z_4$ is $OM_1$, $SM_1$, or $N(M_1)_2$;

each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;

$M_2$ is H or $C_1$–$C_8$ alkyl; and $Z_5$ is $C_1$–$C_{10}$ alkyl, $C_1$–$C_{10}$ haloalkyl, $C_2$–$C_{10}$ alkenyl, $C_2$–$C_{10}$ alkynyl, $C_6$–$C_{14}$ aryl, $N(Q_3)(Q_4)$, $OQ_3$, halo, $SQ_3$ or CN.

Representative 2'-O-sugar substituent groups of formula XI are disclosed in U.S. patent application Ser. No. 09/130,973, filed Aug. 7, 1998, entitled "Capped 2'-Oxyethoxy oligonucleotides," hereby incorporated by reference in its entirety.

Representative cyclic 2'-O-sugar substituent groups of formula XII are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Sugars having O-substitutions on the ribosyl ring are also amenable to the present invention. Representative substitutions for ring O include, but are not limited to, S, $CH_2$, CHF, and $CF_2$. See, e.g., Secrist et al., Abstract 21, Program & Abstracts, Tenth International Roundtable, Nucleosides, Nucleotides and their Biological Applications, Park City, Utah, Sep. 16–20, 1992, hereby incorporated by reference in its entirety.

Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned, and each of which is herein incorporated by reference.

The present invention also includes compositions employing antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate oligodeoxynucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids, and ribozymes are not comprehended by the present invention.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxy-ethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy- substituted), or vice-versa.

A number of chemical modifications to oligonucleotides that confer greater oligonucleotide:RNA duplex stability have been described by Freier et al. (*Nucl. Acids Res.*, 1997, 25, 4429). Such modifications are preferred for the RNase H-refractory portions of chimeric oligonucleotides and may generally be used to enhance the affinity of an antisense compound for a target RNA.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned, and each of which is herein incorporated by reference, and commonly owned and allowed U.S. patent application Ser. No. 08/465,880, filed on Jun. 6, 1995, also herein incorporated by reference.

The present invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

The present invention further encompasses ligand conjugated oligonucleotides employing ribozymes. Synthetic RNA molecules and derivatives thereof that catalyze highly specific endoribonuclease activities are known as ribozymes. (See, generally, U.S. Pat. No. 5,543,508 to Haseloff et al., issued Aug. 6, 1996, and U.S. Pat. No. 5,545,729 to Goodchild et al., issued Aug. 13, 1996.) The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.*, 1986, 83, 8859; Forster et al., *Cell*, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

The oligonucleotides used in the conjugates of the present invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

Teachings regarding the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, issued Jun. 29, 1993, and U.S. Pat. No. 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

In the ligand conjugated oligonucleotides and ligand molecule-bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, or ligand-nucleotide or nucleoside conjugate precursors that already bear the ligand molecule.

When using nucleotide conjugate precursors that already bear a linking moiety, the synthesis of the sequence-specific linked nucleosides is typically completed, and the ligand molecule is then reacted with the linking moiety to form the ligand conjugated oligonucleotide. This approach to the synthesis of oligonucleotide conjugates bearing a variety of molecules such as steroids, vitamins, lipids and reporter molecules has previously been described (see Manoharan et al., PCT Application WO 93/07883). In a preferred embodiment the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

In application Ser. No. US91/00243, application Ser. No. 463,358 and application Ser. No. 566,977, all incorporated herein by reference, it is reported that incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. It is further reported that oligonucleotides containing phosphorothioate backbones have enhanced nuclease stability. Thus, functionalized, linked nucleosides of the invention can be augmented to further include either or both a phosphorothioate backbone or a 2'-O-methyl, 2'-O-ethyl, 2'-O-propyl, 2'-O-aminoalkyl, 2'-O-allyl or 2'-deoxy-2'-fluoro group thereon.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can conveniently be prepared utilizing the above noted 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand conjugated oligonucleotide bearing the ligand at the 5'-terminus.

In further preferred embodiments, functionalized nucleoside sequences of the invention can be prepared wherein a selected ligand is attached to the 3'-terminal amino group using a 3'-amino modified controlled pore glass (sold by Clontech Laboratories Inc., Palo Alto, Calif.) and subsequent attachment of the ligand is achieved by reaction with a ligand active ester.

In another preferred embodiment of the present invention, the ligand may be attached to the oligonucleotide at the 3'-terminus through the use of an appropriate multifunctional linker such as a universal linker. In this case the ligand is first derivatized with the universal linker and this conjugate then loaded onto a solid support. Subsequent synthesis of nucleic acids or oligonucleotides on this solid support affords upon cleavage and deprotection the ligand conjugated oligonucleotide bearing a ligand molecule at the 3'-terminus.

In still further preferred embodiments, functionalized sequences of nucleosides and ligand conjugated oligonucleotides of the present invention can be prepared wherein the ligand molecule is attached either directly or via a linking group to any one of the atoms of the nucleobase of any of the nucleoside units of the oligonucleotide. Thus, one or more ligand molecules may be attached to the nucleobase at the 3'-terminus, the 5'-terminus or any position in between. Such attachment can be accomplished, for example, by chemistries described in the literature, and mentioned above. The preferred mode of attachment of ligand molecules to nucleobases is via the intermediacy of an appropriate linker present on a nucleoside precursor. The ligand-nucleoside conjugate is then phosphitylated at the 3'-position to afford a ligand-nucleoside conjugate phosphoramidite which may be used subsequently as a building block together with traditional nucleoside phosphoramidites for the automated synthesis of oligonucleotides. The number and location of insertion of such ligand nucleotide conjugate phosphoramidites will then dictate the number and location of ligand molecules present in the synthesized ligand conjugated oligonucleotide of the present invention.

The present invention also provides ligand conjugated oligonucleotides wherein the ligand molecule is attached to one of the atoms of the internucleotide linkage. One typical internucleotide linkage in nucleic acids and oligonucleotides is the phosphodiester linkage. Numerous modified internucleotide linkages are known in the art including, but not limited to, phosphorothioate, methyl phosphonate, and phosphordithioate, as described above. Ligand molecules may be conjugated at one of the atoms of such internucleotide linkages with or without the intermediacy of a linking group. Attachment of the ligand molecule may be accomplished in accordance with the methods of the invention either during the preparation of the nucleoside building block such as the phosphoramidite or may be performed during the formation of the internucleotide linkage during oligonucleotide synthesis.

In further preferred embodiments of the invention, the ligand molecule is attached at multiple sites on one oligonucleotide. For example, ligand conjugated oligonucleotides can be prepared wherein one or more ligands are attached to both ends of a linked nucleoside sequence. Preferably such a structure is prepared by reacting a 3',5'-diamino sequence with a ligand active ester. The required oligonucleoside sequence can be synthesized, for example, utilizing the 3'-Amino-Modifier and the 5'-Amino-Modifier C6 (or Aminolink-2) reagents noted above or by utilizing the above noted 3'-amino modified controlled pore glass reagent in combination with the 5'-Amino-Modifier C2 (or Aminolink-2) reagents. Alternatively, such multiply conjugated oligonucleotides may readily be synthesized according to the methods of the invention using an appropriate ligand-nucleoside conjugate phosphoramidites as and where needed in a given oligonucleotide sequence during automated synthesis.

In still further preferred embodiments of the invention, an oligonucleoside sequence bearing an aminolinker at the 2'-position of one or more selected nucleosides is prepared using a suitably functionalized nucleotide such as, for example, 5'-dimethoxytrityl-2'-O-(ε-phthalimidylaminopentyl)-2'-deoxyadenosine-3'-N,N-diisopropyl-cyanoethoxy phosphoramidite. See the above referenced patent applications Ser. Nos. US91/00243, 566, 977 and 463,358. Preferably, the nucleotide or nucleotides are attached to the ligand by reaction with an active ester or a thioisocyanate thereof, at one or more of the nucleoside components of the oligonucleotide.

In yet further preferred embodiments, functionalized nucleoside sequences of the invention can be prepared wherein the heterocyclic base of one or more nucleosides can be linked to a ligand molecule. for example, utilizing 5'-O-dimethoxytrityl-5-[N(7-trifluoroacetylaminoheptyl)-3-acryl-amido]-2'-deoxyuridine 3'-O-(methyl N,N-diisopropyl)phosphoramide as described by Jablonski et. al. supra (also commercially available from Glen Research) the desired nucleoside, functionalized to incorporate a linking group on its heterocyclic base, is incorporated into the linked nucleoside sequence using a DNA synthesizer.

In further functionalized linked nucleosides of the invention, conjugation (or linking) of ligand molecules is achieved by conjugation of the ligand to the above described amino linking group on the nucleoside. This can be effected in several ways. For example, a ligand-nucleoside conjugate of the invention can be prepared by conjugation of the ligand molecule to the nucleoside using EDC/sulfo-NHS (i.e. 1-ethyl-3(3-dimethylaminopropylcarbodiimide/N-hydroxysulfosuccinimide) to conjugate the carboxylate function of the ligand with the amino function of the linking group on the nucleoside.

Ligand conjugated oligonucleotides of the present invention may be prepared by conjugation of the ligand molecule to the nucleoside sequence via a heterobifunctional linker such as m-maleimidobenzoyl-N-hydroxysulfosuccinimide ester (MBS) or succinimidyl 4-(N-maleimidomethyl) cyclohexane-1-carboxylate (SMCC), to link a nucleophilic position, preferably a thiol, on the ligand molecule to the amino function of the linking group on nucleoside sequence. By this mechanism, an oligonucleoside-maleimide conjugate is formed by reaction of the amino group of the linker on the linked nucleosides with the MBS or SMCC maleimide linker. The conjugate is then reacted with ligand molecules, preferably those that possess a thiol functionality.

Alternatively, an ligand conjugated oligonucleotide can be prepared by conjugation of the ligand molecule to the oligonucleotide or nucleoside via a homobifunctional linker such as disuccinimidyl suberate (DSS), to link an amino function on the ligand to the amino group of a linker on the oligonucleotide sequence. By this mechanism, an oligonucleoside-succinimidyl conjugate is formed by reaction of the amino group of the linker on the nucleoside sequence with a disuccinimidyl suberate linker. The disuccinimidyl suberate linker couples with the amine linker on the nucleoside to extend the size of the linker. The extended linker is then reacted with an amino group of the ligand molecule.

A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties such as cholesterol (Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann.*

N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

gated oligonucleotides of the present invention include, but are not limited to, 2'-6-aminoalkoxy-5'-ODMT-nucleosides, 2'-6-aminoalkylamino-5'-ODMT-nucleosides, 5'-6-aminoalkoxy-2'-deoxynucleosides, 5'-6-aminoalkoxy-2'-protected-nucleosides, 3'-6-aminoalkoxy-5'-ODMT-nucleosides, and 3'-aminoalkylamino-5'-ODMT-nucleosides that may be further protected in the nucleobase portion of the molecule. The use of such precursors is anticipated to afford ligand conjugated oligonucleotides where attachment is at one of many possible sites such as the 2', 3' or 5' position of one or more of the nucleoside components of oligonucleotides. Methods for the synthesis of such aminolinked protected nucleoside precursors are known to the art skilled and are available in the literature.

In one embodiment of the invention a conjugated oligonucleotide is prepared starting with a conjugated nucleoside using solid phase chemistries. An oligonucleoside is selected having a serum protein binding ligand attached or optionally linked to one the 2', 3', or 5' positions, a protected hydroxyl at one of the 2', 3', or 5' positions and a free hydroxyl group located at the other one of the 2', 3', or 5' positions. The free hydroxyl group is treated with a bifunctional linking moiety and the resulting nucleoside is reacted with a solid support. A representative conjugated nucleoside aattached via a succinyl linker at the 2'-O-position to a solid support (from Example 20) is shown below:

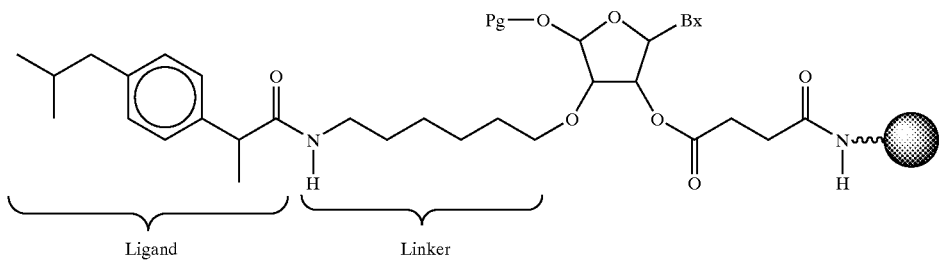

Ligand  Linker

Alternatively, the molecule being conjugated may be converted into a building block such as a phosphoramidite via an alcohol group present in the molecule or by attachment of a linker bearing an alcohol group that may be phosphitylated.

Each of these approaches may be used for the synthesis of ligand conjugated oligonucleotides. Aminolinked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers such as cysteamine may also be utilized for conjugation to a chloroacetyl linker present on a synthesized oligonucleotide.

In one preferred embodiment of the methods of the invention, the preparation of ligand conjugated oligonucleotides commences with the selection of appropriate precursor molecules upon which to construct the ligand molecule. Typically the precursor is an appropriately protected derivative of the commonly used nucleosides. For example, the synthetic precursors for the synthesis of the ligand conju- The ligand is ibuprofen and the linker is a preferred 6-aminohexlyoxy linking group. Bx is a heterocyclic base moiety and Pg is a hydroxyl protecting group. The resulting solid support bound conjugated nucleoside is treated with a weak acid to remove the hydroxyl protecting group and treated with a further nucleoside or nucleotide to form a dimer. In one aspect of the invention the coupling of further nucleosides to form a desired oligonucleotide is performed using phosphoramidite monomers following known methods and procedures.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to substituted and unsubstituted aromatic hydrocarbyl groups. Aralkyl groups (generally $C_7$–$C_{20}$) include but are not limited to groups having both aryl and alkyl functionalities, such as benzyl and xylyl groups. Preferred aryl and aralkyl groups include, but are not limited to, phenyl, benzyl, xylyl, naphthyl, toluyl, pyrenyl, anthracyl, phenanthryl, azulyl, phenethyl, cinnamyl, benzhydryl, and mesityl. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

As used herein, the term "alkanoyl" has its accustomed meaning as a group of formula —C(=O)-alkyl. A preferred alkanoyl group is the acetoyl group.

In general, the term "hetero" denotes an atom other than carbon, preferably but not exclusively N, O, or S, SO and $SO_2$. Accordingly, the term "heterocycle" denotes a cyclic structure having at least one non-carbon atom. "Cyclo" or "cyclyl" includes a cyclic group which may be mono-, bi- or tricyclic, and may be substituted with substituents such as oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, ODMT, alkylsulfonyl, nitro, sulfide, sulfone, sulfonamide, thiol and thioalkoxy.

Additional objects, advantages, and novel features of this invention will become apparent to those skilled in the art upon examination of the following examples, which are not intended to be limiting.

EXAMPLE 1

3'-O-Hexylaminofenbufenyl-5'-ODMT-5-methyluridine (1)

To a solution of 3'-O-(6-aminohexyl)-5-methyluridine (1.0 g, 1.51 mmol) (prepared according to the method described in Manoharan et al. (*Tetrahedron Lett.*, 1995, 36:3647) dissolved in $CH_2Cl_2$ (15 mL) was added fenbufen (sigma, 424 mg, 1.66 mmol), followed by N,N'-dicyclohexylcarbodiimide (Fluka, 342 mg, 1.66 mmol) with shaking for about 2 hours. The mixture was filtered to remove dicyclohexylurea and the filtrate was partitioned between $CH_2Cl_2$ (50 ml) and saturated sodium bicarbonate solution (50 mL). The organic layer was dried over anhydrous sodium sulfate and evaporated. The resultant foam was purified by silica gel column chromatography using 50:50 EtOAc:hexanes as the eluent to give 1.75 g (92%) of the title compound as a colorless solid.

$^1$H NMR ($CDCl_3$): δ (m, 4H), 2.62–2.66 (m, 2H), 3.17–3.56 (m, 10H), 3.76–3.78 (m, 6H, OMe), 4.03–4.32 (m, 2H), 5.38–5.42 (d, 1H), 5.93–5.94 (d, 1H), 6.11 (t, 1H), 6.81–8.06 (m, aromatic), 9.6 (6, 1H, NH). $^{13}$C NMR ($CDCl_3$): δ 14.15, 20.99, 25.58, 26.41, 29.40, 30.27, 34.13, 39.35, 55.21, 62.38, 70.75, 73.84, 81.34, 87.98, 89.64, 102.39, 113.26, 126.13, 127.17–135.214 (m), 139.72, 140.123, 144.212, 145.83, 150.59, 158.64, 163.21, 172.15, 198.85.

EXAMPLE 2

3'-O-Hexylaminofenbufenyl-2'-O-succinate-5'-O-DMT-5-methyl-uridine (2)

Compound 1 (1.00 g, 1.12 mmol), succinic anhydride (0.168 g, 1.68 mmol), dimethylaminopyridine (0.068 g, 0.56 mmol), and triethylamine (0.16 mL, 1.12 mmol) were dissolved in 1,2-dichloroethane (3 mL) at room temperature. The reaction mixture, in a test-tube with a screw cap top, was placed in a heating block at 55° C. for 2 hours and then allowed to cool to room temperature overnight. TLC using EtOAc:MeOH (85/15; v/v) showed complete conversion of the starting material. 1,2-Dichloroethane (30 mL) was added and the mixture was washed three times with portions of cold 10% citric acid (17 mL, aq) followed by three washes with portions of water (17 mL). The organic-phase was dried over sodium sulfate and evaporated to 1.14 g (100%) of the title compound as a foam.

$^1$H NMR (DMSO-$d_6$): δ 12.3 (s, 1H), 11.44 (s, 1H), 8.08–6.89 (m, 23H), 5.84 (d, 1H), 5.47 (m, 1H), 5.40 (d, 1H), 4.24 (m, 1H), 3.98 (m, 1H), 3.90 (m, 2H), 3.75 (s, 3H), 3.73 (s, 3H), 3.27 (m, 7H), 3.0 (m, 2H), 2.59 (m, 7H), 1.30 (m, 8H). (Kumar et al., *Nucleosides & Nucleotides*, 1993, 12:565–584).

EXAMPLE 3

3'-O-Hexylaminofenbufenyl-2'-O-succinate-5'-O-DMT-5-methyluridine LCAA-CPG (3)

Compound 2 (1.04 g, 1.05 mmol) and 4-methylmorpholine (0.23 mL, 2.10 mmol) were dissolved in DMF (19 mL) at room temperature. 2-(1H-Benzotriazole-1-yl)-1,1,3,3-tetra-methyluronium tetrafluoroborate (0.34 g, 1.05 mmol) and acid washed LCAA-CPG (4.56 g, 0.52 mmol) were added and the mixture was shaken overnight. The resulting resin was then washed three times with $CH_2Cl_2$ and three times with ether. The initial loading was found to be 41 μmol/g. The resin was then combined with Cap A (20 mL) and Cap B (20 mL) solutions from PerSeptive Biosystems GmbH, and shaken for another hour and washed with three portions of $CH_2Cl_2$ and ether. The capped resin 3 was placed under vacuum to dry overnight and the loading was determined to be 46 μmol/g.

EXAMPLE 4

3'-O-(6-Aminohexyl-ketoprofanyl)-5'-O-DMT-5'-methyluridine (4)

To a solution of 3'-O-(6-aminohexyl)-5-methyluridine (1.0 g, 1.51 mmol) in $CH_2Cl_2$ (15 mL) was added a solution of ketoprofen (sigma, 422 mg, 1.66 mmol) and DCC (Fluka, 342 mg, 1.66 mmol) with shaking for 2 hrs. The mixture was filtered and the filtrate was partitioned between $CH_2Cl_2$ (50 mL) and a solution of saturated sodium bicarbonate (50 mL). The organic layer was separated, dried over anhydrous sodium sulfate and evaporated. The residual foam was purified by silica gel column chromatography using 50:50 ethylacetate:hexanes as the eluent to give 1.82 g (88%) of the title compound.

$^{13}$C NMR ($CDCl_3$): δ 18.63, 25.55, 26.38, 29.32, 39.44, 46.90, 55.20, 62.41, 70.75, 73.82, 81.33, 86.99, 89.53, 102.39, 113.24, 127.12, 127.99, 128.29, 129.65, 129.02, 130.02, 131.48, 132.56, 135.07, 135.19, 137.01, 137.89, 140.11, 142.04, 144.108, 150.53, 158.64, 163.11, 173.51.

EXAMPLE 5

3'-O-Hexylaminoketoprofenyl-2'-O-succinate-5'-O-DMT-5-methyluridine (5)

Compound 4 (1.00 g, 1.12 mmol), succinic anhydride (0.168 g, 1.68 mmol), dimethylaminopyridine (0.068 g, 0.56 mmol), and triethylamine (0.16 mL, 1.12 mmol) were dissolved in 1,2-dichloroethane (3 mL) at room temperature. The reaction mixture (in a test-tube with a screw cap top) was placed in a heating block at 55° C. for 2 hours and then cooled to room temperature. TLC using EtOAc:MeOH (85/15; v/v) showed the absence of starting material. The mixture was diluted with 1,2-dichloroethane (30 mL) and washed three times with cold 10% citric acid (aqueous, 17 mL) and three times with water (17 mL). The organic-phase was dried over sodium sulfate and evaporated to give 1.14 g (100%) of the title compound as a foam.

$^1$H NMR (DMSO-$d_6$): δ 12.3 (s, 1H), 11.45 (s, 1H), 8.02 (m, 1H), 7.82–6.88 (m, 23H), 5.84 (d, 1H), 5.48 (m, 1H), 5.40 (d, 1H), 4.24 (m, 1H), 3.99 (m, 1H), 3.92 (m, 2H), 3.74 (s, 6H), 3.32 (m, 5H), 3.00 (m, 2H), 2.51 (m, 5H), 1.36 (m, 7H), 1.14 (s, 4H).

EXAMPLE 6

3'-O-Hexylaminoketoprofenyl-2'-O-succinate-5'-O-DMT-5-methyluridine LCAA-CPG (6)

Compound 5 (1.04 g, 1.05 mmol) and 4-methylmorpholine (0.23 mL, 2.10 mmol) were dissolved in DMF (19 mL) at room temperature. 2-(1H-Benzotriazole-1-yl)-1,1,3,3-tetramethyluronium tetrafluoroborate (0.34 g, 1.05 mmol) and acid washed LCAA-CPG (4.56 g, 0.52 mmol) were added and the mixture was shaken overnight. The resulting resin was washed with $CH_2Cl_2$ (×3) and ether (×3). The initial loading was found to be 32 μmol/g. The resin was combined with Cap A (20 mL) and Cap B (20 mL) solutions from PerSeptive Biosystems GmbH, and shaken for another hour. The resin was washed again with $CH_2Cl_2$ (×3) and ether (×3). The capped resin (6) was dried under vacuum overnight. The loading was determined to be 44 μmol/g.

EXAMPLE 7

3'-O-(6-Aminohexyl-suprofenyl)-5'-O-DMT-5-methyluridine (7)

To a solution of 3'-O-(6-aminohexyl)-5-methyluridine (1.0 g, 1.51 mmol) in $CH_2Cl_2$ (15 mL) was added a solution of suprofen (sigma, 432 mg, 1.66 mmol) followed by DCC (Fluka, 342 mg, 1.66 mmol). After shaking the reaction mixture for 2 hours, dicyclohexyl urea was filtered off. The resulting organic solution was partitioned between $CH_2Cl_2$ (50 mL) and a solution of saturated $NaHCO_3$. The organic layer was separated, dried over anhydrous sodium sulfate and evaporated. The resulting product was purified by silica gel column chromatography using 50:50 ethylacetate:hexanes as the eluant to give 1.75 g (88%) of the title compound as a colorless solid.

$^{13}$C NMR (CDCl$_3$): δ 14.06, 18.61, 25.56, 26.41, 29.33, 29.44, 39.49, 47.08, 55.21, 60.36, 62.43, 70.75, 73.83, 81.352, 87.00, 89.54, 102.39, 113.24, 127.13, 127.65, 127.98, 129.68, 130.03, 134.30, 134.82, 135.06, 135.19, 136.99, 141.122, 143.41, 114.17, 146.16, 150.52, 158.60, 163.24, 173.25, 187.696.

EXAMPLE 8

3'-O-Hexylaminosuprofenyl-2'-O-succinate-5'-O-DMT-5-methyluridine (8)

Compound 7 (1.00 g, 1.11 mmol), succinic anhydride (0.167 g, 1.66 mmol), dimethylaminopyridine (0.068 g, 0.56 mmol), and triethylamine (0.15 mL, 1.11 mmol) were dissolved in 1,2-dichloroethane (3 mL) at room temperature. The reaction mixture (in a test-tube with a screw cap top) was placed in a heating block at 55° C. for 2 hours and then cooled to room temperature overnight. TLC using EtOAc:MeOH (85:15, v/v) showed that all the starting material had been converted. The mixture was diluted with 1,2-dichloroethane (30 mL) washed three times with cold 10% acid (aqueous, 17 mL) and three times with water (17 mL). The organic-phase was dried over sodium sulfate and evaporated to give 1.13 g (100%) of the title compound as a foam.

$^1$H NMR (DMSO-$d_6$): δ 12.3 (s, 1H), 11.44 (s, 1H), 8.12–6.88 (m, 21H), 5.84 (d, 1H), 5.48 (m, 1H), 5.40 (d, 1H), 4.24 (m, 1H), 3.99 (m, 1H), 3.91 (m, 3H), 3.74 (s, 6H), 3.32 (m, 5H), 3.02 (m, 2H), 2.54 (m, 5H), 1.37 (m, 7H), 1.16 (s, 4H).

EXAMPLE 9

3'-O-Hexylaminosuprofenyl-2'-O-succinate-5'-O-DMT-5-methyluridine LCAA-CPG (9)

Compound 8 (1.03 g, 1.03 mmol) and 4-methylmorpholine (0.23 mL, 2.06 mmol) were dissolved in DMF (19 mL) at room temperature. 2-(1H-Benzotriazole-1-yl)-1,1,3,3-tetramethyluronium tetrafluoroborate (0.33 g, 1.03 mmol) and acid washed LCAA-CPG (4.47 g, 0.52 mmol) were added and the mixture was shaken overnight. The resulting resin was then washed with $CH_2Cl_2$ (×3) and ether (×3). The initial loading was found to be 36 μmol/g. The resin was then combined with Cap A (20 mL) and Cap B (20 mL) solutions from PerSeptive Biosystems GmbH, and shaken for one hour. The resin was washed with $CH_2Cl_2$ (×3) and ether (×3). The capped resin 9 was dried under vacuum overnight and the loading was determined to be 47 μmol/g.

EXAMPLE 10

3'-O-(6-Aminohexyl-carprofenyl)-5'-ODMT-5methyluridine (10)

To a solution of 3'-O-(6-aminohexyl)-5-methyluridine (1.0 g, 1.51 mmol) in $CH_2Cl_2$ (15 mL) was added carprofen (sigma, 453 mg, 1.66 mmol) followed by DCC (Fluka, 342 mg, 1.66 mmol). After shaking the reaction mixture for 2 hours, dicyclohexyl urea was filtered off. The resulting organic solution was partitioned between $CH_2Cl_2$ (50 mL) and a solution of saturated $NaHCO_3$. The organic layer was dried over anhydrous sodium sulfate, evaporated. The resulting product was purified by silica gel column chromatography using 50:50 ethylacetate:hexanes as the eluant to give 1.65 g (84%) of the title compound as a colorless solid.

EXAMPLE 11

3'-O-Hexylaminocarprofenyl-2'-O-succinate-S'-O-DMT-5-methyluridine (11)

Compound 10 (1.00 g, 1.09 mmol), succinic anhydride (0.164 g, 1.64 mmol), dimethylaminopyridine (0.066 g, 0.54 mmol), and triethylamine (0.15 mL, 1.09 mmol) were dissolved in 1,2-dichloroethane (3 mL) at room temperature. The reaction mixture (in a test-tube with a screw cap top) was placed in a heating block at 55° C. for 2 hours and then cooled to room temperature. TLC using EtOAc:MeOH (85/15/v/v) showed that the starting material was converted. The mixture was diluted with 1,2-dichloroethane (30 mL) and washed three times with cold 10% citric acid (aqueous, 17 mL) and three times with water (17 mL). The organic phase was dried over sodium sulfate and evaporated to give 1.07 g (97%) of the title compound as a foam.

$^1$H NMR (DMSO-$d_6$): δ 12.3 (s, 1H), 11.45 (s, 1H), 11.36 (s, 1H), 8.16–6.88 (m, 20H), 5.84 (d, 1H), 5.48 (m, 1H), 5.41 (d, 1H), 4.23 (m, 1H), 3.99 (m, 1H), 3.92 (m, 1H), 3.74 (s, 6H), 3.32 (m, 5H), 3.02 (m, 2H), 2.54 (m, 5H), 1.29 (m, 12H).

EXAMPLE 12

3'-O-Hexylaminocarprofenyl-2'-O-succinate-5'-O-DMT-5-methyluridine LCAA-CPG (12)

Compound 11 (0.970 g, 0.96 mmol) and 4-methylmorpholine (0.21 mL, 1.92 mmol) were dissolved in DMF (19 mL) at room temperature. 2-(1H-Benzotriazole-1-yl)-1,1,3,3-tetramethyluronium tetrafluoroborate (0.31 g, 0.96 mmol) and acid washed LCAA-CPG (4.14 g, 0.48 mmol) were added and the mixture was shaken overnight. The resulting resin was washed with $CH_2Cl_2$ (×3) and ether (×3). The initial loading was found to be 39 µmol/g. The resin was then combined with Cap A (20 mL) and Cap B (20 mL) solutions from PerSeptive Biosystems GmbH, and shaken for one hour. The resin was again washed with $CH_2Cl_2$ (×3) and ether (×3). The capped resin 12 was dried under vacuum. The loading was determined to be 41 µmol/g.

EXAMPLE 13

3'-O-(6-Aminohexyl-palmityl)-5'-O-DMT-2'-O-succinyluridine (13)

To a solution of 3'-O-(6-aminohexyl)-5'-O-DMT-uridine (1.5 g, 2.33 mmol) in $CH_2Cl_2$ (20 mL) at room temperature was added diisopropylamine (0.81 mL, 4.66 mmol) followed by palmitic acid pentafluorophenyl ester (compound, vide infra, 1.04 g, 2.8 mmol) with stirring overnight. The mixture was concentrated and the residue purified by silica gel column chromatography using EtOAc:$CH_3OH$ (90:10; v/v) as the eluant to give 1.39 g (72%) of the title compound without the 2'-O-succinyl group attached.

The above conjugate (1.12 mmol), succinic anhydride (0.17 g, 1.7 mmol), dimethyl amino pyridine (0.068 g, 0.56 mmol) and triethyl amine (0.16 mL, 1.12 mmol) were dissolved in 1,2-dichloroethane (3 mL) at room temperature in a test-tube with a screw cap top. The reaction mixture was placed in a heating block at 55° C. for 2 hours and then cooled to room temperature. TLC using EtOAc:MeOH (85:15; v/v) showed the absence of starting material. The mixture was diluted with 1,2-dichloroethane (30 mL) and washed three times with cold 10% aqueous citric acid (25 mL) and three times with water (25 mL). The organic phase was dried over sodium sulfate and evaporated to give 1.2 g (quantitative yield) of the title compound as a foam.

EXAMPLE 14

5'-O-DMT-3'-O-Palmitylaminohexyl-2'-O-succinyluridine LCAA-CPG (14)

Compound 13 (1.35 g, 1.35 mmol) and 4-dimethylaminopyridine (0.16 g, 1.35 mmol) were dissolved in $CH_3CN$ (12.2 mL) at room temperature in a first flask. In a second flask, 2,2'-dithiobis-5-nitropyridine (0.42 g, 1.35 mmol) was dissolved in acetonitrtile (8.53 mL) and dicholoromethane (3.64 mL) and the resulting solution was added to the first flask. In a third flask, triphenylphosphine (0.35 g, 1.35 mmol) was dissolved in anhydrous $CH_3CN$ (12.2 mL) and the resulting solution was added to the first flask. Acid washed LCAA-CPG (10.9 g, having a loading of 115 mol/g) was added and the mixture was shaken for about 3 hours. The resulting resin was washed with $CH_3CN$ (×3) followed by $CH_2Cl_2$ and ether to removed excess reagents. To the washed resin was added acetic anhydride (25 mL) in tetrahydrofuran (THF) and 1-methylimidazole (25 mL) in THF (Cap A and Cap B reagents from Perseptive Biosystems GmbH) and the mixture was shaken for an 2 hours. The resin was again washed again with $CH_2Cl_2$ (×3) and ether (×3). The washed resin was dried overnight in a vacuum oven at room temperature under $P_2O_5$. The yield of dried resin was 10.8 g with the loading determined to be 44 mol/g.

A portion of the final resin (3.8 mg) was cleaved by treatment with trichloroacetic acid (25 mL, 3%) in $CH_2Cl_2$. The loading was determined by measuring the absorption of released trityl cation at 503 nm on a spectrophotometer (Hewlett packard 8452A Diode Array spectrophotometer). The final derivatized resin yield was 10.8 g total.

EXAMPLE 15

3'-O-Hexylaminopalmityl-5'-O-DMT-cytidine (15)

To 3'-O-hexylamino-5'-O-DMT-cytidine (1.50 g, 2.33 mmol) (purchased from RI Chemical, CA) dissolved in $CH_2Cl_2$ (20 mL) at room temperature was added diisopropylamine (0.81 mL, 4.66 mmol) and palmitic acid pentafluorophenyl-ester (1.18 g, 2.80 mmol) with stirring overnight. The mixture was was evaporated and the resulting crude purified by silica gel column chromatography using EtOAc:MeOH (90/10; v/v) as the eluant to give 1.20 g (59%) of the title compound.

$^1$H NMR (CDCl$_3$): δ 7.99 (d, 1H), 7.40–6.81 (m, 15H), 5.91 (d, 1H), 5.63 (m, 1H), 5.49 (d, 1H), 4.32 (m, 1H), 4.19 (m, 1H), 4.03 (m, 1H), 3.79 (s, 6H), 3.54 (m, 2H), 3.38 (m, 2H), 3.20 (m, 2H), 2.14 (t, 2H), 1.58–1.24 (m, 34H), 0.87 (t, 3H). $^{13}$C (CDCl$_3$): δ 173.32, 165.30, 158.63, 156.01, 144.40, 141.54, 135.48, 135.37, 130.09, 128.11, 127.96, 127.06, 113.25, 94.35, 91.36, 86.76, 81.37, 74.27, 70.85, 62.02, 56.30, 55.26, 52.82, 39.33, 36.86, 31.92, 29.69, 29.52, 29.36, 26.60, 25.85, 25.70, 22.69, 18.14, 14.11. MS (ES$^-$) calculated for $C_{52}H_{74}N_4O_8$ 882.6; Observed 881.8.

EXAMPLE 16

3'-O-Hexylaminopalmityl-5'-O-DMT-N4-Benzoylcytidine (16)

To compound 15 (1.20 g, 1.36 mmol) dissolved in N,N-dimethylformamide (30 mL) at room temperature was added benzoic anhydride (0.37 g, 1.63 mmol) with stirring overnight. Saturated aqueous sodium bicarbonate was added and the mixture was extracted with ethyl acetate (×3). The organic-phase was dried over magnesium sulfate and evaporated. The crude product was then purified by silica gel column chromatography using EtOAc:MeOH (95/5; v/v) as the eluant to give 0.90 g (67%) of the title compound.

$^1$H NMR (CDCl$_3$) δ 8.75 (s, 1H), 8.41 (d, 1H), 7.92–6.85 (m, 20H), 6.00 (d, 1H), 5.49 (m, 1H), 4.38 (m, 1H), 4.27 (m, 1H), 4.09 (m, 1H), 3.82 (s, 6H), 3.50 (m, 5H), 3.23 (m, 2H), 2.15 (t, 2H), 1.45 (m, 34H), 0.88 (t, 3H); $^{13}$C (CDCl$_3$) δ 173.15, 162.25, 158.72, 144.83, 144.07, 135.48, 135.28, 133.19, 130.10, 129.99, 129.05, 128.15, 128.05, 127.54, 127.20, 113.35, 91.80, 87.04, 81.79, 77.23, 76.97, 74.55, 71.00, 61.82, 55.26, 39.30, 36.91, 31.92, 29.69, 29.65, 29.50, 29.36, 26.60, 25.83, 25.72, 22.69, 14.12. MS (ES$^-$) calculated for $C_{59}H_{78}N_4O_9$—DMT group 683.2. Observed 681.1 (16 without DMT group).

EXAMPLE 17

3'-O-Hexylaminopalmityl-2'-O-succinate-5'-O-DMT-N4-benzoyl-cytidine (17)

Compound 16 (0.88 g, 0.89 mmol), succinic anhydride (0.134 g, 1.34 mmol), dimethylaminopyridine (0.054 g, 0.44 mmol), and triethylamine (0.12 mL, 0.89 mmol) were dissolved in 1,2-dichloroethane (4 mL) at room temperature. The reaction mixture (in a test-tube with a screw cap top) was placed in a heating block at 55° C. for 1 hour and cooled to room temperature overnight. TLC using EtOAc:MeOH (90/10; v/v) showed conversion of the starting material. The mixture was diluted with $CH_2Cl_2$ (40 mL) and the mixture was washed with cold 10% citric acid (20 mL, aq, ×3) followed by water (20 mL, ×3). The organic phase was dried over magnesium sulfate and evaporated to give 0.97 g (100%) of the title compound as a foam.

H NMR (DMSO-$d_6$) δ 8.34 (d, 1H), 7.95–6.86 (m, 20H), 6.10 (d, 1H), 5.72 (m, 1H), 5.37 (m, 1H), 4.18 (m, 2H), 3.82 (s, 6H), 3.54 (m, 2H), 3.28 (m, 4H), 2.74 (m, 4H), 2.16 (t, 2H), 1.45 (m, 34H), 0.88 (t, 3H). $^{13}$C (CDCl$_3$) δ 174.94, 174.08, 170.81, 162.73, 158.72, 154.29, 144.66, 144.04, 135.52, 135.28, 133.08, 132.97, 130.10, 129.99, 128.90, 128.16, 128.07, 127.90, 127.20, 113.37, 96.94, 89.29, 88.83, 86.98, 81.57, 77.23, 75.45, 74.47, 71.89, 61.01, 55.26, 39.37, 36.84, 32.22, 31.92, 29.69, 29.50, 29.36, 29.30, 29.06, 28.86, 28.47, 26.36, 25.76, 25.16, 24.70, 22.69, 14.12. MS (ES$^-$) calculated for $C_{63}H_{82}N_4O_{12}$ 1086.6. Observed 1085.4.

EXAMPLE 18

3'-O-Hexylaminopalmityl-2'-O-succinate-5'-O-DMT-N4-benzoyl-cytidine LCAA-CPG (18)

Compound 17 (0.95 g, 0.87 mmol) and 4-dimethylaminopyridine (0.11 g, 0.87 mmol) were dissolved in $CH_3CN$ (7.0 mL) and $CH_2Cl_2$ (4 mL) at room temperature in a first flask. In a second flask 2,2'-dithiobis(5-nitropyridine) (0.28 g, 0.87 mmol) was dissolved in $CH_3CN$ (6.0 mL) and $CH_2Cl_2$ (2.5 mL) and added to the first flask. In a third flask triphenylphosphine (0.23 g, 0.87 mmol) was dissolved in $CH_3CN$ (7.0 mL) and then combined with the first flask. To the resulting mixture was added acid washed LCAA-CPG (3.78 g, 0.44 mmol) with shaking for about 2 hours. The resulting resin was washed with $CH_2Cl_2$ (×3) and ether (×3). Then it was combined with Cap A (25 mL) and Cap B (25 mL) solutions from PerSeptive Biosystems GmbH, and shaken for one hour. The resin was again washed with $CH_2Cl_2$ (×3) and ether (×3) and placed under vacuum overnight to dry. The final loading was determined to be 58 μmol/g.

EXAMPLE 19

3'-O-(6-Aminohexyl-palmityl)-5'-O-DMT-uridine (19)

To a solution of 3'-O-(6-aminohexyl)-5'-O-DMT-uridine (1.5 g, 2.33 mmol) in $CH_2Cl_2$ (20 mL) at room temperature was added diisopropylamine (0.81 mL, 4.66 mmol) followed by ibuprofen pentafluorophenyl ester (compound 21, vide infra 1.04 g, 2.8 mmol) with stirring overnight. The mixture was concentrated and the residue purified by silica gel column chromatography using EtOAc:CH$_3$OH (90:10; v/v) as the eluant to give 1.39 g (72%) of the title compound minus the succinyl group.

The above conjugate (1.12 mmol) succinic anhydride (0.17g, 1.7 mmol), dimethylaminopyridine (0.068 g, 0.56 mmol) and triethyl amine (0.16 mL, 1.12 mmol) were dissolved in 1,2-dichloroethane (3 mL) at room temperature in a test-tube with a screw cap top. The reaction mixture was placed in a heating block at 55° C. for 2 hours and then cooled to room temperature. TLC using EtOAc:MeOH (85:15; v/v) showed the absence of starting material. The mixture was diluted with 1,2-dichloroethane (30 mL) and washed three times with cold 10% aqueous citric acid (25 mL) and three times with water (25 mL). The organic phase was dried over sodium sulfate and evaporated to give 1.2 g (quantitative yield) of the title compound as a foam.

EXAMPLE 20

5'-O-DMT-3'-O-Ibuprofenylaminohexyl-2'-O-succinyluridine LCAA-CPG (20)

Compound 19 (1.02 g, 1.08 mmol) and 4-dimethylaminopyridine (0.13 g, 1.08 mmol) were dissolved in $CH_3CN$ (9.73 mL) at room temperature in a flask. To this solution was added a solution of 2,2'-dithiobis(5-nitropyridine) (0.34 g, 1.08 mmol) dissolved in acetonitrtile (6.80 mL) and $Cl_2Cl_2$ (2.90 mL) followed by a solution of triphenylphosphine (0.28 g, 1.08 mmol) dissolved in $CH_3CN$ (9.73 mL). To this mixture was added acid washed LCAA-CPG (8.69 g, with a loading of 115 mol/g) with shaking for about 2.5 hours. The resulting resin was washed with $CH_3CN$ (×3), $CH_2Cl_2$ (×3), and ether (×3) to removed excess reagents. The washed resin was combined with acetic anhydride (25 mL) in THF and 1-methylimidazole (25 mL) in THF (Cap A and Cap B reagents from Perseptive Biosystems GmbH) with shaking for 2 hours. The resin was again washed with dichloromethane (×3) and ether (×3). Finally, it was dried overnight in a vacuum oven at room temperature under $P_2O_5$. The final loading was determined to be 53 mol/g.

A portion of the final resin (3.0 mg) was cleaved by treatment with trichloroacetic acid (25 mL, 3%) in $CH_2Cl_2$. The loading was determined by measuring the absorption of released trityl cation at 503 nm on a spectrophotometer (Hewlett Packard 8452A Diode Array spectrophotometer). The final derivatized resin yield was 8.90 g total.

EXAMPLE 21

Ibuprofenylpentafluorophenyl Ester (21)

To a solution of ibuprofen (2.00 g, 9.70 mmol, Sigma) dissolved in tetrahydrofuran (20 mL) at room temperature was added 4-dimethylaminopyridine (0.24 g, 1.94 mmol) and 1,3-dicyclohexylcarbodiimide (2.00 g, 9.70 mmol) with stirring for 20 minutes. To this mixture was added pentafluorophenol (1.78 g, 9.70 mmol) with stirring overnight. The mixture was then filtered, to remove DCU, and $CH_2Cl_2$ was added. The mixture was washed with water (×2), dried over magnesium sulfate, and evaporated to an oil. The oil was purified by silica gel column chromatography using ethyl acetate:hexanes (5/95, v/v) as the eluant to give 2.70 g (75%) of the title compound.

$^1$H NMR (CDCl$_3$) δ 7.21 (m, 4H), 4.05 (q, 1H), 2.47 (d, 2H), 1.86 (m, 1H), 1.63 (d, 3H), 0.90 (d, 6H). $^{13}$C (CDCl$_3$) δ 129.65, 127.17, 45.04, 44.70, 30.18, 22.34, 18.51. MS (ES$^-$) calculated for $C_{19}H_{17}F_5O_2$ $[M-2H]^{2-}$ 186.1. Observed $[M-2H]^{2-}$ 183.2.

EXAMPLE 22

3'-O-Hexylaminoibuprofenyl-5'-O-DMT-cytidine (22)

To a solution of 3'-O-hexylamino-5'-O-DMT-cytidine (1.50 g, 2.33 mmol) dissolved in $CH_2Cl_2$ (20 mL) at room temperature was added diisopropylamine (0.81 mL, 4.66 mmol) and compound 21 (1.04 g, 2.80 mmol) with stirring overnight. The mixture was concentrated and the residue purified by silica gel column chromatography using EtOAc:MeOH (90/10; v/v) as the eluant to give 1.46 g (75%) of the title compound.

$^1$H NMR (CDCl$_3$) δ 8.00 (d, 1H), 7.39–6.80 (m, 17H), 5.90 (d, 1H), 5.80 (s, 3H), 5.48 (d, 1H), 4.29 (m, 1H), 4.18 (m, 1H), 4.02 (m, 1H), 3.78 (s, 6H), 3.62–3.31 (m, 6H), 3.13 (m, 2H), 2.43 (d, 2H), 1.83 (m, 1H), 1.48 (d, 3H), 1.40–1.18 (m, 8H), 0.88 (d, 6H). $^{13}$C (CDCl$_3$) δ 174.54, 165.40, 158.63, 156.30, 144.43, 141.45, 140.68, 138.65, 135.52, 135.37, 130.09, 129.58, 128.13, 127.98, 127.33, 127.07, 113.24, 94.35, 91.47, 86.74, 81.32, 74.26, 70.84, 61.96, 55.22, 52.53, 46.74, 44.99, 41.06, 39.42, 30.14, 29.52, 29.34, 26.43, 25.59, 22.35, 18.50, 18.20, 12.09. MS (ES$^-$) calculated for C$_{49}$H$_{60}$N$_4$O$_8$ 832.4. Observed 831.7.

EXAMPLE 23

3'-O-Hexylaminoibuprofenyl-5'-O-DMT-N4-benzoylcytidine (23)

To a solution of compound 22 (1.45 g, 1.74 mmol) dissolved in N,N-dimethylformamide (30 mL) at room temperature was added benzoic anhydride (0.0.57 g, 2.53 mmol) with stirring overnight. Saturated aqueous sodium bicarbonate was added and the mixture was extracted with ethyl acetate (×3). The organic phase was dried over magnesium sulfate, filtered and concentrated. The crude product was then purified by silica gel column chromatography using EtOAc:MeOH (90/10; v/v) as the eluant to give 0.97 g (60%) of the title compound.

$^1$H NMR (CDCl$_3$) δ 8.75 (s, 1H), 8.41 (d, 1H), 7.91–6.84 (m, 22H), 5.99 (d, 1H), 5.35 (m, 1H), 4.37 (m, 1H), 4.26 (m, 1H), 4.08 (m, 1H), 3.81 (s, 6H), 3.62–3.36 (m, 5H), 3.15 (m, 2H), 2.44 (d, 2H), 1.84 (m, 1H), 1.50 (d, 3H), 1.45–1.16 (m, 8H), 0.89 (d, 6H). $^{13}$C (CDCl$_3$) δ 174.42, 162.26, 158.73, 144.06, 140.68, 138.68, 135.49, 135.26, 133.20, 130.11, 129.98, 129.61, 129.08, 128.15, 128.06, 127.52, 127.36, 127.21, 113.35, 91.81, 87.04, 81.80, 74.56, 71.01, 61.81, 56.28, 55.25, 46.80, 44.99, 39.40, 36.48, 30.18, 29.52, 29.42, 26.46, 25.63, 22.38, 18.50. MS (ES$^-$) calculated for C$_{56}$H$_{64}$N$_4$O$_9$ 936.5. Observed 935.9.

EXAMPLE 24

3'-O-Hexylaminoibuprofenyl-2'-O-succinate-S'-O-DMT-N4-benzoylcytidine (24)

Compound 23 (0.95 g, 1.01 mmol), succinic anhydride (0.152 g, 1.52 mmol), dimethylaminopyridine (0.062 g, 0.50 mmol), and triethylamine (0.14 mL, 1.01 mmol) were dissolved in 1,2-dichloroethane (4.5 mL) at room temperature. The reaction mixture (in a test-tube with a screw cap top) was placed in a heating block at 55° C. for 1 hour and then allowed to cool to room temperature. TLC using EtOAc:MeOH (90/10; v/v) showed the conversion of the starting material. The mixture was diluted with CH$_2$Cl$_2$ (45 mL) washed three times with cold 10% citric acid (aqueous, 20 mL) and three times with water (20 mL). The organic-phase was dried over magnesium sulfate and evaporated to give 1.05 g (100%) of the title compound as a foam.

$^1$H NMR (DMSO-d$_6$) δ 8.31 (d, 1H), 7.93 (m, 2H), 7.51–6.85 (m, 21H), 6.10 (d, 1H), 5.54 (m, 1H), 5.35 (m, 1H), 4.18 (s, 2H), 3.82 (s, 6H), 3.53 (m, 4H), 3.33–3.01 (m, 3H), 2.73 (m, 4H), 2.44 (d, 2H), 1.84 (m, 1H), 1.49 (d, 3H), 1.47–1.19 (m, 8H), 0.89 (d, 6H). $^{13}$C (CDCl$_3$) δ 175.31, 174.91, 170.79, 162.75, 158.72, 154.25, 144.66, 144.04, 140.76, 138.34, 135.54, 135.28, 133.06, 132.97, 130.10, 129.99, 129.64, 128.88, 128.18, 128.07, 127.92, 127.42, 127.20, 113.35, 96.94, 88.77, 86.98, 81.61, 75.47, 74.51, 71.91, 61.06, 55.24, 46.69, 44.99, 43.44, 39.50, 30.15, 29.71, 29.49, 29.04, 28.78, 26.24, 25.11, 22.37, 18.38. MS (ES$^-$) calculated for C$_{60}$H$_{68}$N$_4$O$_{12}$ 1036.5. Observed 1035.8.

EXAMPLE 25

3'-O-Hexylaminoibuprofenyl-2'-O-succinate-5'-O-DMT-N4-benzoylcytidine LCAA-CPG (25)

To a solution of compound 24 (1.03 g, 0.99 mmol) and 4-dimethylaminopyridine (0.12 g, 0.99 mmol) dissolved in CH$_3$CN (8.0 mL) at room temperature was added a solution of 2,2'-dithiobis(5-nitropyridine) (0.31 g, 0.99 mmol) dissolved in CH$_3$CN (7.0 mL) and CH$_2$Cl$_2$ (3.0 mL) followed by a solution of triphenylphosphine (0.26 g, 0.99 mmol) dissolved in CH$_3$CN (8.0 mL). To the resulting mixture was added acid washed LCAA-CPG (4.31 g, 0.50 mmol) and the mixture was shaken for about 2 hours. The resulting resin was washed with CH$_2$Cl$_2$ (×3) and ether (×3). Then it was combined with Cap A (26 mL) and Cap B (26 mL) solutions from PerSeptive Biosystems GmbH, and shaken for one hour. The resin was again washed with CH$_2$Cl$_2$ (×3) and ether (×3) and dried under vacuum overnight. The final loading was determined to be 50 μmol/g.

EXAMPLE 26

Synthesis of Oligonucleotides Incorporating Compounds 14 and 20

TABLE I

| SEQ ID NO: | ISIS # | Sequence (5'–3')[1] | U* = | Target |
|---|---|---|---|---|
| 1 | 22655-1 | TGC ATC CCC CAG GCC ACC AU* | cmpd 14 | CD54 |
| 1 | 22656-1 | TGC ATC CCC CAG GCC ACC AU* | cmpd 20 | CD54 |
| 2 | 27700-1 | <u>TCT GAG TAG CAG AGG AGC CU</u>* | cmpd 14 | CD54 |
| 2 | 27701-1 | <u>TCT GAG TAG CAG AGG AGC CU</u>* | cmpd 20 | CD54 |

[1]Underlined nucleosides contain 2'-O-(2-methoxyethyl) and all C's are 2'-O-(2-methoxyethyl)-5-methylcytidine.

Standard 2'-deoxy amidites (0.1M in CH$_3$CN, Perceptive Biosystems GmbH) were used in the synthesis of oligonucleotides having SEQ ID NO: 1 (ISIS 22655-1 and ISIS 22656-1) and oligonucleotides having SEQ ID NO: 2 (ISIS 27700-1 and ISIS 27701-1). Phosphoramidites 5'-O-DMT-2'-O-(2-methoxyethyl)-N$^6$-benzoyladenosine-3-O-amidite (RI Chemical), 5'-O-DMT-2'-D-(2-methoxyethyl)-N$^4$-benzoyl-5-methylcytidine-3'-O-amidite (RI Chemical, Lot #E805-P-17), 5'-O-DMTr-2'-O-(2-methoxyethyl)-N$^2$-isobutylguanosine-3'-O-amidite (RI Chemical, Lot #EMG-P-18U), and 5'-O-DMTr-2'-O-(2-methoxylethyl)-5-methyluridine-3'-O-amidite (RI Chemical, Lot #E1050-P-10) were used in the synthesis. The 2'-O-(2-methoxyethyl) phosphoramidites were dissolved in CH$_3$CN (100 mg amidite/1 mL CH$_3$CN). Compound 14 was used as the LCAA-CPG solid support in the synthesis of SEQ ID NO: 1 (ISIS 22655-1) and SEQ ID NO: 2 (ISIS 27700-1). Compound 20 was used as the LCAA-CPG solid support in the synthesis of SEQ ID NO: 1 (ISIS 22656-1) and SEQ ID NO: 2 (ISIS 27701-1).

Each oligonucleotide was synthesized on an approximately 1×2 mol synthesis scale, requiring about 50 mg of derivatized LCAA-CPG for each synthesis. Deprotection of the 5'-hydroxyl groups having a DMT protecting group was performed using trichloroacetic acid (1.2 mL 3% in $CH_2Cl_2$) per phosphoramidite coupling followed by an $CH_3CN$ wash. To the detritylated LCAA-CPG amidite (0.3 mL) and 1-H-tetrazole (0.6 mL, 0.49M) in $CH_3CN$ were then delivered. The coupling time was approximately 5 minutes for standard 2'-deoxy phosphoramidites and approximately 14 minutes for novel phosphoramidites. Amidite was delivered twice per coupling. Excess amidite was washed away with $CH_3CN$. (2R,8aS)-(+)-(10-camphorsulfonyl) oxaziridine (0.5 mL, 36M) in $CH_3CN$ were delivered over four minutes to oxidize the phosphodiester linkages, followed by another $CH_3CN$ wash. Unreacted functionalities were capped with a 50:50 mixture (0.2 mL/coupling) of acetic anhydride in tetrahydrofuran (THF) and 1-methylimidazole in THF, followed by an anhydrous $CH_3CN$ wash. Synthesis cycles (including: detritylation, amidite coupling, oxidation and capping) continued until the desired length was reached. Trityl yields were followed by the trityl monitor during the duration of each synthesis. The final DMT group was left intact.

After synthesis oligonucleotides were deprotected and cleaved from the solid support using aqueous concentrated ammonium hydroxide at 55° C. for approximately 16 hours. Oligonucleotides were then filtered from the solid support and ammonia was evaporated in a Savant AS160 Automatic Speed Vac.

The oligonucleotide crude yield was measured on a Hewlett Packard 8452A Diode Array spectrophotometer at 260 nm. The crude samples were then analyzed for integrity by mass spectrometry (Hewlett Packard electrospray mass spectrometer), capillary gel electrophoresis (Beckmann P/ACE system 5000), and high performance liquid chromatography (Waters 600E HPLC system with Waters 991 detector). Trityl-on oligonucleotides were purified by HPLC (Waters) using reverse phase protocols (HPLC conditions: Waters 600E with 991 detector; Waters $C_4$ Delta Pak column (7.8×300 mm, 15, 300 Å); solvent A=50 mM triethylammonium acetate, pH=7.0; solvent B=100% $CH_3CN$; 2.5 mL/minute flow rate; gradient: 5% B for first five minutes with a linear increase in B to 60% over the next 55 minutes). Appropriate HPLC fractions were collected, evaporated to completeness, detritylated in 80% acetic acid in water at room temperature for approximately one hour, and then evaporated once again. To remove free trityl and excess salt, detritylated oligos were dissolved in aqueous ammonia and passed through Sephadex G-25 resin, using water as solvent. Samples were collected by a Pharmacia LKB Super Frac fraction collector. The purified oligonucleotides were then analyzed for purity by CGE, MS, and HPLC (flow rate: 1.5 mL/minute, Waters Delta Pak $C_4$ column, 3.9×300 mm, 15, 300 Å). Final yields were determined by a spectrophotometer at 260 nm.

TABLE II

| SEQ ID NO: –U* | Crude Yield (@ 260 nm) | Final Yield (@ 260 nm) | HPLC Retention Time (min)[2] | Expected Mass (g/mol) | Observed Mass (g/mol) |
|---|---|---|---|---|---|
| 1–14 | 280 ODs | 104 ODs | 31.18 | 6273.12 | 6270.53 |
| 1–20 | 324 ODs | 180 ODs | 37.57 | 6323.27 | 6320.99 |
| 2–14 | 321 ODs | 137 ODs | 36.08 | 7935.93 | 7929.39 |
| 2–20 | 303 ODs | 165 ODs | 36.31 | 7986.09 | 7984.52 |

[2] = HPLC conditions: Waters 600E with 991 detector HPLC system; Waters $C_4$ Delta Pak column (3.9 × 300 mm, 15, 300 Å); solvent A = 50 mM triethylammonium acetate, pH = 7.0; solvent B = 100% $CH_3CN$; 1.5 mL/min. flow rate; gradient: 5% B for first five minutes with a linear increase in B to 60% over the next 55 minutes. U* indicates the compound in the specific sequence e.g. both compounds 14 and 20 were used in each of SEQ ID NOs. 1 and 2.

EXAMPLE 27

Synthesis of Oligonucleotides Incorporating Compounds 3, 6, 9 and 12

Four oligonucleotides having SEQ ID NO: 3 (ISIS 25152-1, ISIS 25153-1, ISIS 25154-1 and ISIS 25155-1) were synthesized on a Millipore Expedite 8901 Nucleic Acid Synthesis System. The following modified amidites were used to prepare these oligonucleotides: 2'-O-methoxyethyl-5-thymidine (RI Chemical lot #E1050-P-10), 2'-O-methoxyethyl-5-methylcytidine (lot #S1941/RS), 2'-O-methoxyethyl-adenosine (RI Chemical, lot #EMA-P-14), and 2'-O-methoxy-ethylguanosine (RI Chemical, lot #EMG-P-18U). Compound 3 was used as the LCAA-CPG solid support for the synthesis of ISIS 25152-1, compound 6 for ISIS 25153-1, compound 9 for ISIS 25154-1, and compound 12 for ISIS 25155-1.

The required amounts of the amidites were placed in dried vials, dissolved in $CH_3CN$ (modified nucleosides were prepared to give 100 mg/mL), and connected to the appropriate ports on a Millipore Expedite™ Nucleic Acid Synthesis System. solid support resin (60 mg) was used in each column for 2×1 µmole scale synthesis. The synthesis was run using the standard phosphoramidite protocols utilizing (+)-(2R,8aS)-10(camphorylsulfonyl)oxaziridine (CSO) for oxidation steps. The trityl reports indicated normal coupling results.

After synthesis, the oligonucleotides were deprotected with concentrated ammonium hydroxide (aq) at 55° C. for approximately 16 hours, concentrated using a Savant AS160 Automatic Speedvac, (to remove ammonia) and filtered to remove the CPG-resin. The crude samples were analyzed by MS, HPLC, and CE followed by purification on a Waters 600E HPLC system with a 991 detector (Waters C4 preparative scale column) using the following solvents: A: 50 mM TEA-Ac, pH 7.0 and B: $CH_3CN$. The purified oligonucleotides were detritylated with 80% acetic acid at room temperature for approximately 30 minutes followed by concentrating under vacuum and drying. The oligonucleotides were dissolved in concentrated ammonium hydroxide and run through a column containing Sephadex G-25 using water as the solvent and a Pharmacia LKB SuperFrac fraction collector. The resulting purified oligonucleotides were evaporated and analyzed by MS, CE and HPLC.

TABLE III

| SEQ ID NO: | ISIS # | Sequence (5'–3')[1] | Modification T* = |
|---|---|---|---|
| 3 | 25152-1 | TCT GAG TAG CAG AGG AGC CT* | compound 3 |
| 3 | 25153-1 | TCT GAG TAG CAG AGG AGC CT* | compound 6 |
| 3 | 25154-1 | TCT GAG TAG CAG AGG AGC CT* | compound 9 |
| 3 | 25155-1 | TCT GAG TAG CAG AGG AGC CT* | compound 12 |

All nucleotides are 2'-O-methoxyethel (MOE) except for T*; backbone is fully phosphodiester; and heterocycles are unmodified. Are C's are 5-Me, as is the case below for

TABLE IV

| SEQ ID NO. -T* | Crude Yield (@ 260 nm) | Final Yield (@ 260 nm) | HPLC/CE Retention Time (min)[2] | Expected Mass (g/mol) | Observed Mass (g/mol) |
|---|---|---|---|---|---|
| 3–3 | 625 ODs | 288 ODs | 27.7/7.30 | 7982.73 | 7982.59 |
| 3–6 | 430 ODs | 310 ODs | 28.35/7.32 | 7982.73 | 7982.15 |
| 3–9 | 480 ODs | 368 ODs | 27.65/7.47 | 7988.76 | 7988.41 |
| 3–12 | 663 ODs | 255 ODs | 30.10/7.45 | 8002.16 | 8001.72 |

EXAMPLE 28

Synthesis of Oligonucleotides Incorporating Compounds 16 (Palmityl) and 21 (Ibuprofenyl)

Two oligonucleotides were synthesized having SEQ ID NO: 4 (ISIS 32361-1 and ISIS 32362-1) on a Millipore Expedite 8901 Nucleic Acid Synthesis System. Compound 16 was used as the A-CPG solid support for the synthesis of ISIS 32361-1 and also a palmityl TC dimer. Compound 21 was used as the LCAA-CPG solid support for the synthesis of ISIS 32362-1 and an ibuprofenyl TC dimer. The following modified amidites were used in the above sequences: 5'-DMT-2'-O-methoxyethyl-5-methyluridine beta-cyanoethylphosphoramidite (PrOligo, Lot No. S 3044), 2'-O-(2-methoxyethyl)-5-Me-C Bz amidite (BSR-1026-89), 2'-O-MOE A phosphoramidite (Pharmacia Biotech, Lot No. 311119), and 2'-O-(2-methoxyethyl)-(iBu)G amidite (BSR-1026-84).

The required amounts of the amidites were placed in dried vials, dissolved in $CH_3CN$ (modified nucleosides prepared to be 100 mg/mL), and connected to the appropriate ports on a Millipore Expedite™ Nucleic Acid Synthesis System. Solid support resin (60 mg) was used in each column for 2×1 μmol scale synthesis. The synthesis was run using standard phosphoramidite protocols utilizing CSO for oxidation steps. The trityl reports indicated normal coupling results. After synthesis, the oligonucleotides were deprotected with concentrated ammonium hydroxide (aq) at 55° C. for approximately 16 hours. Then they were evaporated, using a Savant AS160 Automatic SpeedVac, (to remove ammonia) and filtered to remove the CPG-resin.

The crude samples were analyzed, purified and deprotected as illustrated above in Example 27. The dried oligonucleotides were dissolved in concentrated ammonium hydroxide and run through a column containing Sephadex G-25 with water used as eluent. The dimers were each further purified using a Dowex and then a Chelex column for NMR studies. The resulting purified oligonucleotides were evaporated and analyzed by MS, CE (MDQ) and HPLC.

TABLE V

| SEQ ID NO: | ISIS # | Sequence (5'–3')[1] | Modification C* = |
|---|---|---|---|
| 4 | 32361-1 | TCT GAG TAG CAG AGG AGC TC* | compound 16 |
| 4 | 32362-1 | TCT GAG TAG CAG AGG AGC TC* | compound 21 |
| dimer | | TC* (16) | compound 16 |
| dimer | | TC* (21) | compound 21 |

All nucleotides are 2'-O-methoxyethyl (MOE) except for C*; backbone is fully phosphodiester; and heterocycles are unmodified except all C's are 5-methylcytidine.

TABLE VI

| SEQ ID NO: -C* | Crude Yield (@ 260 nm) | Final Yield (@ 260 nm) | HPLC/CE Retention Time (min)[2] | Expected Mass (g/mol) | Observed Mass (g/mol) |
|---|---|---|---|---|---|
| 4–16 | 498 ODs | 95 ODs | 45.71/4.325 | 7987.59 | 7984.86 |
| 4–21 | 649 ODs | 122 ODs | 32.45/4.500 | 7937.48 | 7932.63 |
| dimer-16 | 33 ODs | 22 ODs | n/a | $M^{2-}$ 593.6 | $M^{2-}$ 592.7 |
| dimer-21 | 30 ODs | 20 ODs | n/a | $M^{2-}$ 568.5 | $M^{2-}$ 567.5 |

EXAMPLE 29

Synthesis of Oligonucleotides Incorporating Compounds 18 (Palmityl) and 20 (Ibuprofenyl)

Following the procedures illustrated in the examples above compounds 18 and 20 were incorporated into oligonucleotides SEQ ID NO: 4 as illustrated in Table VII. Compound 4-18 is ISIS 32361-1 and compound 4-20 is ISIS 32362-1.

TABLE VII

| SEQ ID NO: | Sequence[4] | Backbone | ODs (@ 260 nm) |
|---|---|---|---|
| 4–18 | TC$^{5Me}$T GAG TAG C$^{5Me}$AG AGG AGC$^{5Me}$ TC* | P=O | 30 |
| 4–20 | TC$^{5Me}$T GAG TAG C$^{5Me}$AG AGG AGC$^{5Me}$ TC** | P=O | 30 |

[4]All nucleotides contain the 2'-O-Methoxyethyl group (except for the 3'-terminal C). All C's are 5-methyl-C's. C* = 3'-O-Palmityl-aminohexyl-cytidine. C** = 3'-O-Ibuprofenyl-aminohexyl-cytidine.

EXAMPLE 30

Synthesis of Oligonucleotides Incorporating Compound (26)

Compound 26 was incorporated into SEQ ID NO: 4 (ISIS 29782-1) as the 3'-terminal nucleoside. The synthesis was performed on a Millipore Expedite 8901 nucleic acid Synthesizer. The incorporation of compound 26 into an oligonucleotide allows the conjugation at the 3'-end of the oligonucleotide via the 2'-aminopropyl group.

TABLE VIII

| SEQ ID NO: –C* | Sequence (5'–3')[5] | C* = | Target |
|---|---|---|---|
| 4–26 | TCT GAG TAG CAG AGG AGC TC* | compound 26 | CD54 |

[5]All nucleosides contain 2'-O-(2-methoxyethyl) except C*. All C's are 2'-O-(2-methoxyethyl)-5-methylcytidine.

Nucleosides were purchased from commercial sources: 5'-ODMT-2'-O-(2-methoxyethyl)-N[6]-benzoyladenosine-3-O-amidite (RI Chemical, Lot #EMA-P-09); 5'-O-DMT-2'-O-(2-methoxyethyl)-N[4]-benzoyl-5-methylcytidine-3'-O-amidite (RI Chemical, Lot #E805-P-17); 5'-ODMT-2'-O-(2-methoxyethyl)-N[2]-isobutylguanosine-3'-O-amidite (Pharmacia Biotech 27-0022-42), and 5'-O-DMT-2'-O-(2-methoxylethyl)-5-methyluridine-3'-O-amidite (Perceptive Biosystems). The 2'-O-(2-methoxyethyl) phosphoramidities were dissolved in $CH_3CN$ (100 mg amidite/1 mL $CH_3CN$). Compound 26 was used as the LCAA-CPG solid support in the synthesis which effected its incorporation at the 3' end of the oligonucleotide.

The oligonucleotide was synthesized on an approximately 2×20 μmol synthesis scale, requiring approximately 333 mg of derivatized LCAA-CPG each. The DMT protecting groups on the solid support were removed with tRI Chemicalhloroacetic acid (10.6 mL, 3%) in $CH_2Cl_2$ per coupling followed by an $CH_3CN$ wash. To the detritylated LCAA-CPG, amidite (1.20 mL) and 1-H-tetrazole (1.80 mL, 0.49M) in $CH_3CN$ were then delivered (total coupling time of approximately 24 minutes for novel amidites.) The amidite reagent was delivered four times per coupling. Excess amidite was washed away with $CH_3CN$. (2R,8aS)-(+)-(10-camphorsulfonyl) oxaziridine (2.40 mL 36.4M) in anhydrous $CH_3CN$ was delivered over four minutes to oxidize the phospodiester linkages, followed by another anhydrous $CH_3CN$ wash. Unreacted functionalities were capped with a 50:50 mixture (1.40 mL/coupling) of acetic anhydride in tetrahydrofuran (THF) and 1-methylimidazole in THF, followed by an anhydrous $CH_3CN$ wash. Trityl yields were followed by the trityl monitor during the duration of a synthesis. The final DMT group was left intact.

Following the synthesis, the oligonucleotides were deprotected and removed from the solid support with concentrated ammonium hydroxide (aq) and methylamine (Aldrich Chemicals, 10%, 40 wt. % solution in water) at 55° C. for approximately 16 hours. They were then filtered from the solid support and ammonia was evaporated in a Savant AS160 Automatic Speed Vac.

Oligonucleotide crude yield was measured on a Hewlett Packard 8452A Diode Array spectrophotometer at 260 nm. The crude samples were then analyzed for integrity by mass spectrometry (Hewlett Packard electrospray mass spectrometer), capillary gel electrophoresis (Beckmann P/ACE system 5000), and high performance liquid chromatography (Waters 600E HPLC system with Waters 991 detector). Trityl-on oligonucleotides were purified on the Waters HPLC system by reverse phase as illustrated above. (HPLC conditions: waters C, Delta Pak column (25×100 mm, 15 , 300 Å); solvent A=50 mM triethylammonium acetate, pH=7.0; solvent B=100% $CH_3CN$; 5.0 mL/min. flow rate; gradient: 5% B for first five minutes with a linear increase in B to 60% over the next 55 minutes.) Appropriate HPLC fractions were collected, evaporated to completeness, detritylated in 80% acetic acid in water at room temperature for approximately one hour, and then evaporated once again. To remove free trityl and excess salt, detritylated oligos were dissolved in aqueous ammonia and passed through Sephadex G-25 resin, using water as solvent. Samples were collected by a Pharmacia LKB Super Frac fraction collector. The purified oligonucleotides were then analyzed for purity by CGE, MS, and HPLC (flow rate: 1.5 mL/min., Waters Delta Pak $C_4$ column, 3.9×300 mm, 15, 300 Å). Final yields were determined by a spectrophotometer at 260 nm.

TABLE IX

| SEQ ID NO: –C* | Crude Yield (@ 260 nm) | Final Yield (@ 260 nm) | HPLC Retention Time (min) | Expected Mass (g/mol) | Observed Mass (g/mol) |
|---|---|---|---|---|---|
| 4–26 | 6902 ODs | 3100 ODs | 22.19 | 7705.25 | 7704.32 |

EXAMPLE 31

Ligand Conjugation to an Oligonucleotide Containing an Aminopropyl Linker

Oligonucleotide having SEQ ID NO: 4 and further having compound 26 attached as the 3'-nucleoside (4-26) was used as a substrate for post synthetic conjugation of functional groups. Four different functional groups ($PEG_{2000}$, $PEG_{5000}$, Biotin, and Pyrene) were conjugated and the respective oligonucleotides were purified. The groups are attached at the 3' end of the oligonucleotide via a 2-O-aminohexyl linking group.

TABLE X

| SEQ ID NO: | Sequence (5'–3') | Modification | Target |
|---|---|---|---|
| 4–26 | TCT GAG TAG CAG AGG AGC TC* | C* = 2'-O-$PEG_{2000}$-aninopropylcytidine | CD54 |
| 4–26 | TCT GAG TAG CAG AGG AGC TC* | C* = 2'-O-$PEG_{5000}$-aminopropylcytidine | CD54 |
| 4–26 | TCT GAG TAG CAG AGG AGC TC* | C* = 2'-O-biotinylaminopropylcytidine | CD54 |
| 4–26 | TCT GAG TAG CAG AGG AGC TC* | C* = 2'-O-pyrenylpropyl carbonylaminopropylcytidine | CD54 |

All nucleotides are 2'-O-MOE modified except C*.

All C's are 2'-O-(2-methoxyethyl)-5-methylcytidine.

A) Procedure for $PEG_{2000}$, ISIS 30130-1

ISIS 29782-1 (100 ODs) contained in a closed-capped 13×100 mm pyrex test tube was dried down in a speed vac overnight. After drying, 200 mg $PEG_{2000}$ and sodium bicarbonate (400 μL, 0.2M) were added to the oligonucleotide with shaking overnight. The reaction mixture was dissolved in water (3 mL) and purified by HPLC (HPLC conditions: Waters $C_4$ Delta Pak column (7.8×300 mm, 15, 300 Å); solvent A=50 mM triethylammonium acetate, pH=7.0; solvent B=100% $CH_3CN$; flow rate 2.5 mL/minute; gradient: 5% B for first five minutes with a linear increase in B to 60% over the next 55 minutes. The fractions of interest were collected and evaporated. To remove salt and free $PEG_{2000}$ the oligonucleotide was passed through Sephadex G-25 resin and further purified by HPLC (conditions: solvent A=50 mM triethylammonium acetate, pH=7.0; solvent B=100% $CH_3CN$; solvent $C=H_2O$; flow rate 2.5 mL/minute; gradient: 100% A for first 10 minutes with a linear increase in C to 100% over the next 5 minutes, remaining constant for the next 60 minutes, followed by a linear increase in B to 100% for 20 minutes.) ISIS 30130-1 was analyzed for purity by Mass Spec, HPLC, and CGE. Final yield was determined by spectrophotometer at 260 nm.

B) Procedure for $PEG_{5000}$, ISIS 30131-1

ISIS 29782-1 (100 ODs) contained in a closed-capped 13×100 mm pyrex test tube was dried down in a speed vac overnight. After drying, 150 mg $PEG_{5000}$ and sodium bicarbonate (350 μL, 0.2M) was added with shaking overnight. The reaction mixture was dissolved in water (3 mL) and purified by HPLC as illustrated above. The final oligonucleotide was analyzed for purity by Mass Spec, HPLC, and CGE. Final yield was determined by spectrophotometer at 260 nm.

C) Procedure for Biotin, ISIS 30132-1

ISIS 29782-1 (100 ODs) contained in a closed-capped 13×100 mm pyrex test tube was dried down in a speed vac overnight. After drying, 20 mg (+)-biotin N-succinimidyl ester (Fluka 14405) and sodium bicarbonate (200 μL 0.2M) was added to the oligonucleotide with shaking overnight. The mixture was shaken overnight. The reaction mixture was dissolved in water (3 mL) and purified by HPLC as illustrated above. The final oligonucleotide was analyzed for purity by Mass Spec, HPLC, and CGE. Final yield was determined by spectrophotometer at 260 nm.

D) Procedure for Pyrene, ISIS 30133-1

ISIS 29782-1 (100 ODs) contained in a closed-capped 13×100 mm pyrex test tube was dried down in a speed vac overnight. After drying, 20 mg succinimidyl-1-pyrene butyrate (Molecular Probes, Lot #2721-3) and sodium bicarbonate (200 μL, 0.2M) was added to the oligonucleotide. The reaction mixture was dissolved in water (3 mL) and purified by HPLC as illustrated above. The final oligonucleotide was analyzed for purity by Mass Spec, HPLC, and CGE. Final yield was determined by spectrophotometer at 260 nm.

TABLE XI

| ISIS # | Starting Yield (@ 260 nm) | Final Yield (@ 260 nm) | HPLC Retention Time (min)$^2$ | Expected Mass (g/mol) | Observed Mass (g/mol) |
|---|---|---|---|---|---|
| 30130-1 | 100 ODs | 28 ODs | 32.61 | N/A | N/A |
| 30131-1 | 100 ODs | 30 ODs | 39.14 | N/A | N/A |
| 30132-1 | 100 ODs | 26 ODs | 24.17 | 7932.56 | 7930.49 |
| 30133-1 | 100 ODs | 25 ODs | 22.43 | 7976.59 | 7976.63 |

EXAMPLE 32

3'-O-Hexylaminobenzylpenicillinyl-5'-O-DMT-5-methyluridine (22)

Benzylpenicillin potassium salt (0.56 g, 1.52 mmol, Fluka) was suspended in DMF (6 mL) at room temperature under an atmosphere of argon. 4-Methylmorpholine (0.33 mL, 3.04 mmol) and TBTU (0.49 g, 1.52 mmol) were added and the suspension became a clear orange solution. 3'-O-Hexylamino-5'-O-DMT-5-methyluridine (1.0 g, 1.52 mmol) was added and the mixture with stirring overnight. The mixture was evaporated under high vacuum to give the title compound.

EXAMPLE 33

3'-O-Hexylaminophenoxymethylpenicillinyl-5'-O-DMT-5-methyluridine (23)

Phenoxymethylpenicillinic acid (1.06 g, 3.03 mmol, Sigma) was dissolved in DMF (10 mL) at room temperature under an atmosphere of argon. 4-Methylmorpholine (0.67 mL, 6.06 mmol) and TBTU (0.97 g, 3.03 mmol) were added followed by 3'-O-hexylamino-5'-O-DMT-5-methyluridine (2.0 g, 3.03 mmol). The mixture was stirred overnight and then evaporated. The material was purified by silica gel column chromatography using ethyl acetate:triethylamine (100/1, v/v) as the eluant to give 0.496 g of the title compound.

EXAMPLE 34

Succinimidylphenoxymethylpenicillin (24)

Phenoxymethylpenicillinic acid (1.00 g, 2.85 mmol, Sigma) was suspended in $CH_2Cl_2$ (10 mL) at room temperature under an atmosphere of argon. Dimethylaminopyridine (DMAP) (0.070 g, 0.57 mmol) was added and the suspension dissolved into a clear solution. 1,3-Dicyclohexylcarbodiimide (0.59 g, 2.85 mmol) was added with stirring for about 30 minutes followed by addition of N-hydroxysuccinimide (0.33 g, 2.85 mmol). The suspension stirred for about 3 hours and filtered to remove DCU. The filter cake was washed with $CH_2Cl_2$ and the combined organic phase was washed twice with water (to remove DMAP). The organic-phase was then dried over sodium sulfate and evaporated to a brown foam to give 1.26 g (98%) of the title compound. MS (ES$^+$) calculated for $C_{20}H_{21}N_3O_7S$ 447.1. Observed MH$^+$ 449.1 (minor peak) and MH$^{2+}$ 224.9 (major peak).

EXAMPLE 35

Preparation of Phenoxymethylpenicillinyl Conjugated Oligonucleotide SEQ ID NO: 5

5'-Hexanolamine-phosphodiester-TGC ATC CCC CAG GCC ACC AT, SEQ ID NO: 5, (ISIS 3082) was prepared following standard methods and techniques using an automated DNA synthesizer. At the last step in synthesis 5'-amino-modifier C6 phosphoramidite (Glen Research, Sterling, Va.) was used to introduce the aminohexylphosphodiester attached to the 5'-end of the oligomer. All internucleotide linkages were P=O (phosphodiester) linkages and they were introduced by CSO oxidation protocol. The final oligonucleotide was deprotected and HPLC purified to give the 5'-aminohexyl phosphodiester linked oligonucleotide.

The aminohexyl linked oligonucleotide was dried to a white powder and dissolved in sodium bicarbonate (200 μL, 0.1 M, aq) at room temperature. Compound 24 (25 mg, 0.06 mmol) in DMF (200 μL) was added with vortexing and the mixture was kept overnight at room temperature. The mixture was run through a sephadex G-25 column using water as the solvent. The collected fractions were filtered through a syringe disk filter and purified by prep-HPLC using a C-4 column as illustrated in the previous examples. The collected fractions were concentrated and dried to give the title oligonucleotide.

EXAMPLE 36

Preparation of Phenoxymethylpenicillinyl Conjugated Full 2'-O-MOE Oligonucleotide SEQ ID NO: 3

5'-Hexanolamine-phosphodiester-TC$^{5M}$T GAG TAG C$^{5M}$AG AGG AGC$^{5M}$ C$^{5M}$T, SEQ ID NO: 3, (ISIS 11158) was prepared following standard methods and techniques using an automated DNA synthesizer. At the last step in the synthesis 5'-amino-modifier C6 phosphoramidite (Glen Research, Sterling, Va.) was used to introduce the aminohexylphosphodiester attached to the 5'-end of the oligomer. All internucleotide linkages were P=O (phosphodiester) linkages introduced by CSO oxidation protocol. The final oligonucleotide was deprotected and HPLC purified to give the 5'-aminohexyl phosphodiester linked oligonucleotide.

The aminohexyl linked oligonucleotide (50 OD's) was dissolved in sodium bicarbonate (200 µl, 0.1 M, aq) at room temperature. Compound 24 (25 mg, 0.06 mmol) in DMF (100 µL) was added, the resulting suspension was vortexed and allowed to stand overnight at room temperature. The mixture was run through a sephadex G-25 column using water as the solvent. The collected fractions were filtered through a syringe disk filter and purified through a prep-HPLC using a C-4 column as illustrated above. These collected fractions were then evaporated to give the title oligonucleotide.

EXAMPLE 37

Preparation of 3'-O-Hexylaminoaspirinyl-5'-O-DMT-5-methyluridine 25

Acetyl salicylic acid (aspirin) (0.55 g, 3.03 mmol) was dissolved in DMF (10 mL) at room temperature under an atmosphere of argon. 4-Methylmorpholine (0.67 mL, 6.06 mmol) and TBTU (0.97 g, 3.03 mmol) were added followed by 3'-O-hexylamino-5'-O-DMT-5-methyluridine (2.00 g, 3.03 mmol). The mixture was stirred overnight and concentrated. The crude material was purified by silica gel column chromatography using ethyl acetate:hexanes:triethylamine (75/25/1, v/v/v) as the eluant to give 1.36 g (55%) of the title compound as a clear oil. MS (ES$^+$) calculated for $C_{46}H_{51}N_3O_{11}$ 821.4; observed MH$^+$+Na 844.4.

EXAMPLE 38

3'-O-Hexylaminoaspirinyl-2'-O-succinyl-5'-O-DMT-5-methyluridine 26

Compound 25 (1.31 g, 1.59 mmol) was dissolved in 1,2-dichloroethane (4 mL) at room temperature under an atmosphere of argon. Triethylamine (0.22 mL, 1.59 mmol), DMAP (0.097 g, 0.80 mmol), and succinic anhydride (0.239 g, 2.38 mmol) were added and the mixture was placed in a 50° C. heating block overnight to give following purification the title compound.

EXAMPLE 40

Succinimidylaspirin 27

Acetylsalicylic acid (1.00 g, 5.55 mmol) and DMAP (0.136 g, 1.11 mmol) were dissolved in $CH_2Cl_2$ (10 mL) at room temperature under an atmosphere of argon. DCC (1.145 g, 5.55 mmol) was added, the mixture was stirred for about 5 minutes and N-hydroxysuccinimide (0.639 g, 5.55 mmol) was added. The mixture stirred for 4 hours, filtered, $CH_2Cl_2$ was added and the mixture was washed twice with water. The organic phase was dried over sodium sulfate, concentrated and dried to give 1.58 g (100%) of the title compound.

EXAMPLE 41

Preparation of Aspirinyl Conjugated Oligonucleotide SEQ ID NO: 3

5'-Hexanolamine-phosphodiester-TC$^{5M}$T GAG TAG C$^{5M}$AG AGG AGC$^{5M}$ C$^{5M}$T, SEQ ID NO: 3, prepared as per Example 36, (ISIS 11158)(100 OD's) (dried to a white powder) was dissolved in sodium bicarbonate(0.1 M, 200 µL, aq) at room temperature. Compound 38 (25 mg, 0.06 mmol) in DMF (400 µL) was added and the resulting suspension was vortexed and then shaken overnight at room temperature. The resulting material was run through a sephadex G-25 column using water as the eluent. The collected fractions were filtered through a syringe disk filter and purified through a prep-HPLC C-4 column as illustrated above to give after concentration and drying the title oligonucleotide.

EXAMPLE 42

Binding Affinity of Oligonucleotides to Human Serum Albumin (BSA)

Binding Curves:

The 5' end of ISIS-27700 was end labeled with $^{32}$P using T4 polynucleotide kinase and standard procedures. Unincorporated label was removed using a G25 column and was confirmed by polyacrylamide gel electrophoresis. A fixed concentration of labeled oligonucleotide (50 nM) was incubated with increasing concentrations of human serum albumin (Fraction V, essentially Fatty Acid Free, essentially globulin free, Sigma Chemical Company, St. Louis, Mo.) and incubated at 25° for one hour in PBS plus 0.1 mM EDTA and 0.005% Tween 80. Experiments with longer incubation times demonstrated that full equilibrium was achieved in less than one hour.

Albumin-oligonucleotide mixtures were placed on membranes (Ultrafree-MC 30000, Millipore) and spun very gently at 3000 rpm (725×g) for 3–6 minutes until ~20% of the volume had passed through the filter. Aliquots of the initial mix (before filtration) and the filtrates were counted in a scintillation counter. After appropriate correction for background, the concentration of free and bound oligonucleotide was calculated.

The low concentration of oligonucleotide, relative to albumin, allows for detection of binding to only the tightest binding site on the albumin. Thus, the fraction of bound oligonucleotide was plotted versus the total albumin concentration and data were fit to a two state model:

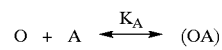

where O is unbound oligonucleotide, A is unbound albumin, (OA) is the oligonucleotide-albumin complex and $K_A$ is the equilibrium association constant.

Capacity Curves:

Capacity curves were measured using a technique similar to that used for the binding curves except a fixed concentration of albumin (50 µM) was employed and the concentration of labeled oligonucleotide was varied. The average number of moles of oligonucleotide bound per mole of protein, $n_L$, was plotted versus free oligonucleotide concentration and fit to a model with two classes of binding sites, each with $n_i$ binding sites per protein and association constant, $K_i$.

Results:

Oligonucleotides tested are listed in Table XII. A comparison was made between an unmodified deoxy diester oligonucleotide (8651) and its 3' ibuprofen conjugate (22655) and a uniformly 2'-O-methoxy-ethyl modified phosphodiester oligonucleotide (11158) and its 3' ibuprofen conjugate (27700). As seen in FIG. 1 and Table XIII, binding of the unconjugated controls was very weak ($K_D$>200 μM). Addition of the ibuprofen conjugate increased the affinity substantially. Binding of the phosphodiester conjugates was comparable to that of phosphorothioate DNA oligonucleotides which are among the tightest binding of all modified oligonucleotides (data not shown). The capacity of HSA for the ibuprofen conjugate was also measured. Binding ratios of 0.75:1 (oligonucleotide:albumin) were achieved for the conjugate. This contrasts to unconjugated oligonucleotides where maximum capacity observed was 0.2:1.

Conclusion:

Phosphodiester oligonucleotides (both 2'-deoxy and 2'-O-methoxyethyl) bound to HSA with weak affinity ($K_D$>200 μM). Phosphorothioate oligonucleotides, in contrast, had greater affinities ($K_D$ 3–30 μM). Addition of an ibuprofen conjugate to the 3' end of a phosphodiester oligonucleotide increased the affinity into the range typical for phosphorothioate oligonucleotides. It was seen that the capacity of HSA for the ibuprofen conjugate was much greater than that for unconjugated oligonucleotides.

TABLE XII

| SEQ ID NO: | ISIS # | Sequence | Chemistry | Conjugate |
|---|---|---|---|---|
| 3 | 27700 | TC*T GAG TAG C*AG AGG AGC* C*T | full MOE PO | 3'-ibuprofen |
| 4 | 11158 | TC*T GAG TAG C*AG AGG AGC* TC | full MOE PO | 3'-OH |
| 4 | 3067 | TCT GAG TAG CAG AGG AGC TC | full deoxy PS | 3'-OH |
| 5 | 22655 | TGC ATC CCC CAG GCC ACC AT | full deoxy PO | 3'-ibuprofen |
| 5 | 8651 | TGC ATC CCC CAG GCC ACC AT | full deoxy PO | 3'-OH |
| 5 | 3082 | TGC ATC CCC CAG GCC ACC AT | full deoxy PS | 3'-OH |

C* = 5-methyl cytosine.

TABLE XIII

Equilibrium dissociation constants for modified oligonucleotides binding to HSA.

| SEQ ID NO: | ISIS # | $K_D$ (μM) |
|---|---|---|
| 3 | 27700 | 8 |
| 4 | 11158 | >400 |
| 4 | 3067 | 7 |
| 5 | 22655 | 12 |
| 5 | 8651 | >200 |
| 5 | 3082 | 4 |

*Equilibrium constants were obtained from data in FIG. 1 as described in the text.

EXAMPLE 43

2'-O-Hexylaminopalmityl-5'-O-DMT-adenosine 28

2'-O-Hexylamino-5'-O-DMT-adenosine (3.00 g, 4.49 mmol) was dissolved in dichloromethane (60 mL, anh) at room temperature. Diisopropylamine (1.56 mL, 8.98 mmol) and palmitic acid pentafluorophenyl-ester (2.28 g, 5.39 mmol) were added and the mixture was stirred overnight and evaporated. The crude material was purified on a silica column (250 mL) using EtOAc-MeOH (95:5) as the eluent to give ~4.07 g (~100%) of the title compound.

EXAMPLE 44

2'-O-Hexylaminopalmityl-5'-O-DUT-$N^6$-benzoyladenosine 29

Compound 28 (4.00 g, 4.41 mmol) was dissolved in anhydrous pyridine (50 mL) at room temperature under argon. The solution was cooled to ice temperature and chlorotrimethylsilane (1.40 mL, 11.02 mmol) was added. The mixture stirred at ice temperature for ~30 minutes when benzoyl chloride (1.54 mL, 13.23 mmol) was added. Then it was allowed to warm to room temperature and stirred overnight. The mixture was cooled to ice temperature again and cold water (10 mL) was added. It was stirred for 15 minutes, then cold concentrated ammonium hydroxide (10 mL) was added. The mixture was allowed to warm to room temperature and stirred for 30 minutes, after which it was evaporated. Water (25 mL) was added and the mixture was extracted with ethyl acetate (×3). The organic phase was dried over anhydrous sodium sulfate and evaporated. A 300 mL silica column was run using ethyl acetate-hexanes (50:50) as the solvent to yield 1.83 g (41%) of the title compound.

EXAMPLE 45

2'-O-Hexylaminopalmityl-3'-O-succinate-5'-O-DMT-$N^6$-benzoyladenosine 30

Compound 29 (1.19 g, 1.18 mmol), succinic anhydride (0.22 g, 1.77 mmol), dimethylaminopyridine (0.09 g, 0.59 mmol), and triethylamine (0.21 mL, 1.18 mmol) were dissolved in 7 mL of 1,2-dichloroethane at room temperature. The reaction mixture (in a test-tube with a screw cap top) was placed in a heating block at 55° C. for 1 hour and then allowed to cool to room temperature overnight. TLC (EtOAc-hexanes, 90:10) showed the absence of starting material. Dichloromethane (70 mL) was added and the mixture was washed three times with 30 mL portions of cold 10% aqueous citric acid followed by three washes with 30 mL portions of water. The organic-phase was dried over anhydrous sodium sulfate and evaporated to afford 1.26 g (97%) of the title compound as a foam.

EXAMPLE 46

2'-O-Hexylaminopalmityl-3'-O-succinate-5'-O-DMT-$N^6$-benzoyl-adenosine LCAA-CPG 31

Compound 30 (1.24 g, 1.12 mmol) and 4-dimethylaminopyridine (0.14 g, 1.12 mmol) were dissolved in acetonitrile (7.0 mL, anh) at room temperature. In another flask, 2,2'-dithiobis-5-nitropyridine (0.35 g, 1.12 mmol) was dissolved in anhydrous acetonitrile (4.0 mL) and anhydrous dichloromethane (4.0 mL). This solution was then added to the first flask. In a third flask, triphenylphosphine (0.29 g, 1.12 mmol) was dissolved in acetonitrile (6.0 mL) and then combined with the first flask. Finally, acid-washed LCAA-CPG (4.86 g, 0.56 mmol) was added and the mixture was shaken for ~2 hours. The resulting resin was washed three times with dichloromethane and ether. Then it was combined with Cap A (21 mL) and Cap B (21 mL, solutions from PerSeptive Biosystems GmbH) and shaken for an additional hour. The resin was then washed again three times with dichloromethane and ether and placed under vacuum overnight to dry. The final loading was determined to be 48 umol/g.

EXAMPLE 47

2'-O-Hexylaminoibuprofenyl-5'-O-DMT-adenosine 32

2'-O-Hexylamino-5'-O-DMT-adenosine (3.00 g, 4.49 mmol, RI Chemical Company) was dissolved in anhydrous dichloromethane (40 mL) at room temperature. Diisopropylamine (1.56 mL, 8.98 mmol) and ibuprofen-pentafluorophenylester (2.01 g, 5.39 mmol, Example 21) were added and the mixture stirred overnight and evaporated. The crude material was evaporated and purified over a 250 mL silica column using EtOAc-MeOH (95:5) as the solvent to give 2.89 g (75%) of the title compound.

EXAMPLE 48

2'-O-Hexylaminoibuprofenyl-5'-O-DMT-N-benzoyladenosine 33

Compound 32 (2.87 g, 3.35 mmol) was dissolved in anhydrous pyridine (50 mL) at room temperature under Ar(g). The solution was cooled to ice temperature and chlorotrimethylsilane (1.06 mL, 8.38 mmol) was added. The mixture stirred at ice temperature for ~30 min. and then benzoyl chloride (1.17 mL, 10.05 mmol) was added. The mixture was allowed to warm to room temperature and stirred overnight. The mixture was cooled to ice temperature again and cold water (10 mL) was added with stirring for 15 minutes. Cold concentrated ammonium hydroxide (10 mL) was then added. The mixture was allowed to warm to room temperature and stirred for 30 minutes and evaporated. Water (25 mL) was added and the mixture was extracted with ethyl acetate (×3). The organic phase was dried over sodium sulfate and evaporated. The resulting material was purified using a 200 mL silica column with ethyl acetate-hexanes (90:10) as the eluant to give 2.50 g (78%) of the title compound.

EXAMPLE 49

2'-O-Hexylaminoibuprofenyl-3'-O-succinate-5'-O-DMT-$N^6$-benzoyladenosine 34

Compound 33 (2.00 g, 2.08 mmol), succinic anhydride (0.312 g, 3.12 mmol), dimethylaminopyridine (0.127 g, 1.04 mmol), and triethylamine (0.29 mL, 2.08 mmol) were dissolved in 1,2-dichloroethane (9 mL) at room temperature. The reaction mixture (in a test-tube with a screw cap top) was placed in a heating block at 55° C. for 1 hour and then allowed to cool to room temperature overnight. TLC (EtOAc-MeOH, 90:10) showed the absence of starting material. Dichloromethane (90 mL) was added and the mixture was washed three times with 40 mL portions of cold 10% aqueous citric acid followed by three washes with 40 mL portions of water. The organic-phase was dried over anhydrous sodium sulfate and evaporated to a foam to give 1.86 g (84%) of the title compound.

EXAMPLE 50

2'-O-Hexylaminoibuprofenyl-3'-O-succinate-5'-O-DMT-$N^6$-benzoyladenosine LCAA-CPG 35

Compound 34 (1.80 g, 1.70 mmol) and 4-dimethylaminopyridine (0.21 g, 1.70 mmol) were dissolved in anhydrous acetonitrile (10.0 mL) at room temperature. In another flask, 2,2'-dithiobis(5-nitropyridine) (0.53 g, 1.70 mmol) was dissolved in anhydrous acetonitrile (7.0 mL) and anhydrous dichloromethane (6.0 mL). This solution was then added to the first flask. In a third flask, triphenylphosphine (0.45 g, 1.70 mmol) was dissolved in acetonitrile (8.0 mL) and then combined with the first flask. Finally, acid-washed LCAA-CPG (7.38 g, 0.85 mmol) was added and the mixture was shaken for 2 hours. The resulting resin was washed three times with dichloromethane and ether. Then it was combined with Cap A (30 mL) and Cap B (30 mL) solutions from PerSeptive Biosystems GmbH and shaken for an additional hour. The resin was then washed again three times with dichloromethane and ether and placed under vacuum overnight to dry. The final loading was determined to be 50 umol/g.

EXAMPLE 51

Procedeure for SEQ ID NO's. 6 and 7

The following modified amidites were used in the above sequences: 2'-O-methoxyethyl-thymidine (RIC, Inc., lot #E1050-P-10), 2'-O-methoxyethyl-5-methylcytidine (lot #S1941/RS), 2'-O-methoxyethyl-adenosine (lot #EMA-P-14 RIC), and 2'-O-methoxyethyl-guanosine (lot #EMG-P-18U RIC). Compound 35 (which is attached to CPG) was used as the LCAA-CPG solid support for the synthesis of Isis #111494-1 and 111496-1. MDC-1395-94 (compound 31) was used as the LCAA-CPG solid support for the synthesis of Isis #111495-1 and 111497-1.

The required amounts of the amidites (1 M solutions of unmodified nucleosides and 100 mg/mL of modified nucleosides) were placed in dried vials, dissolved in acetonitrile, and connected to the appropriate ports on a Millipore Expedite™ Nucleic Acid Synthesis System (ISIS 4). 60 mg of solid support resin was used in each column for 2×1 umole scale synthesis. The synthesis was run using the IBP-PS(1 umole) double coupling protocol for phosphorothioate backbones. The trityl reports indicated normal coupling results.

After synthesis, the oligonucleotides were deprotected with conc. ammonium hydroxide(aq) at 55° C. for approximately 16 hrs. Then they were evaporated, using a Savant AS160 Automatic SpeedVac, (to remove ammonia) and filtered to remove the CPG-resin.

The crude samples were analyzed by MS, HPLC, and CE. Then they were purified on a Waters 600E HPLC system with a 991 detector using a Waters C18 Prep. scale column (C18 Prep.) and the following solvents: A: 0.1 M aqueous ammonium acetate and B: acetonitrile utilizing the "C18PREP" method.

After purification the oligos were evaporated to dryness and then detritylated with 80% acetic acid at room temperature for approximately 30 minutes and again evaporated. The oligonucleotides were desalted by dissolving them in water with concentrated ammonium hydroxide and running them through a C18 Prep. column using water as the solvent. The oligonucleotides were then washed from the column with acetonitrile. The resulting purified oligonucleotides were evaporated and analyzed by MS, CE and HPLC.

TABLE XIV

| SEQ ID NO. | ISIS # | Backbone | Sequence[1] |
|---|---|---|---|
| 6 | 111494 | P=S | GTT $C^{5Me}$ $TC^{5Me}$ $GC^{5Me}T$ GGT GAG TTT $C^{5Me}$ $A^{IBU}$ |
| 6 | 111495 | P=S | GTT $C^{5Me}$ $TC^{5Me}$ $GC^{5Me}T$ GGT GAG TTT $C^{5Me}$ $A^{PAL}$ |
| 7 | 111496 | P=S | $AGC^{5Me}$ $TTC^{5Me}$ TTT $GC^{5Me}A$ $C^{5Me}AT$ GTA $AA^{IBU}$ |

TABLE XIV-continued

| SEQ ID NO. | ISIS # | Backbone | Sequence[1] |
|---|---|---|---|
| 7 | 111497 | P=S | AGC$^{5Me}$ TTC$^{5Me}$ TTT GC$^{5Me}$A C$^{5Me}$AT GTA AA$^{PAL}$ |

[1]All underlined nucleosides contain the 2'-O-Methoxyethyl group. A$^{IBU}$ = 2'-O-Ibuprofenyl-aminohexyl-adenosine [ibuprofenyl = (4-isobutylphenyl) isopropionyl]. A$^{PAL}$ = 2'-O-Palmityl-aminohexyl-Adenosine.

TABLE XV

| ISIS # | Expected Mass (g/mol) | Observed Mass (g/mol) | HPLC Retention Time (min) | CE Retention Time (min) | Crude Yield (ODs) | Final Yield (ODs) |
|---|---|---|---|---|---|---|
| 111494-1 | 6795.00 | 6795.43 | 40.87 | 6.27 | 532 | 136 |
| 111495-1 | 6845.11 | 6844.08 | 61.80 | 5.87 | 568 | 163 |
| 111496-1 | 7422.73 | 7422.98 | 43.79 | 7.54 | 538 | 282 |
| 111497-1 | 7472.84 | 7472.92 | 62.73 | 7.27 | 666 | 130 |

EXAMPLE 52

Cholesterol Conjugated Full 2'-O-Methoxyethyl (MOE) Phosphodiester Oligonucleotide SEQ ID NO: 4 (ISIS #16952 Unconjugated, ISIS #16296 Conjugated) TCT GAG TAG CAG AGG AGC TC To determine the effect of conjugating a cholesterol group at the 3'-position of a uniform 2'-MOE-phosphodiester 20 mer antisense oligonucleotide both the conjugated as well as the non-conjugated oligonucleotides were prepared. All of the cytosine bases were 5-methylcytosines and all ribosyl sugars were 2'-O-MOE with the exception of the 3'-terminal nucleoside having the cholesterol attached which was a 2'-hydroxycytidine. Attachment of the cholesterol group was via a 6-aminohexyloxy linker at the 3' position of the conjugated oligonucleotide. The cholesterol molecule is attached to the amino group of the linker via a carbamate linkage.

Figure 2:
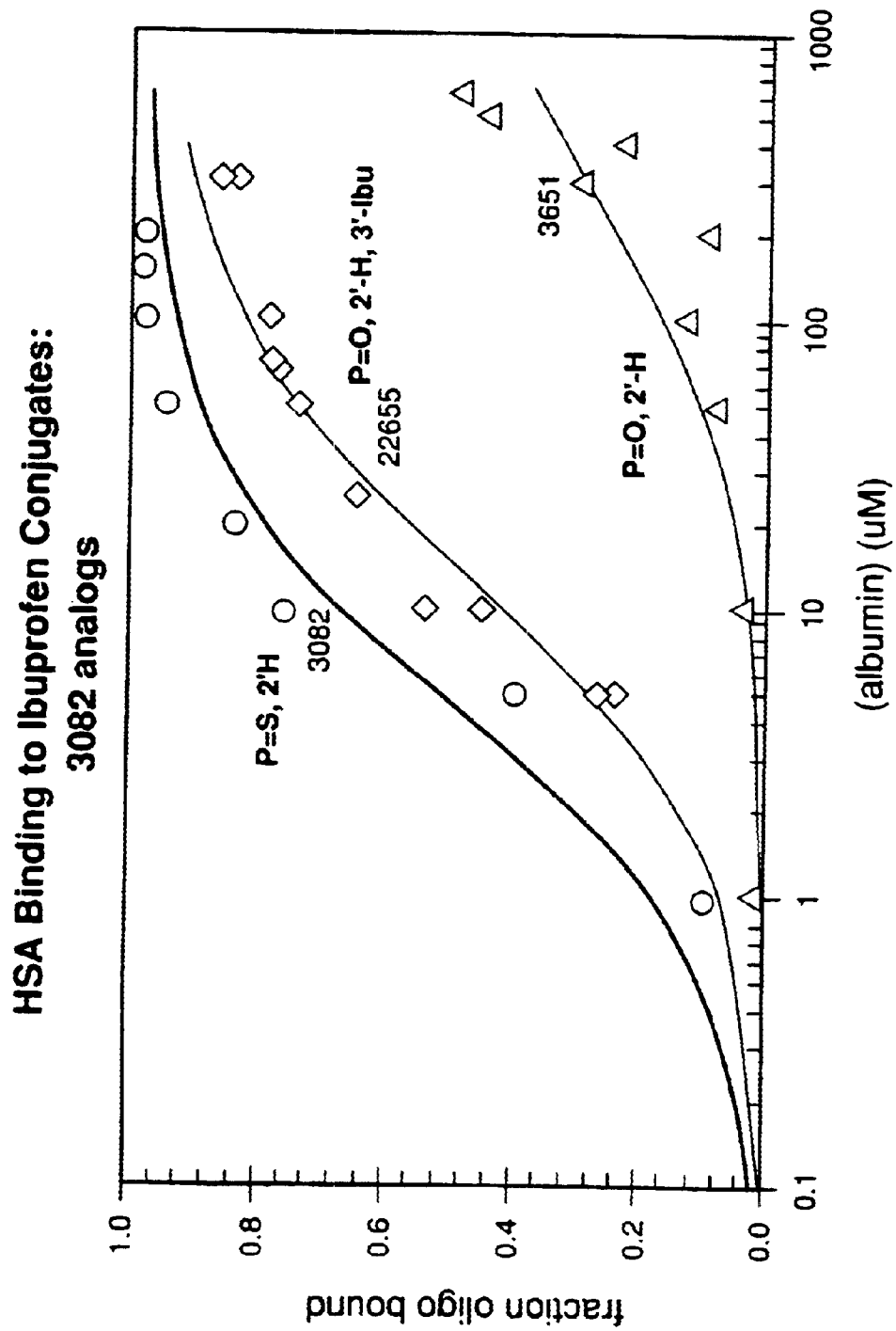
FIG. 2 is a graph showing a comparison of the capacity of HSA (Sigma A3782 lot 97H7604) for an ibuprofen conjugate (diamonds) compared to that of an unconjugated phosphorothioate DNA (triangles). Capacity was measured at 50 mM HSA with increasing concentrations of oligonucleotide.

The plasma concentration of the cholesterol conjugated oligonucleotide ($^3$H, ISIS-16296) was compared to the parent oligonucleotide ($^3$H, ISIS-16952, FIG. 2). The study was performed in male Sprague-Dawley rats using I.V. bolus administration of $^3$H radiolabeled oligonucleotides. The plasma concentration was maintained at a higher level and was reduced at a slower rate for the conjugated oligonucleotide.

The tissue distribution of the two radio labeled oligonucleotides was examined in Sprague-Dawley rats following I.V. bolus administration (FIG. 3). Almost all of the parent oligonucleotide was seen in the kidney cortex after 24 hours and only baseline amounts of oligonucleotide was seen in the other major organs tested (plasma, liver, spleen, small intestine, large intestine and mesent LN. The distribution profile for the conjugated oligonucleotide showed distribution to all the organs in much higher concentrations that the parent oligonucleotide.

The percent of the dose excreted through the urine was calculated for 0–6 and 6–24 hours for the parent and conjugated oligonucleotides (FIG. 4). About 38% of the parent oligonucleotide or metabolites thereof was excreted within the first 6 hours of administration. Only about 5% of the conjugated oligonucleotide was excreted during the same time periods.

In a similar study, SEQ ID NO: 5 (ISIS-3082) was prepared along with 5 z for a variety of comparative pharmacokinetic studies including protein binding. The parent compound a 20 mer phosphorothioate was compared with the phosphorothioate and phosphodiester 2'-propoxy analogs, a chimeric analog having 2'-propoxy diester wings and a phosphorothioate deoxy center, and 5I-octadecylamine and 5'-(2'-O-hexylamino-carbonyl-oxy-cholesterol) phosphorothioate analogs. This study, in part, reported decreased excretion of the cholesterol modified oligonucleotide relative to the parent phosphorothioate oligonucleotide (Crooke et al., *The Journal of Pharmacology and Experimental Therapeutics*, 1996, 277:923–937).

EXAMPLE 53

Effect of Conjugation on 2'-Methoxyethoxy-substituted Phosphodiester (PO/MOE) Oligonucleotides It was observed that a PO/MOE-cholesterol conjugated oligonucleotide (16296) exhibited improved binding compared to the PO/MOE analog (16952), but is still a weak binder compared to the 2'-methoxyethoxy-substituted phosphorothioate (PS/MOE) oligonucleotide (11159). The PO/MOE-ibuprofen conjugate (27700), however, not only exhibited improved binding compared to the unconjugated PO/MOE analog (16952), but also showed tighter binding that the PS analog (3067) or the PS/MOE analog (11159). These results are shown below in Table XVI.

TABLE XVI

| Oligo. | Sequence | Description | K$_d$ ($\mu$M) |
|---|---|---|---|
| 3067 | TCTGAGTAGCAGAGGAGCTC | Full PS | 41.2 ± 7.3 |
| 11159 | TCTGAGTAGCAGAGGAGCTC | Full PS, MOE | 29.3 |
| 16952 | TCTGAGTAGCAGAGGAGCTC | Full PO, MOE | 672 ± 7.21 |
| 16296 | TCTGAGTAGCAGAGGAGCTC | Full PO, MOE, cholesterol conjugate | 225 |
| 27700 | TCTGAGTAGCAGAGGAGCTC | Full PO, MOE, ibuprofen conjugate | 10.0 ± 1.30 |

EXAMPLE 54

Conjugation of Human α$_1$-Acid Glycoprotien (AAG) Binding Drugs to Oligonucleotides The following drug moieties were identified as drugs that bind to AAG: acenocoumarol, chlorpromazine, dipyridamole, imipramine, methadone, perphenazine, phenylbutazone, pindolol, progesterone, propanolol, RU 42633, RU 38486, thioridazine, ticlopidine, trifluoperazine, warfarin and phenathiazines.

Among the various phenothiazine ligands, 2-chloro-10-(2-carboxyethyl)-phenothiazine was selected as a conjugated ligand for illustrative purposes. 2-chloro-10-(2-carboxyethyl)-phenothiazine (Melikian et al., *J. Pharm. Sci,*. 1977, 66:228, 1977) is converted to pentafluorophenyl ester using pentafluorophenol and DCC. This compound is then condensed with 3'-O-(6-aminohexyl)-5'-O-DMT uridine and further converted to its controlled pore glass derivative. Oligonucleotides are synthesized from the controlled pore glass as described for other examples.

EXAMPLE 55

Improved Cellular Uptake by Conjugation of Cell Surface Integrins With Oligonucleotide Fibrinogen-derived peptides (RGD and RGD like) are prepared for conjugation via standard peptide synthesis procedures.

| Peptide I | RIARGDFPDDRK (SEQ ID NO: 8) (an RGD peptide) |
| Peptide II | DELAEGGGVRGPRV (SEQ ID NO: 9) |

These peptides were synthesized in the solid phase synthesizers. At the amino terminal end, 6-hexene-carboxylic acid is coupled. After deprotection of the peptide, the olefinic linkage is converted into an aldehyde using $OsO_4$/N-methyl-morpholine oxide followed by $NaIO_4$ oxidation. The aldehyde containing peptide is conjugated to —O—$NH_2$ linked oligonucleotides. Surface plasmon resonance experiments indicated that these peptide conjugated oligonucleotides bind to cell surface integrins.

EXAMPLE 56

Proteins and Substrates to Which These Proteins Bind

| Proteins | Substrate |
| --- | --- |
| Vitamin-D binding protein | Vitamin D |
| Cortisol-binding globulin | Cortisol |
| Sex-hormone-binding protein | Sex hormones |
| Thyroxine-binding globulin and Prealbumin | Thyroxine |

EXAMPLE 57

General Procedure for Preparing Succinimide Esters of Small Drugs

To a solution of 1 mmol acid and 1 mmol N-hydroxysuccinimide in 4 mL of dry THF 1 mmol of dicyclohexylcarbodiimide (DCC) was added. The reaction mixture was stirred for two days at room temperature. The precipitate was filtered off and the filtrate was concentrated under reduced pressure. The residue was dissolved in 3 mL of $CH_2Cl_2$, and the product purified by thick layer chromatography: Chromatotron, 2 mm plate, using a gradient from 0 to 5% of MeOH in $CH_2Cl_2$. Appropriate fractions were collected, solvent removed under reduced pressure, and the product was dried under reduced pressure overnight.

| Drug | MW acid | $R_f$ (5% MeOH in $CH_2Cl_2$) acid | ester | Yield (%) | MW of ester |
| --- | --- | --- | --- | --- | --- |
| Indomethacin | 357.8 | 0.35 | 0.8 | 95 | 454.8 $C_{23}H_{19}ClN_2O_6$ |
| Mycophenolic acid | 320.3 | 0.25 | 0.9 | 72 | 417 $C_{21}H_{23}NO_8$ |
| Acetyl Salicylic acid | 180.2 | 0.1 | 0.6 | 30 | 277 $C_{13}H_{11}NO_6$ |

NHS ester of indomethacin: $^1$H NMR (400 MHz, CDCl) δ 7.68 (2H, d, J=12.0 Hz), 7.48 (2H, d, J=12.0 Hz), 6.98 (1H, d, J=3.6 Hz), 6.93 (1H, d, J=13.5 Hz), 6.68 (1H, dd, J=13.5, 3.6 Hz), 3.98 (2H, s), 3.87 (3H, s), 2.84 (4H, s), 2.39 (3H, s).

NHS ester of mycophenolic acid: $^1$H NMR (400 MHz, $CDCl_3$) δ 7.68 (1H, s), 5.34 (1H, t, J=10.2 Hz), 5.21 (2H, s), 3.42 (2H, d, J=10.2 Hz), 2.83 (4H, s), 2.71 (2H, t, J=12.0 Hz), 2.43 (2H, t, J=12.0 Hz), 2.16 (3H, s), 1.84 (3H, s).

NHS ester of acetyl salicylic acid: ES-MS: 300 [M+Na]$^+$. $^1$H NMR (400 MHz, $CDCl_3$) δ 8.11 (1H, dd, J=11.8, 2.4 Hz), 7.66 (1H, ddd), 7.36 (1H, dd), 7.18 (1H, d, J=12.3 Hz), 2.83 (4H, s), 2.30 (3H, s). 13C NMR (100 MHz, $CDCl_3$) δ 169.0, 159.5, 151.2, 135.8, 132.1, 126.2, 124.2, 118.8, 25.4, 20.7.

The thiocresol ester of acetyl salicylic acid was prepared by stirring 180 mg (1 mmol) of acetyl salicylic acid, 124 mg (1 mmol) of pthiocresol and 206 mg (1 mmol) of DCC in 4 mL of anhydrous THF at room temperature for 2 days. The precipitate was filtered off, the filtrate was concentrated under reduced pressure, the residue dissolved in 3 mL of $CH_2Cl_2$ and purified by preparative thick layer chromatography (Chromatotron, 2 mm plate, using a gradient from 0 to 10% MeOH in $CH_2Cl_2$). Obtained 256 mg (90% yield) of white solid. $R_f$ 0.95 in 5% MeOH in $CH_2Cl_2$. $C_{16}H_{14}O_3S$. Calc: 286. $^1$H NMR (400 MHz, $CDCl_3$) δ 8.06 (1H, dd, J=11.7, 2.2 Hz), 7.59 (1H, ddd), 7.41–7.25 (5H, m), 7.16 (1H, d, J=12.0 Hz), 2.41 (3H, s), 2.32 (3H, s).

The pentachlorophenol ester of acetyl salicylic acid was prepare by stirring 180 mg (1 mmol) of acetyl salicylic acid, 266 mg (1 mmol) pentachlorophenol and 206 mg (1 mmol) DCC in 4 mL of anhydrous THF at room temperature for 2 days. The precipitate was filtered off, the filtrate was concentrated under reduced pressure, the residue dissolved in 3 mL of $CH_2Cl_2$ and purified by preparative thick layer chromatography (Chromatotron, 2 mm plate, using a gradient from 0 to 10% MeOH in $CH_2Cl_2$). Obtained 260 mg (61% yield) of a pale yellow solid. $R_f$ 0.9 in 5% MeOH in $CH_2Cl_2$. $C_{15}H_7O_4Cl_5$. Calc. 426. $^1$H NMR (400 MHz, $CDCl_3$) δ 8.31 (1H, dd, J=11.9, 2.5 Hz), 7.72 (1H, ddd), 7.44 (1H, ddd), 7.23 (1H, d, J=12.0 Hz), 2.31 (3H, s).

EXAMPLE 58

General Procedure for Preparing Conjugated Active Esters of Small Molecules to 3'-(2'-Aminopropyl)-TCT GAG TAG CAG AGG AGC TC (SEQ ID NO: 4 ISIS-16952)

Solution conjugation chemistry via activated esters

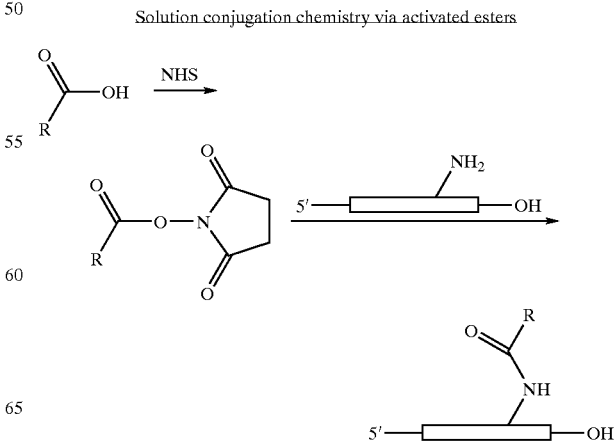

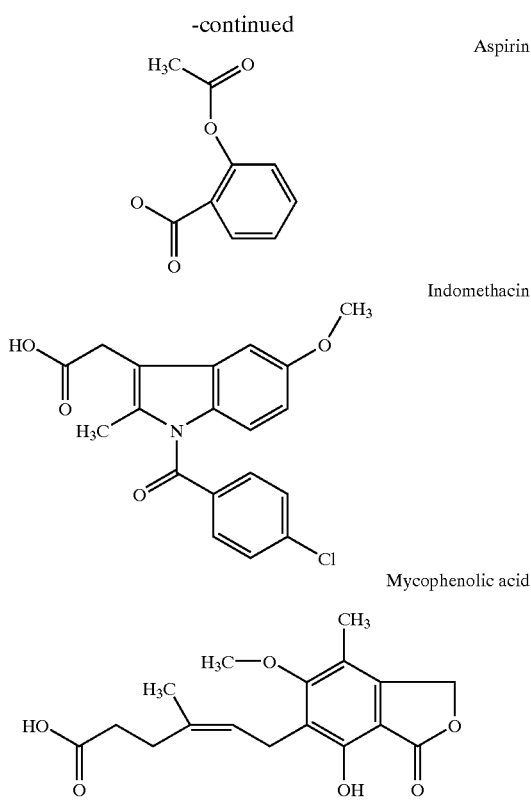

Preparation on an analytical scale used a reaction volume of 500 mL, pH 9 (0.1 M NaHCO$_3$/Na$_2$CO$_3$) with the following: 10 ODs in 20 mL of H$_2$O of SEQ ID NO: 4-3'-NH$_2$ in triethylammonium form (TEA); 100 mL of 0.5 M buffer and 255 mL DMSO. To this solution, 125 mL of 0.05 M solution of activated ester in DMSO was added. The mixture was vortexed and the resultant heterogeneous mixture was kept at room temperature. The aliquots were analyzed by RP-C$_{18}$ HPLC after 2, 4, 6 and 18 h. It was shown that the reaction was completed at 6 hours. The conjugates had higher retention times then the oligonucleotide.

| Modification | Retention time (min) | ES-MS Calculated | Found | Yield % (HPLC) | ISIS # |
|---|---|---|---|---|---|
| SEQ ID NO: 4-3'-NH$_2$ | 16 | | | | |
| SEQ ID NO: 4-indomethacin | 22 | 8046.8 | 8048.17 | 85 | 124546 |
| SEQ ID NO: 4-mycophenolic acid | 18.5 | 8009 | 8009.5 | 80 | 124545 |
| SEQ ID NO: 4-acetylsalicylic acid | 17.5 | 7869 | 7866 | 60 | 30785 |
| SEQ ID NO: 4-salicylic accid | 18 | 7826 | 7824.8 | | 126785 |
| SEQ ID NO: 4-NH-Ac | 16.5 | | | | |

HPLC conditions: RP-C$_{18}$ Delta Pak column, 3.9 mm×300 mm, 15 m, 1.5 mL/min. A: 0.1 M NH$_4$OAc; B: 80% MeCN Gradient from 0 to 60% B in 30 min.

EXAMPLE 59

Conjugation of Acetylsalicylic Acid

Various activated esters of acetylsalicylic acid were used to conjugate aspirin. A better yield was obtained using pentachlorophenol ester which gave the aspirin conjugate in 60% yield. For some activated esters, that were examined in this reaction sequence, only acetylation of the amino group of the oligonucleotide was observed.

| Activated ester | Yield of SEQ ID NO: 4-NH-Ac | Yield of SEQ ID NO: 4-aspirin |
|---|---|---|
| NHS | 100% | |
| p-Thiocresol | 100% | |
| Pentachlorophenol | 40% | 60% |

EXAMPLE 60

Stability of SEQ ID NO: 4-Acetylsalicylic Acid Conjugate

The stability of SEQ ID NO: 4-aspirin conjugate was examined in various solution. The stability of the conjugate in various conditions was estimated by the analysis of conjugate solutions by RP-C$_{18}$ HPLC at different incubation times.

| Buffer | pH | T$_{1/2}$ |
|---|---|---|
| Water | 8.2 | 10 days |
| 0.05M Triethylammonium acetate | 7.0 | 4 days |
| 1M NH$_4$OAc | 6.8 | 6 h |
| 0.1M NH$_4$OAc | 6.0 | 4 days |
| 0.1M NH$_4$OAc | 6.5 | 48 h |
| 0.1M NH$_4$OAc | 7.0 | 24 h |
| 0.1M NH$_4$OAc | 7.5 | 12 h |

EXAMPLE 61

Preparative Scale Synthesis of Conjugates

In Preparative scale, a heterogeneous solution of 100 ODs of SEQ ID NO: 4-3'-NH$_2$ in TEA form, 100 mL 0.5 M buffer and 400 mL 0.1 M solution of activated ester in DMSO were mixed and vortexed for 6 h at room temperature. Excess activated ester was removed by gel filtration through Sephadex G-25. The conjugate was purified and desalted by RP-C$_{18}$ HPLC. Yield: from 30 to 50 ODs of the conjugate.

EXAMPLE 62

ISIS SEQ ID NO: 4-Salicylic Acid Conjugate

The title conjugate was obtained by hydrolysis of SEQ ID NO: 4-aspirin conjugate in 0.1 M NH$_4$OAc, pH 7.5, 18 h.

EXAMPLE 63

Warfarin Conjugation

I. Synthesis of C6 aminooxy linker and its phosphoramidite was by the following scheme:

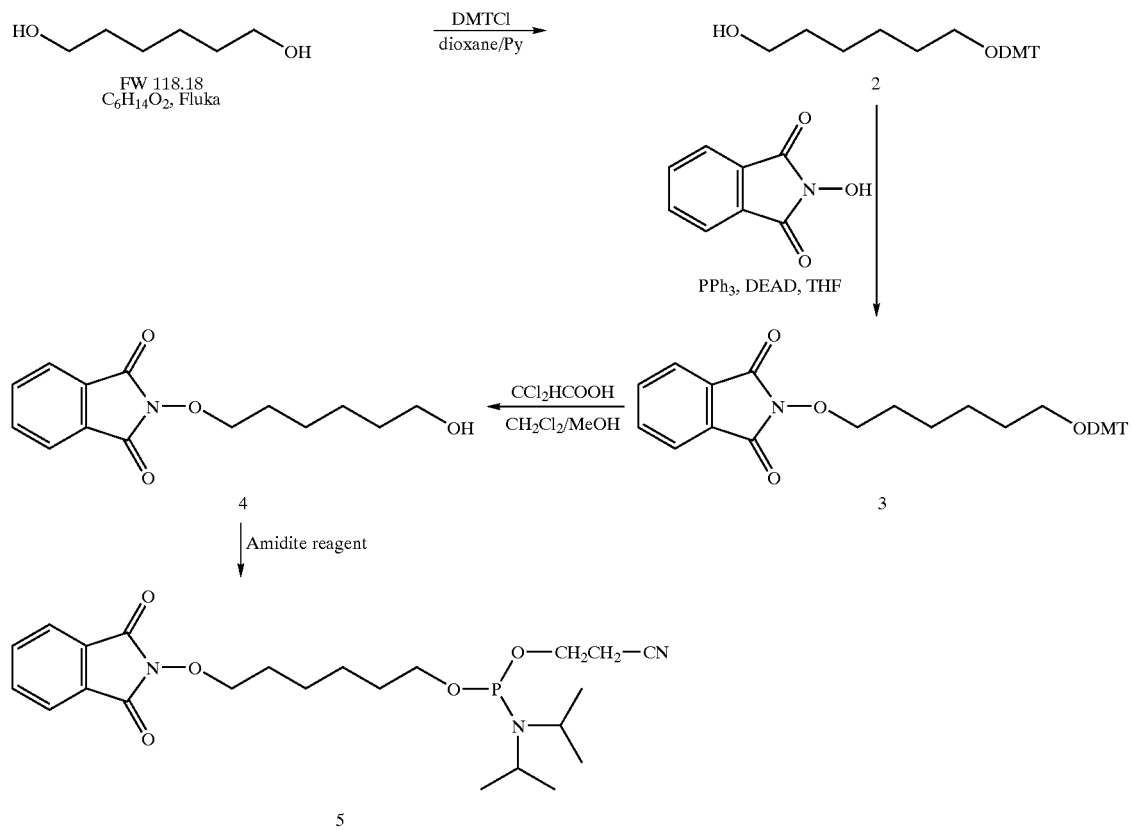

Compound 2

1,6-Hexanediol, 8.5 g (72 mmol) was dried first by coevaporation with anhydrous pyridine (2×50 mL), then overnight under high vacuum. The residue was dissolved in a mixture of 60 mL dry 1,4-dioxane and 10 mL of dry Py and 8.0 g (23.6 mmol) DMT-Cl was added in 4 portions. The reaction mixture was stirred under Ar at RT for 2 days. The solution was concentrated under reduced pressure, the residue was dissolved in 300 mL of $CH_2Cl_2$, washed with 5% aq $NaHCO_3$, then brine. The organic phase was concentrated under reduced pressure. A yellow oil (9 g, 21.4 mmol) was obtained after purification by column chromatography using a gradient of MeOH, from 0 to 10%, in 0.2% $Py/CH_2Cl_2$. $^1H$ NMR (400 MHz, $CDCl_3$) δ 7.46–7.43 (2H, m), 7.35–7.26 (5H, m), 7.20–7.17 (2H, m), 6.85–6.80 (4H, m), 3.80 (3H, s), 3.79 (3H, m), 3.65 (2H, t, J=7.2 Hz), 3.1–3.0 (2H, m), 1.63–1.55 (4H, m), 1.42–1.34 (4H, m). $^{13}C$ NMR (100 MHz, $CDCl_3$) δ 158.8, 158.5, 145.6, 139.7, 136.9, 130.2, 129.4, 128.1, 128.0, 127.9, 113.4, 113.2, 85.8, 63.6, 63.2, 55.4, 32.9, 30.3, 26.3, 25.8.

Compound 3

Monosubstituted hexanediol (Compound 2), (1.68 g, 4 mmol), (0.7 g, 4.3 mmol) of N-hydroxyphthalimide and (1.4 g, 4.2 mmol) of $PPh_3$ was dissolved in anhydrous dioxane. To this solution 0.7 mL (3.6 mmol) of diethylazodicarboxylate (DEAD) was added dropwise, and the reaction mixture stirred overnight at room temperature. TLC in 5% MeOH/$CH_2Cl_2$, 1% $Et_3N$ indicated the completion of reaction (a new spot with $R_f$ 0.9, compared to $R_f$ 0.6 of Compound 2). Reaction mixture was concentrated under reduced pressure. The residue was dissolved in hexane/ethylacetate, 4/1, by an addition of $CH_2Cl_2$. The product was purified by preparative column chromatography, eluted with 1% $Et_3N$, hexane/ethylacetate, 3/2, to give after drying under reduced pressure 2 g (89%) of colorless glass. $^1H$ NMR (400 MHz, $CDCl_3$) δ 7.83–7.81 (2H, m), 7.74–7.72 (2H, m), 7.42 (2H, d, J=8.4 Hz), 7.35–7.25 (6H, m), 7.20–7.18 (1H, m), 6.81 (4H, d, J=8.8 Hz), 4.17 (2H, t, J=6.4 Hz), 3.77 (6H, s), 3.04 (2H, t, J=6.4 Hz), 1.79–1.75 (2H, m), 1.64–1.57 (2H, m), 1.44–1.42 (4H, m). $^{13}C$ NMR (100 MHz, $CDCl_3$) δ 164.0, 158.2, 145.6, 136.8, 134.4, 130.2, 129.7, 128.5, 128.0, 126.7, 123.6, 113.2, 85.8, 78.3, 63.4, 55.6, 30.6, 28.2, 26.1, 25.8.

Compound 4

Compound 3, 1.1 g (1.95 mmol) was dissolved in 20 mL of $CH_2Cl_2$/MeOH, 9:1, the dichloroacetic acid was added until stable red color appeared and then kept for at room temperature for an additional 45 min. The reaction mixture was quenched with 50 mL of 5% aq. $NaHCO_3$ and diluted with 50 mL $CH_2Cl_2$. The organic phase was washed with 50 mL of brine and concentrated under reduced pressure. The product was purified by preparative thick layer chromatography (Chromatotron, plate 2 mm). Appropriate fractions were collected and dried under reduced pressure to give 0.36 g (70%) of white solid. $R_f$ 0.6 in 5% MeOH/$CH_2Cl_2$, 1% $Et_3N$. MS (positive MeOH): 264.2 $[M+H]^+$. $^1H$ NMR (400 MHz, $CDCl_3$) δ 7.84–7.82 (2H, m), 7.75–7.73 (2H, m), 4.21 (2H, t, J=6.6 Hz), 3.69–3.66 (2H, m), 1.81–1.79 (2H, m), 1.63–1.53 (4H, m), 1.47–1.44 (2H, m). $^{13}C$ NMR (100 MHz, $CDCl_3$) δ 163.9, 134.6, 129.2, 123.7, 78.5, 62.9, 32.7, 28.3, 25.5.

Compound 5

To a solution of Compound 4, 300 mg (1.14 mmol) in 4 mL of anhydrous MeCN under Ar, 543 mL (1.75 mmol, 1.5 eq) of phosphoramidite reagent (2-cyanoethyl tetraisopropyl-phosphorodiamidite) and 2.28 mL (1.03 mmol, 0.9 eq.) of 0.45 M solution of tetrazole in MeCN were added. A precipitate appeared in a few seconds. After 1 h, 300 mL of Et$_3$N was added to the reaction mixture followed by quenching with 30 mL of 5% aq. NaHCO$_3$. The product was rapidly extracted with 50 mL CH$_2$Cl$_2$, the organic phase was washed with 30 mL brine, then 30 mL of water, concentrated under reduced pressure. The product was purified by preparative thick layer chromatography (Chromatotron, plate 2 mm) in the gradient from 5 to 50% ethyl acetate in hexane with 1% Et$_3$N. Appropriate fractions were collected and dried under reduced pressure to give 188 mg (35%) of colorless oil. R$_f$ 0.4 in hexane/ethylacetate/Et$_3$N, 70/30/5. $^{31}$P NMR (162 MHz) δ 148.2, 148.0.

EXAMPLE 64

Synthesis of Warfarin Phosphoramidite

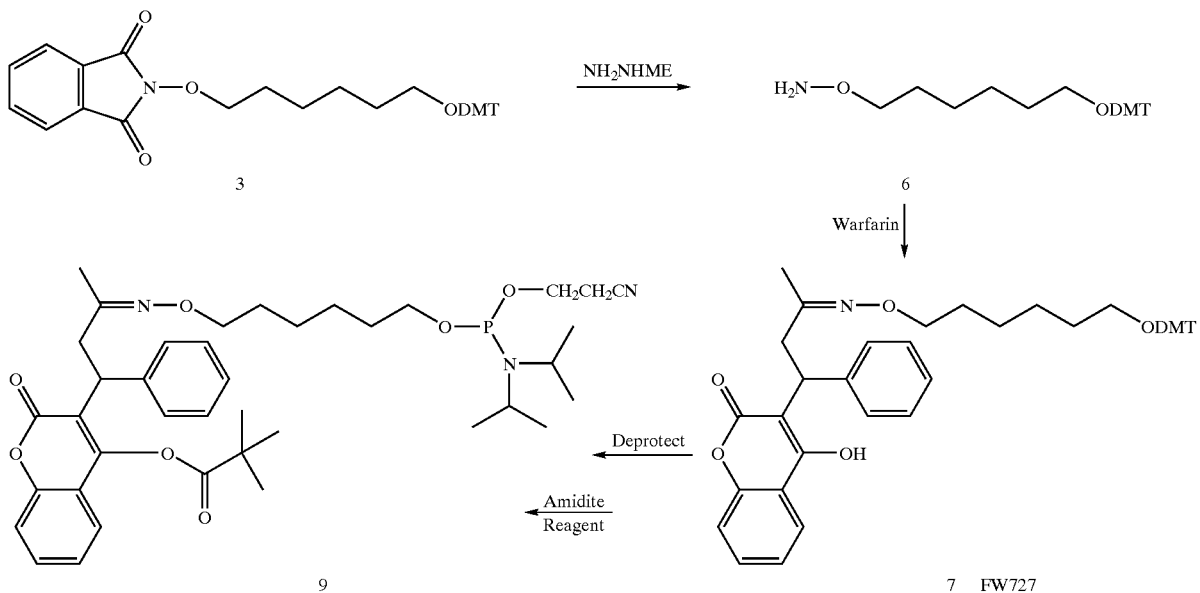

Compound 7

To 1 mmol of Compound 3 in 6 mL of anhydrous CH$_2$Cl$_2$ at −10° C. was added 1.1 eq. of methylhydrazine which formed a white precipitate. After 1 h an additional 5 mL of cold CH$_2$Cl$_2$ was added, and the reaction mixture was rapidly filtered. The precipitate was washed with 5 mL of cold CH$_2$Cl$_2$. Warfarin (308 mg, 1 mmol) was added to the filtrate and the solution was allowed to stand at room temperature for 1 h. TLC showed a new fluorescent spot with R$_f$ 0.8 in 2% MeOH, 0.1% Et$_3$N in CH$_2$Cl$_2$. The reaction mixture was concentrated under reduced pressure and the crude material was purified by preparative thick layer chromatography (Chromatotron, plate 2 mm) using a gradient from 0 to 10% MeOH in CH$_2$Cl$_2$, 1% Et$_3$N. Obtained 0.36 g (50%) of colorless oil. $^1$H NMR (400 MHz, CDCl$_3$) δ 7.89 (2H, d, J=8.4 Hz), 7.48–7.41 (4H, m), 7.32–7.24 (6H, m), 7.20–7.06 (6H, m), 6.81 (4H, d, J=8.8 Hz), 4.87–4.84 (1H, m), 3.92 (2H, t, J=7.2 Hz), 3.78 (6H, s), 3.28–3.24 (1H, m), 3.14–3.09 (1H, m), 2.99 (2H, t, J=6.4 Hz), 1.85 (3H, s), 1.58–1.46 (4H, m), 1.27–1.19 (4H, m).

Compound 8

Pivaloyl chloride, 84 mL (0.7 mmol), was added to a solution of Compound 7, 400 mg (0.55 mmol) and 20 mg DMAP in 10 mL of anhydrous pyridine. A precipitate appeared immediately after addition, and the heterogeneous reaction mixture was stirred for 2 h at room temperature. The TLC in 0.5% MeOH, 0.1% Et$_3$N in CH$_2$Cl$_2$ showed complete conversion of starting material to more hydrophobic one with R$_f$ 0.45. The reaction was quenched with 50 mL of 5% aq. NaHCO$_3$ and the product was extracted with 2×50 ml of CH$_2$Cl$_2$. The organic phase was washed with 50 mL brine, then concentrated under reduced pressure and dried to give 440 mg of an oil. The oil was detritylated without further purification.

Detritylation

The oil, 440 mg, was dissolved in 20 mL CH$_2$Cl$_2$/MeOH, 9/1, and dichloroacetic acid was added until the color of the solution stabilized. TLC: a new more polar spot appeared with R$_f$ 0.4 in 5% MeOH/CH$_2$Cl$_2$. After addition of 100 mL of 5% aq. NaHCO$_3$, the product was extracted with 50 mL of CH$_2$Cl$_2$. Organic phase was washed with 40 mL of brine and concentrated under reduced pressure. The product was obtained after purification by preparative thick layer chromatography (Chromatotron, plate 2 mm) using a gradient from 0 to 5% MeOH in CH$_2$Cl$_2$. Yield 200 mg (71%) of an oil. NMR spectrum shows 2 signal's sets in ratio 80/20. MS (positive MeOH): 508 [M+H]$^+$. $^1$H NMR (400 MHz, CDCl$_3$) δ 7.49–7.40 (4H, m), 7.32–7.19 (5H, m), 4.58 (1H, t, J=7.6 Hz), 3.91 (2H, t, J=6.8 Hz), 3.58 (2H, t, J=6.8 Hz), 3.20 (2H, bs), 1.82 (3H, s), 1.54 (9H, s), 1.48–1.43 (4H, m), 1.23–1.21 (2H, m). $^{13}$C NMR (100 MHz, CDCl$_3$) δ 175.1, 160.9, 154.8, 152.7, 140.5, 132.0, 128.4, 126.9, 124.5, 122.9, 122.1, 116.95, 116.4, 73.5, 63.0, 39.9, 38.9, 37.3, 32.9, 29.2, 27.6, 25.9, 25.8, 25.7, 15.2.

Compound 9

Compound 8, 0.18 g (0.36 mmol), was dissolved in 5 mL of anhydrous MeCN. To this solution 169 mL (0.53 mmol, 1.5 eq.) of phosphoramidite reagent and 0.71 mL (0.32 mmol, 0.9 eq.) of 0.45 M 1H-tetrazole solution in MeCN were added. The reaction mixture was stirred under Ar for 3 h at room temperature. TLC in hexane/ethylacetate/Et$_3$N, 70/30/5, revealed a new spot with R$_f$ 0.6, as well as fluorescent spot with R$_f$ 0.5 which resulted from a loss of pivaloyl protecting group. 200 mL of Et$_3$N followed by 30 mL of 5% aq. NaHCO$_3$ solution was added to the reaction mixture. The product was rapidly extracted with 50 mL CH$_2$Cl$_2$, organic phase was washed with 30 mL of brine, 20 mL of water and concentrated under reduced pressure. After purification by preparative thick layer chromatography (Chromatotron, plate 2 mm) using a gradient from 0 to 10% MeOH in CH$_2$Cl$_2$, 1% Et$_3$N, 186 mg (0.26 mmol, 72%) of a colorless oil was obtained. $^{31}$P NMR (161 MHz, MeCN) δ 148.2, 148.0. The purity was greater than 98%.

EXAMPLE 65

Warfarin Containing Controlled-pore Glass CPG 10

Tritylation

2'-O-(ethyloxyphthalimido)5-methyluridine, 223 mg (0.5 mmol), was dried by coevaporation with 50 mL of anhydrous MeCN, then overnight under reduced pressure. The dried compound was dissolved in 5 mL of anhydrous pyridine and 203 mg (0.6 mmol) of DMTCl was added. After 1 h at room temperature, TLC showed the reaction was incomplete. Additional DMTCl, 40 mg (0.1 mmol), was added. After 30 min 50 mL of 5% aq. NaHCO$_3$ was added and the product was extracted with 2×60 mL CH$_2$Cl$_2$. The organic layer was dried under reduced pressure. The product was purified by preparative thick layer chromatography (Chromatotron, plate 2 mm) using a gradient from 0 to 10% MeOH in CH$_2$Cl$_2$, 3% Et$_3$N. The appropriate fractions were collected and dried under reduced pressure to give 100 mg (26%) of a pale yellow oil. FW 749. $^1$H NMR (400 MHz, CDCl$_3$) δ 9.65 (1H, s), 7.89–7.76 (5H, m), 7.48–7.27 (9H, m), 6.88 (4H, d, J=8.4 Hz), 6.00 (1H, bs), 4.61–4.42 (3H, m), 4.36–4.05 (4H, m), 3.83 (6H, s), 3.59–3.54 (2H, m), 2.80–2.78 (1H, m), 1.39 (3H, s).

Succinic Ester

To a solution of 170 mg (0.23 mmol) of the DMT-nucleoside in 1 mL anhydrous 1,2-dichloroethane, 15 mg (0.125 mmol, 0.5 eq.) of DMAP, 35 mL (0.25 mmol, 1.1 eq.) Et$_3$N, and 34 mg (0.34 mmol, 1.5 eq) succinic anhydride were added. The reaction was heated at 50° C. for 30 min under anhydrous conditions. 1,2-Dichloroethane, 15 mL, was added and the solution was washed with 2×10 mL of ice-cold 10% citric acid and 2×10 mL of water. The organic layer was concentrated and dried under high vacuum to give 149 mg of a yellow foam. This foam was dissolved in 2 mL of CH$_2$Cl$_2$, and precipitated in 50 mL of hexane/ether, 1/1. v/v. White powder was obtained: 87 mg (45%). FW 849. C$_{45}$H$_{43}$N$_3$O$_{14}$. R$_f$ 0.3 in 5% MeOH, 0.1% Et$_3$N in CH$_2$Cl$_2$. $^1$H NMR (400 MHz, CDCl$_3$) δ 9.63 (1H, s), 7.78–7.67 (5H, m), 7.39–7.22 (9H, m), 6.84–6.81 (4H, m), 5.95 (1H, d, J=3.2 Hz), 5.33 (1H, t, J=6.0 Hz), 4.48–4.38 (2H, m), 4.27 (1H, t, J=4.8 Hz), 4.18–4.10 (2H, m), 3.96–3.91 (1H, m), 3.78 (6H, s), 3.50 (1H, d, J=10.6 Hz), 3.26 (1H, dd, J=10.8, 2.0 Hz), 2.83–2.48 (4H, m), 1.37 (3H, s).

Loading

The nucleoside succinate, 87 mg (0.1 mmol), and 12.2 mg (0.1 mmol) of DMAP in 1 mL of anhydrous MeCN was added to a solution of 38 mg (0.12 mmol) of 2,2'-dithiobis(5-nitropyridine) in 1 mL of MeCN/CH$_2$Cl$_2$, 0.75/0.25, v/v. To this mixture, a solution of 26 mg (0.1 mmol) of triphenylphosphine in 0.5 mL of MeCN was added to give a red solution. After a brief agitation 0.5 g of acid-washed LCAA-CPG was added. The suspension was further agitated for 1 h. The resin was successively washed with 20 mL portions of MeCN, CH$_2$Cl$_2$ and diethyl ether followed by drying. The residual amino groups were capped by treatment with 2 mL of CapA and CapB solutions for 2 h. The resin was washed with MeCN and dried under reduced pressure. The nucleoside loading was determined by trityl test: 6.5 mg of resin in 30 mL of 3% dichloroacetic acid in CH$_2$Cl$_2$. Absorbance of DMT* was measured at 504 nm, e=76 mL×mmol$^{-1}$×cm$^{-1}$. Obtained loading 72.8 mmol/g.

CPG 11

10 mg of CPG-10 was treated with 1 mL of 0.5 M hydrazine acetate in pyridine for 1 h at room temperature, then washed successively with 1 mL of pyridine, methanol, MeCN, and dried. A solution of warfarin (1 mL, 1M) in DMF was added to resin, the mixture was shaken for 24 h at room temperature, washed with 3×1 mL of DMF, 2×1 mL MeCN and dried.

Analysis

- detritylation with 3% CF$_3$COOH/CH$_2$Cl$_2$;
- cleavage with 0.5 mL of concentrated aqueous ammonia, 1 h, room temperature;
- RP-HPLC, Delta Pak C$_{18}$, 3.9×300 mm, flow 1.5 mL/min A: 0.1 M NH$_4$OAc; B: 80% MeCN, Gradient from 0 to 60% B in 30 min.

| 2'-group | Retention time | FW for 5',3'-OH-T |
|---|---|---|
| Aminooxyethyl | 12.1 min. | 317 |
| Phthalimidooxyethyl | 20.1 min. | 447 |
| Warfarinoaminooxyethyl | 20.8 min. | 607 |
| Acetoaminooxyethyl | 16.3 min. | 357 |

After RP-HPLC analysis, warfarin adduct was obtained (80% yield) with 10% of the acetone adduct. MS (positive MeOH): 608.2 [M+H]$^+$. Reference acetone adduct was prepared by reaction of aminooxyethyl nucleoside after cleavage of phthalimide group by hydrazine acetate with acetone.

CPG 12

CPG 11, 30 mg, was treated (syringe technique) with 1 M Pivaloyl chloride, 0.05 M DMAP in pyridine for 30 min. Then the resin was washed with 5 mL of pyridine, 10 mL MeCN, dried.

EXAMPLE 66

Post-oligomerization Conjugation of Warfarin to 5'-terminus of an Oligonucleotide (T$_{12}$)

(SEQ ID NO: 10)

Phosphoramidite 5 was used for incorporation of an aminooxy linker at the 5'-position of a T$_{12}$ oligonucleotide. Coupling conditions: 0.1 M amidite solution, 1.9 mL of amidite per couple, 17 min couple time, CSO oxidation, 4 min. 3 mg of resin was treated with conc. aqueous ammonia for 1 h at room temperature. ES-MS: expected 3783.8; found 3783.75 (for phthalimide deprotected oligo).

Warfarin Coupling

Resin with aminooxy linker, 40 mg, was treated (syringe technique) with 1 mL of 0.5 M hydrazine acetate solution for 30 min. The resin was washed with 5 mL pyridine, 5 mL of MeOH, 10 mL of MeCN and dried. The resin was placed in an eppendorf tube, and 1 mL of a 0.15 M warfarin solution in MeCN/DMF, 2/1, v/v was added. The mixture was shaken for 24 h, the resin washed with 1 mL DMF, 3×1 mL MeCN and dried. Cleavage in conc. aq. ammonia 1 h at room temperature and 8 h at 55° C. gave similar RP-HPLC profiles and ES-MS spectra: Expected 4073, Found 4073. Hence the warfarin-conjugate showed stability under standard cleavage/deprotection conditions. After HPLC purification the conjugation efficiency was d>95%.

EXAMPLE 67

Incorporation of Warfarin Phosphoramidite at 5'-End of Oligonucleotide

Full diester thymidine 12 mer (T$_{12}$, P=O), 1.5 mmol scale, 0.1 M amidite solution, 380 mL of solution per couple, coupling time 14 min, CSO oxidation. After cleavage in conc. aq. ammonia, ES-MS: Expected 4073, Found 4074. HPLC: RP $C_{18}$, A: 0.1 M $NH_4OAc$; B: 80% MeCN, Gradient from 0 to 60% B in 60 min.

5'-Warfarin-3082 was prepared from the following conditions:

1 mmol scale, 14 min coupling, cleavage and deprotection conc. aq. ammonia, 8 h, 55° C. After HPLC, synthesis was not bad. ES-MS: expected 6469.7; found 6469.5. After purification 16 ODs were obtained.

EXAMPLE 68

Warfarin Conjugates
Post-oligomerization Conjugation 2 mmol synthesis of SEQ ID NO. 5 starting with CPG-10, bearing 2'-phthalimidooxyethyl-T, was performed through standard CSO protocol. The resin was treated with 1 mL of 0.5 M hydrazine acetate solution for 1 h, then washed with 5 mL Py, 5 mL MeOH, 10 mL MeCN, dried under reduced pressure for 15 min. 1 mL of 1 M solution of warfarin in DMF, was added, and mixture was shaken overnight. The solution was decanted, the resin washed 2×1 mL DMF, 3×1 mL MeCN, and dried. Cleavage and deprotection was effected using conc. aq. ammonia for 8 h at 55° C. HPLC and ES-MS showed two major products: 60% of warfarin adduct (calc. 6651 (DMT-on); found 6652), and 40% of the acetone adduct (6401). Obtained 30 ODs after HPLC purification and detritylation. ES-MS: expected 6349; found 6349.

SEQ ID NO. 5-3'-Warfarin was synthesized in similar way. Obtained 10 ODs of purified oligonucleotide (should be able to increase this yield with optimization of HPLC conditions). ES-MS: expected 8011, found 8013.
Synthesis Using CPG 12

The oligonucleotide was synthesized using 14 mg of resin (CPG 12), 0.15 M amidite solutions and CSO oxidation. Cleavage and deprotection: 8 h at 55° C. in conc. aq. ammonia. gave SEQ ID NO: 4 sequence. After HPLC purification in trityl-on and purification in trityl-off form, 12 ODs of oligonucleotide were obtained. ES-MS: expected 8011, found 8014.

EXAMPLE 69

Effect of Chemistry on $\alpha_2$-Macroglobulin Binding

The binding affinity of different chemistries was evaluated with $\alpha_2$-macroglobin as the target protein using the techniques that are described in Example 42.

| $K_D$ ($\mu M$) | Description (analogs of SEQ ID No. 4) |
|---|---|
| 0.43 | PS deoxy |
| 0.20 | PS 2'-O-propyl |
| 5.7 | PO 2'-O-methoxyethyl/chlosterol |
| 0.75 | PS 2'-O-methoxyethyl |
| 13.8 | PO 2'-O-methoxyethyl/ibuprofen |
| 1.9 | PO deoxy/palmityl |
| no binding | PO 2'-deoxy |
| no binding | PO 2'-O-propyl |

As can be seen from the tables even with the PO backbone the oligomers exhibit good binding affinity when they have ligands such as cholesterol, ibuprofen and palmitic acid. Among these ligands palmitic acid shows favorable binding to $\alpha_2$-macroglobin while ibuprofen shows favorable to serum albumin.

What is claimed is:

1. An oligomeric compound conjugated to an arylpropionic acid that interacts with a plasma protein, wherein said arylpropionic acid is ibuprofen, suprofen, fenbufen, ketoprofen, (S)-(−)-pranoprofen, or carprofen.

2. The oligomeric compound of claim 1 wherein said arylpropionic acid binds to said protein.

3. An oligomeric compound conjugated to an arylpropionic acid, wherein said arylpropionic acid is ibuprofen, suprofen, fenbufen, ketoprofen, (S)-(+)-pranoprofen, or carprofen.

4. The oligomeric compound of claim 3 wherein said arylpropionic acid is ibuprofen.

5. The oligomeric compound of claim 2 having a Kd lower than 20 $\mu$M with said protein.

6. The oligomeric compound of claim 2 wherein said protein is albumin, an immunoglobulin, α-2-macroglobulin, α-1-glycoprotein or a lipoprotein.

7. The oligomeric compound of claim 3 further including a linking group attaching said arylpropionic acid to said oligomeric compound.

8. The oligomeric compound of claim 7 wherein said linking group is O-aminohexyloxy.

9. The oligomeric compound of claim 3 wherein said compound comprises a plurality of nucleosides connected by covalent internucleoside linkages.

10. The oligomeric compound of claim 9 wherein said linkages are phosphodiester linkages.

11. The oligomeric compound of claim 9 wherein said linkages are phosphorothioate linkages.

12. The oligomeric compound of claim 9 wherein said linkages are non-phosphorous containing linkages.

13. The oligomeric compound of claim 9 wherein at least one of said nucleosides bears a 2'-substituent group.

14. The oligomeric compound of claim 13 wherein said 2'-substituent group is O alkylalkoxy.

15. The oligomeric compound of claim 14 wherein said 2'-substituent group is methoxyethoxy.

16. A method of increasing the concentration of an oligonucleotide in serum comprising the steps of:

(a) selecting an arylpropionic acid that is known to bind to a plasma protein, wherein said arylpropionic acid is ibuprofen, suprofen, fenbufen, ketoprofen, (S)-(−)-pranoprofen or carprofen;

(b) conjugating said arylpropionic acid to said oligonucleotide to form a conjugated oligonucleotide; and (c) adding said conjugated oligonucleotide to said serum.

17. The method of claim 16 wherein said protein is albumin, an immunoglobulin, α-2-macroglobulin, α-1-glycoprotein or a lipoprotein.

18. The method of claim 16 wherein said protein is albumin.

19. A method of increasing the concentration of an oligonucleotide in serum comprising the steps of:

conjugating ibuprofen, suprofen, fenbufen, ketoprofen, (S)-(+)-pranoprofen or carprofen to said oligonucleotide to form a conjugated oligonucleotide; and adding said conjugated oligonucleotide to said serum.

20. The method of claim 16 wherein said arylpropionic acid is ibuprofen.

21. The method of claim 20 wherein said protein is albumin.

22. A method of promoting cellular uptake of an oligonucleotide in a cell comprising the steps of:

(a) selecting an arylpropionic acid that is known to bind to a cell surface integrin, wherein said arylpropionic acid is ibuprofen, suprofen, fenbufen, ketoprofen, (S)-(+)-pranoprofen, or carprofen;

(b) conjugating said arylpropionic acid to said oligonucleotide to form a conjugated oligonucleotide; and (c) exposing said cell to said conjugated oligonucleotide.

23. The oligomeric compound of claim 6 wherein said protein is human serum albumin.

24. The method of claim 18 wherein said protein is human serum albumin.

25. The method of claim 21 wherein said protein is human serum albumin.

* * * * *

UNITED STATES PATENT AND TRADEMARK OFFICE
CERTIFICATE OF CORRECTION

PATENT NO. : 6,762,169 B1
DATED : July 13, 2004
INVENTOR(S) : Muthiah Manoharan

It is certified that error appears in the above-identified patent and that said Letters Patent is hereby corrected as shown below:

<u>Column 71,</u>
Line 30, delete "(S)-(-)-pranoprofen" and insert -- (S)-(+)-pranoprofen --;
Line 48, delete "O-aminohexyloxy" and insert -- 6-aminohexyloxy --;
Line 61, delete "O alkylalkoxy" and insert -- O-alkylalkoxy --.

<u>Column 72,</u>
Lines 28-29, delete "(S)-(-)-pranoprofen" and insert -- (S)-(+)-pranoprofen --.

Signed and Sealed this

Fourth Day of April, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 1
tgcatccccc aggccaccau                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 2
tctgagtagc agaggagccu                                              20

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 3
tctgagtagc agaggagcct                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
tctgagtagc agaggagctc                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
tgcatccccc aggccaccat                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 6
gttctcgctg gtgagtttca                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7
agcttctttg cacatgtaaa                                               20

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 8

Arg Ile Ala Arg Gly Asp Phe Pro Asp Asp Arg Lys
 1               5                  10
```

```
-continued

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 9

Asp Glu Leu Ala Glu Gly Gly Gly Val Arg Gly Pro Arg Val
 1               5                  10

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
tttttttttt tt                                                          12
```